United States Patent
Jung et al.

(10) Patent No.: US 9,005,777 B2
(45) Date of Patent: Apr. 14, 2015

(54) HETEROCYCLIC COMPOUND, ORGANIC LIGHT-EMITTING DIODE INCLUDING THE HETEROCYCLIC COMPOUND, AND FLAT DISPLAY DEVICE INCLUDING THE ORGANIC LIGHT-EMITTING DIODE

(75) Inventors: Hye-Jin Jung, Yongin (KR); Seok-Hwan Hwang, Yongin (KR); Young-Kook Kim, Yongin (KR); Jin-O Lim, Yongin (KR); Sang-Hyun Han, Yongin (KR); Jong-Hyuk Lee, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 210 days.

(21) Appl. No.: 13/414,534

(22) Filed: Mar. 7, 2012

(65) Prior Publication Data

US 2013/0099206 A1 Apr. 25, 2013

(30) Foreign Application Priority Data

Oct. 19, 2011 (KR) .................. 10-2011-0107050

(51) Int. Cl.
*H01L 51/50* (2006.01)
*C07D 471/04* (2006.01)
(Continued)

(52) U.S. Cl.
CPC .............. *C07D 471/04* (2013.01); *C09K 11/06* (2013.01); *H01L 51/0072* (2013.01); *H01L 51/0081* (2013.01); *H01L 51/5072* (2013.01); *H01L 2251/308* (2013.01); *Y10S 428/917* (2013.01)

(58) Field of Classification Search
USPC .................. 428/690, 917; 313/504, 505, 506; 257/40, E51.05, E51.026, E51.032; 546/18, 71, 81, 101; 544/234
See application file for complete search history.

(56) References Cited

U.S. PATENT DOCUMENTS

| 5,635,308 | A | 6/1997 | Inoue et al. |
| 5,645,948 | A | 7/1997 | Shi et al. |

(Continued)

FOREIGN PATENT DOCUMENTS

| JP | 8-12600 | 1/1996 |
| JP | 2000-003782 | 1/2000 |

(Continued)

OTHER PUBLICATIONS

Vaeth et al., Light-emitting diodes based on phosphorescent guest/polymeric host systems, 2002, Journal of Applied Physics, vol. 92, No. 7, pp. 3447-3453.*

(Continued)

*Primary Examiner* — Gregory Clark
(74) *Attorney, Agent, or Firm* — Robert E. Bushnell, Esq.

(57) ABSTRACT

A heterocyclic compound represented by Formula 1 below, and an organic light-emitting diode including the heterocyclic compound, and a flat display device including the organic light-emitting diode.

<Formula 1>

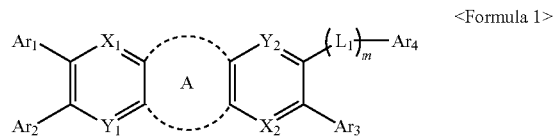

wherein $Ar_1$ to $Ar_4$, $X_1$, $X_2$, $Y_1$, $Y_2$, $L_1$, and m are defined as in the specification.

16 Claims, 1 Drawing Sheet

(51) Int. Cl.
*C09K 11/06* (2006.01)
*H01L 51/00* (2006.01)

(56) References Cited

U.S. PATENT DOCUMENTS

| | | | |
|---|---|---|---|
| 5,972,247 | A | 10/1999 | Shi et al. |
| 6,465,115 | B2 | 10/2002 | Shi et al. |
| 6,596,415 | B2 | 7/2003 | Shi et al. |
| 7,777,043 | B2 | 8/2010 | Yabe et al. |
| 7,846,559 | B2 | 12/2010 | Hwang et al. |
| 7,875,368 | B2 | 1/2011 | Ohrui et al. |
| 2009/0121625 | A1 | 5/2009 | Ohrui et al. |
| 2009/0233937 | A1 | 9/2009 | Ishikawa et al. |
| 2009/0278115 | A1 | 11/2009 | Hosokawa et al. |
| 2011/0049485 | A1 | 3/2011 | Kim et al. |
| 2011/0049488 | A1 | 3/2011 | Kim et al. |
| 2011/0057175 | A1 | 3/2011 | Kim et al. |
| 2011/0204295 | A1 | 8/2011 | Kuwabara et al. |
| 2011/0240977 | A1 | 10/2011 | Jung et al. |

FOREIGN PATENT DOCUMENTS

| | | | | |
|---|---|---|---|---|
| JP | 2005-93159 | A | 4/2005 | |
| JP | 2007-119392 | A | 5/2007 | |
| JP | 2007-230887 | A | 9/2007 | |
| KR | 1020080028424 | A | 3/2008 | |
| KR | 1020090035637 | A | 4/2009 | |
| KR | 1020100105099 | A | 9/2010 | |
| KR | 1020100108924 | A | 10/2010 | |
| KR | 1020100111037 | A | 10/2010 | |
| KR | 2010-0012005 | | 11/2010 | |
| KR | 1020110023091 | A | 3/2011 | |
| KR | 1020110024958 | A | 3/2011 | |
| KR | 1020110025439 | A | 3/2011 | |
| KR | 1020110112121 | A | 10/2011 | |
| WO | WO 2008022633 | * | 2/2008 | ............ C09K 11/06 |
| WO | WO 2011/021545 | * | 2/2011 | ............ C07D 471/04 |
| WO | WO 2011021545 | * | 2/2011 | ............ C09K 11/06 |

OTHER PUBLICATIONS

C.W. Tang and S.A. VanSlyke (1987). Organic electroluminescent diodes. Applied Physics Letters, 51(12).

Chihaya Adachi, T. Tsutsui, and S. Saito (1990). Confinement of charge carriers and molecular excitons within 5-nm-thick emitter layer in organic electroluminescent devices with a double heterostructure. Applied Physics Letters, 57(5).

Youichi Sakamoto, T. Suzuki, A. Miura, H. Fujikawa, S. Tokito, and Y. Taga (2000). Synthesis, characterization, and electron-transport property of perfluorinated phenylene dendrimers. Journal of the American Chemical Society, 122, 1832-1833.

Chemistry Letters 2001;Disphenylamino-Substituted 2,5-Diarylsiloles for Single-Layer Organic Electroluminescent Devices by Shigehiro Yamaguchi et al.

* cited by examiner

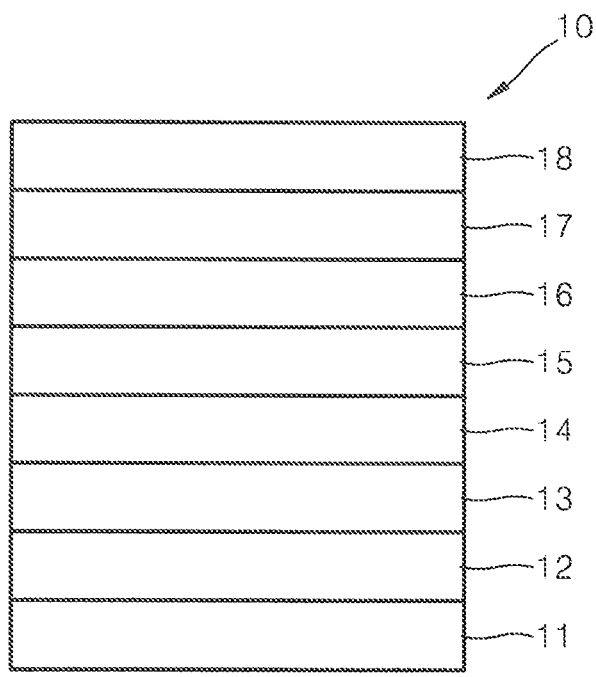

HETEROCYCLIC COMPOUND, ORGANIC LIGHT-EMITTING DIODE INCLUDING THE HETEROCYCLIC COMPOUND, AND FLAT DISPLAY DEVICE INCLUDING THE ORGANIC LIGHT-EMITTING DIODE

CLAIM OF PRIORITY

This application makes reference to, incorporates the same herein, and claims all benefits accruing under 35 U.S.C. §119 from an application for HETEROCYCLIC COMPOUND, ORGANIC LIGHT-EMITTING DIODE INCLUDING THE HETEROCYCLIC COMPOUND, AND FLAT DISPLAY DEVICE INCLUDING THE ORGANIC LIGHT-EMITTING DIODE earlier filed in the Korean Intellectual Property Office on Oct. 19, 2011 and there duly assigned Serial No. 10-2011-0107050.

BACKGROUND OF THE INVENTION

1. Field of the Invention

The present invention relates to a heterocyclic compound represented by Formula 1, an organic light-emitting diode including the heterocyclic compound, and a flat display device including the organic light-emitting diode; and more particularly, to a heterocyclic compound that is suitable for use as a light-emitting material or electron transporting material included in an organic light-emitting diode, an organic light-emitting diode including the heterocyclic compound, and a flat display device including the organic light-emitting diode.

The heterocyclic compound has high glass transition temperature or high melting point, and thus, an organic light-emitting diode including an organic layer that includes the heterocyclic compound has a high charge transporting capability and a high light-emitting capability.

2. Description of the Related Art

Organic light emitting diodes are self-emission devices, and have a wide viewing angle, a high contrast ratio, a short response time, and high brightness, excellent driving voltage, and quick response speed characteristics, and enable generation of multi-color images.

In a typical organic light-emitting diode, an anode is formed on a substrate, and a hole transport layer, an emission layer, an electron transport layer, and a cathode are sequentially formed in this stated order on the anode. In this regard, the hole transport layer, the emission layer, and the electron transport layer are organic films including organic compounds. When a voltage is applied between the anode and the cathode, holes injected from the anode pass the hole transport layer and migrate toward the emission layer, and electrons injected from the cathode pass the electron transport layer and migrate toward the emission layer. The holes and electrons, which are carriers, are recombined in the emission layer to generate excitons, and then the excitons change from an excited state to a ground state, thereby generating light.

In this case, a transition into a ground state through a singlet excited state while emitting light, is referred to as "fluorescence"; and a transition into a ground state through a triplet excited state while emitting light, is referred to as "phosphorescence". In the case of fluorescence, the probability of the singlet excited state is 25% and luminous efficiency of the fluorescence has a limitation. However, in the case of phosphorescence, because a 75% triplet excited state and a 25% single excite state are all used, theoretically, inner quantum efficiency may be increased up to 100%.

U.S. Pat. Nos. 6,596,415 and 6,465,115 disclose organic light-emitting diodes that use 4,4'-N,N'-dicarbazole-biphenyl (CBP) as a host for an emission layer. CBP is widely known as a host material for a phosphorescent emission material. A representative example of an organic light-emitting diode using phosphorescence is a green and red high-efficiency organic light-emitting diode that includes $Ir(ppy)_3$ and PtOEP as dopants and CBP as a host to effectively emit light even in a triplet state (phosphorescence), wherein $Ir(ppy)_3$ and PtOEP are phosphorescent pigments having a heavy atom that has a large spin-orbit bond, such as Ir or Pt in their centers. Recently, iridium (III) complex series are widely known as a phosphorescent emission dopant material, and $(acac)Ir(btp)_2$, $Ir(ppy)_3$ and Firpic are known as a red emission material, a green emission material, and a blue emission material, respectively. Also, an organic light-emitting diode that uses CBP as a host material for a phosphorescent emission material and BCP and BAlq for forming a hole blocking layer to obtain high efficiency, is disclosed, and also a high-performance organic light-emitting diode that uses a BAlq derivative as a host, is disclosed. However, these organic light-emitting diodes have a relatively short lifetime of 150 hours or less, and thus are not efficient for commercial use. A possible cause thereof is a relatively low glass transition temperature of 110° C. or less, high likelihood of crystallization, and low thermal stability of CBT. Due to these properties, CBP may deteriorate when deposited at high temperature.

Japanese Patent Application Publication No. 8-12600 discloses an organic light-emitting diode that uses a dimmer or terpolymer compound of phenylanthracene. However, because the organic light-emitting diode using the dimmer or terpolymer compound of phenylanthracene has two or three anthracenes, an energy gap is narrowed and color purity of blue emission decreases. Also, the compound is easily oxidized and thus impurities may be easily formed and thus, purification of the compound is difficult. To overcome these problems, an anthracene compound in which sites 1 and 9 are substituted with naphthalene or a diphenylanthracene compound in which an m-site of a phenyl group is substituted with an aryl group is used to manufacture an organic light-emitting diode. However, the organic light-emitting diodes using such compounds have low luminous efficiency.

Japanese Patent Application Publication No. 2000-3782 discloses an organic light-emitting diode that uses a monoanthracene derivative that is substituted with naphthalene. However, the organic light-emitting diode is not practically available due to its low luminous efficiency of about 1 cd/A.

U.S. Pat. No. 5,972,247 discloses an organic light-emitting diode that uses a phenyl anthracene structure. However, because the compound is substituted with an aryl group at its m-site, luminous efficiency of the compound is as low as about 2 cd/A, although its heat resistance is high.

Also, KR 2010-0090280 discloses an organic light-emitting diode in which an emission layer includes a fused aromatic cyclic compound that has anthracene and benzophenanthrene.

SUMMARY OF THE INVENTION

The present invention provides a heterocyclic compound having a novel structure, an organic light-emitting diode including an organic layer that includes the heterocyclic compound, and a flat display device including the organic light-emitting diode.

According to an aspect of the present invention, there is provided a heterocyclic compound represented by Formula 1 below:

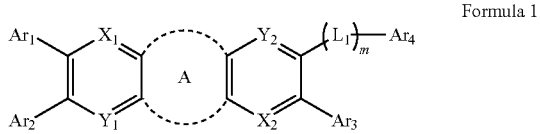

Formula 1 wherein one of $X_1$ and $Y_1$ is N and the other one is $CR_1$; one of $X_2$ and $Y_2$ is N and the other one is $CR_2$; A is a substituted or unsubstituted $C_3$-$C_{60}$ cycloalkyl ring, a substituted or unsubstituted $C_5$-$C_{60}$ aryl ring, a substituted or unsubstituted $C_5$-$C_{60}$ aryloxy ring, a substituted or unsubstituted $C_5$-$C_{60}$ arylthio ring, a substituted or unsubstituted $C_2$-$C_{60}$ fused polycyclic ring, or a combination thereof; $Ar_1$ to $Ar_4$ are each independently a hydrogen atom, a deuterium atom, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group; a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted $C_2$-$C_{60}$ fused polycyclic group, a group represented by $N(Q_1)(Q_2)$, or a group represented by $Si(Q_3)(Q_4)(Q_5)$, wherein $Q_1$ to $Q_5$ are each independently a hydrogen atom, a deuterium atom, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{50}$ heteroaryl group, a substituted or unsubstituted $C_2$-$C_{60}$ fused polycyclic group, or a combination thereof; and from among $Ar_1$ to $Ar_4$, adjacent two or more thereof may be bonded to form a saturated or unsaturated ring; $L_1$ is a substituted or unsubstituted phenylene group, a substituted or unsubstituted naphthylene group, a substituted or unsubstituted biphenylene group, a substituted or unsubstituted pentalenylene group, a substituted or unsubstituted indenylene group, a substituted or unsubstituted azulenylene group, a substituted or unsubstituted heptalenylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted triazolylene group, a substituted or unsubstituted oxadiazolylene group, a substituted or unsubstituted quinolinylene group, a substituted or unsubstituted thiophenylene group, or a combination thereof; m is an integer of 0 to 3; and $R_1$ and $R_2$ are each independently a hydrogen atom, a deuterium atom, a halogen atom, a hydroxyl group, a cyano group, a nitro group, a nitrile group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, or a combination thereof.

According to another aspect of the present invention, there is provided an organic light-emitting diode including: a first electrode; a second electrode disposed facing the first electrode; and an organic layer interposed between the first electrode and the second electrode, wherein the organic layer includes the heterocyclic compound represented by Formula 1, which is used alone or in a mixed from with other materials.

According to another aspect of the present invention, there is provided a flat display device including a transistor including a source, a drain, a gate, and an active layer and an organic light-emitting diode including the heterocyclic compound represented by Formula 1, wherein the organic light-emitting diode includes a first electrode and the first electrode is electrically connected to one of the source and the drain.

BRIEF DESCRIPTION OF THE DRAWINGS

A more complete appreciation of the present invention, and many of the attendant advantages thereof, will be readily apparent as the present invention becomes better understood by reference to the following detailed description when considered in conjunction with the accompanying drawings in which like reference symbols indicate the same or similar components, wherein:

The above and other features and advantages of the present invention will become more apparent by describing in detail exemplary embodiments thereof with reference to FIG. 1 which is a schematic view of an organic light-emitting diode according to an embodiment of the present invention.

DETAILED DESCRIPTION OF THE INVENTION

The present invention will now be described more fully with reference to the accompanying drawings, in which exemplary embodiments of the present invention are shown. Expressions such as "at least one of," when preceding a list of elements, modify the entire list of elements and do not modify the individual elements of the list.

An aspect of the present invention provides a heterocyclic compound represented by Formula 1 below:

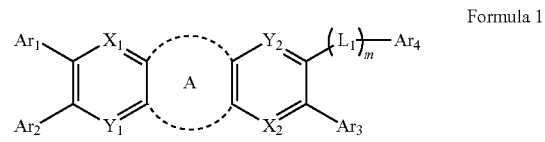

Formula 1

In Formula 1, one of $X_1$ and $Y_1$ may be N and the other one may be $CR_1$, and one of $X_2$ and $Y_2$ may be N and the other one may be $CR_2$. That is, when $X_1$ is N, $Y_1$ is a group including carbon ($CR_1$), and when $X_1$ is a group including carbon ($CR_1$), $Y_1$ is N. Likewise, one of $X_2$ and $Y_2$ may be N and the other one may be $CR_2$. A cycle including $X_1$ and $Y_1$ and a cycle including $X_2$ and $Y_2$ each form a pyridine cycle.

In Formula 1, A may be a substituted or unsubstituted $C_3$-$C_{60}$ cycloalkyl ring, a substituted or unsubstituted $C_5$-$C_{60}$ aryl ring, a substituted or unsubstituted $C_5$-$C_{60}$ aryloxy ring, a substituted or unsubstituted $C_5$-$C_{60}$ arylthio ring, a substituted or unsubstituted $C_2$-$C_{60}$ fused polycyclic ring, or a combination thereof. A may be a mono-cyclic or a poly-cyclic ring.

In Formula 1, $Ar_1$ to $Ar_4$ may be each independently a hydrogen atom, a deuterium atom, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted $C_2$-$C_{60}$ fused polycyclic group, a group represented by $N(Q_1)(Q_2)$, or a group represented by $Si(Q_3)(Q_4)(Q_5)$ (where $Q_1$ to $Q_5$ may be each independently a hydrogen atom, a deuterium atom, a halogen atom, a hydroxyl group, a cyano group, a nitro group, a carboxyl group, a silyl group, a substituted or unsubstituted $C_1$-$C_{50}$ so alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted $C_2$-$C_{60}$ fused polycyclic group, or a combination thereof). From among $Ar_1$ to $Ar_4$, adjacent two or more thereof may be bonded to form a saturated or unsaturated ring.

In Formula 1, $L_1$ may be a linker, and may be a substituted or unsubstituted phenylene group, a substituted or unsubstituted naphthylene group, a substituted or unsubstituted biphenylene group, a substituted or unsubstituted pentalenylene group, a substituted or unsubstituted indenylene group, a substituted or unsubstituted azulenylene group, a substituted or unsubstituted heptalenylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted triazolylene group, a substituted or unsubstituted oxadiazolylene group, a substituted or unsubstituted quinolinylene group, a substituted or unsubstituted thiophenylene group, or a combination thereof; and m may be an integer of 0 to 3. If m is 0, $L_1$ means a single bond, and if m is 2 or more, a plurality of $L_1$ may be identical to or different from each other.

In Formula 1, $R_1$ and $R_2$ may be each independently a hydrogen atom, a deuterium atom, a halogen atom, a hydroxyl group, a cyano group, a nitro group, a nitrile group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, or a combination thereof.

The heterocyclic compound represented by Formula 1 may have a high glass transition temperature or melting point due to the introduction of a heterocyclic skeleton therein. Accordingly, an organic light-emitting diode including the heterocyclic compound represented by Formula 1 has a resistance against a Joule's heat generated in an organic layer during light emission, a Joule's heat that is generated between organic layers, or a Joule's heat that is generated between an organic layer and a metallic electrode, and thus has stronger resistance under high-temperature environments.

The heterocyclic compound represented by Formula 1 has electrical stability, a high charge transporting capability, and a high light-emitting capability, and thus when used in an organic light-emitting diode, the heterocyclic compound may be effectively used as a light-emitting material or an electron injection material or an electron transport material in various colors, such as red, green, blue, and white fluorescent and phosphorescent devices.

The heterocyclic compound represented by Formula 1 may be represented by Formulae 2A or 2B below:

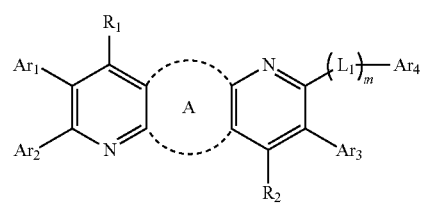

Formula 2A

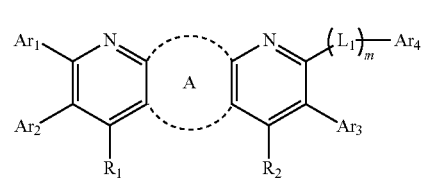

Formula 2B

In Formulae 2A and 2B, A may be a substituted or unsubstituted naphthalene ring, a substituted or unsubstituted pentalene ring, a substituted or unsubstituted indene ring, a substituted or unsubstituted azulene ring, a substituted or unsubstituted heptalene ring, a substituted or unsubstituted indacene ring, a substituted or unsubstituted acenaphthalene ring, a substituted or unsubstituted fluorene ring, a substituted or unsubstituted spiro-fluorene ring, a substituted or unsubstituted phenalene ring, a substituted or unsubstituted phenanthrene ring, a substituted or unsubstituted anthracene ring, a substituted or unsubstituted fluoranthene ring, a substituted or unsubstituted triphenylene ring, a substituted or unsubstituted pyrene ring, a substituted or unsubstituted chrysene ring, a substituted or unsubstituted naphthacene ring, a substituted or unsubstituted tetrahelicene ring, a substituted or unsubstituted picene ring, a substituted or unsubstituted perylene ring, a substituted or unsubstituted pentaphene ring, a substituted or unsubstituted benzopyrene ring and substituted or unsubstituted hexacene ring, or a combination thereof. Also, $Ar_1$, $Ar_2$, $Ar_3$, $Ar_4$, $L_1$, m, $R_1$ and $R_2$ have already been defined with reference to Formula 1.

The heterocyclic compound represented by Formula 1 may be represented by Formulae 3A or 3B below:

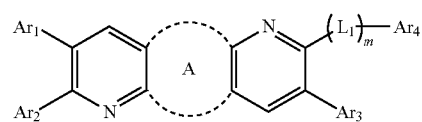

Formula 3A

-continued

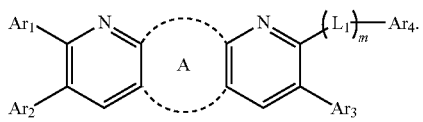

Formula 3B

In Formulae 3A and 3B, A forms a skeleton together with a pyridine group, and may be a substituted or unsubstituted naphthalene ring, a substituted or unsubstituted pentalene ring, a substituted or unsubstituted indene ring, a substituted or unsubstituted azulene ring, a substituted or unsubstituted heptalene ring, a substituted or unsubstituted indacene ring, a substituted or unsubstituted acenaphthalene ring, a substituted or unsubstituted fluorene ring, a substituted or unsubstituted spiro-fluorene ring, a substituted or unsubstituted phenalene ring, a substituted or unsubstituted phenanthrene ring, a substituted or unsubstituted anthracene ring, a substituted or unsubstituted fluoranthene ring, a substituted or unsubstituted triphenylene ring, a substituted or unsubstituted pyrene ring, a substituted or unsubstituted chrysene ring, a substituted or unsubstituted naphthacene ring, a substituted or unsubstituted tetrahelicene ring, a substituted or unsubstituted picene ring, a substituted or unsubstituted perylene ring, a substituted or unsubstituted pentaphene ring, a substituted or unsubstituted benzopyrene ring, a substituted or unsubstituted hexacene ring, or a combination thereof.

In Formulae 3A and 3B, $Ar_1$, $Ar_2$, $Ar_3$, and $Ar_4$ are substituents and may be each independently a hydrogen atom, a deuterium atom, a halogen atom, a hydroxyl group, a cyano group, a nitro group, a carboxyl group, a silyl group, a substituted or unsubstituted methyl group, a substituted or unsubstituted ethyl group, a substituted or unsubstituted propyl group, a substituted or unsubstituted butyl group, a substituted or unsubstituted isobutyl group, a substituted or unsubstituted phenyl group, a substituted or unsubstituted biphenyl group, a substituted or unsubstituted naphthyl group, a substituted or unsubstituted imidazolyl group, a substituted or unsubstituted benzoimidazolyl group, a substituted or unsubstituted phenylbenzoimidazolyl group, a substituted or unsubstituted pyridinyl group, a substituted or unsubstituted phenylpyridinyl group, a substituted or unsubstituted bipyridinyl group, a substituted or unsubstituted imidazopyridinyl group, a substituted or unsubstituted phenylimidazopyridinyl group, a substituted or unsubstituted pyrimidinyl group, a substituted or unsubstituted phenylpyrimidinyl group, a substituted or unsubstituted imidazopyrimidinyl group, a substituted or unsubstituted phenylimidazopyrimidinyl group, a substituted or unsubstituted pyrazinyl group, a substituted or unsubstituted quinolinyl group, a substituted or unsubstituted isoquinolinyl group, a substituted or unsubstituted thiophenyl group, a substituted or unsubstituted benzo[b]thiophenyl group, a substituted or unsubstituted bithiophenyl group, a substituted or unsubstituted dibenzothiophenyl group, a substituted or unsubstituted oxadiazolyl group, a substituted or unsubstituted phenyloxadiazolyl group, a substituted or unsubstituted triazinyl group, a substituted or unsubstituted phenyltriazinyl group, a substituted or unsubstituted triazolyl group, a substituted or unsubstituted phenyltriazolyl group, or a combination thereof.

In Formulae 3A and 3B, $L_1$ is a linker and may be a substituted or unsubstituted phenylene group, a substituted or unsubstituted naphthylene group, a substituted or unsubstituted biphenylene group, a substituted or unsubstituted pentalenylene group, a substituted or unsubstituted indenylene group, a substituted or unsubstituted azulenylene group, a substituted or unsubstituted heptalenylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted triazolylene group, a substituted or unsubstituted oxadiazolylene group, a substituted or unsubstituted quinolinylene group, a substituted or unsubstituted thiophenylene group, or a combination thereof, and m is 0 or 1. If m is 0, $L_1$ means a single bond.

The heterocyclic compound represented by Formula 1 may be represented by one of Formulae 4A to 4H below:

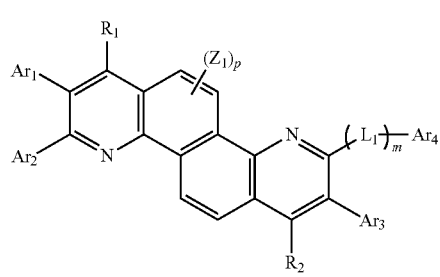

Formula 4A

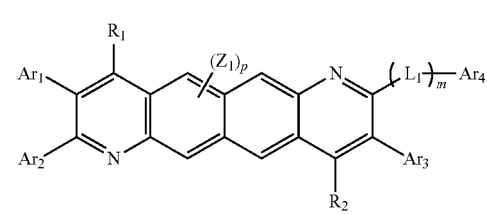

Formula 4B

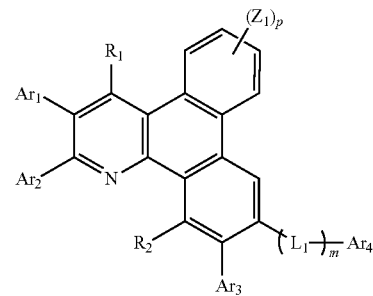

Formula 4C

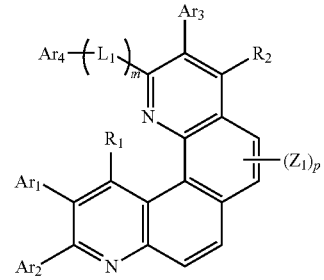

Formula 4D

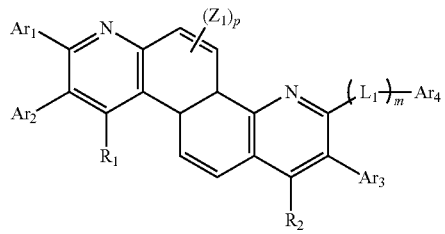

Formula 4E

Formula 4F
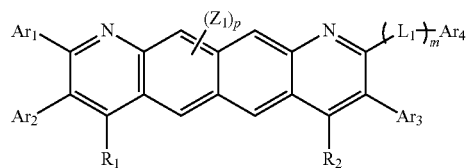
Formula 4G
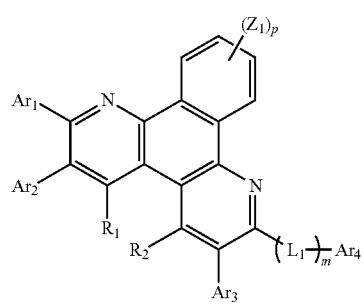
Formula 4H
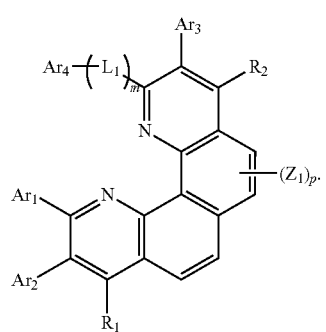
The heterocyclic compound represented by Formula 1 may be represented by one of Formulae 5A to 5F below:
Formula 5A
Formula 5B
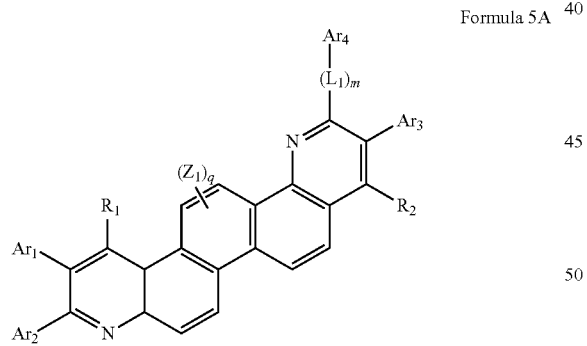
Formula 5C
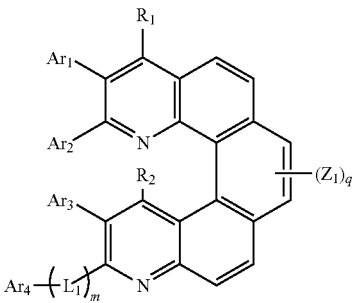
Formula 5D
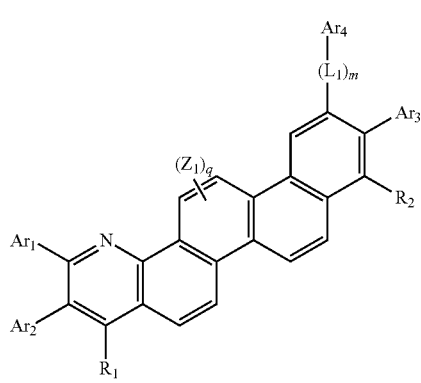
Formula 5E
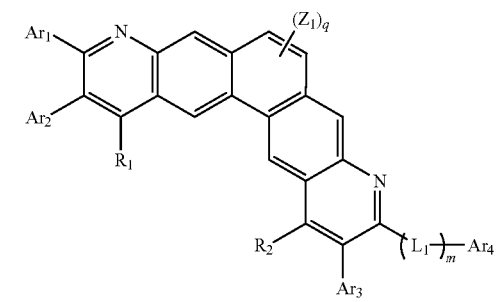
Formula 5F
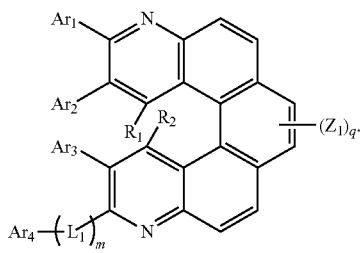
The heterocyclic compound represented by Formula 1 may be represented by one of Formulae 6A to 6F below:

Formula 6A
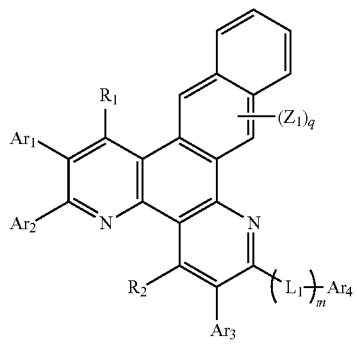
Formula 6B
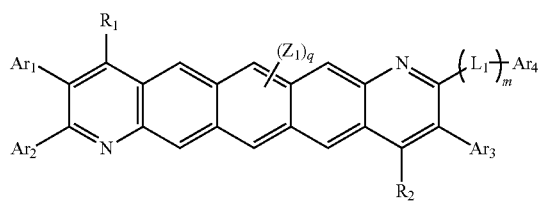
Formula 6C
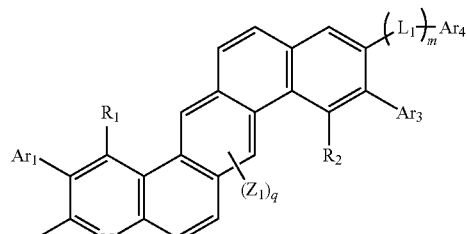
Formula 6D
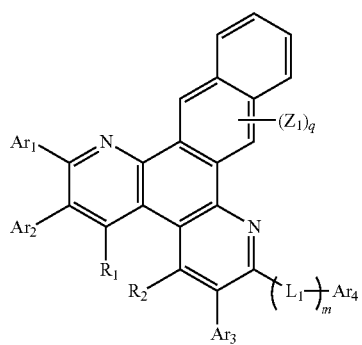
Formula 6E
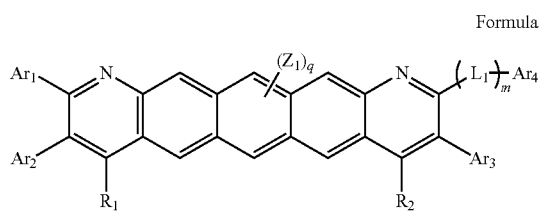
Formula 6F
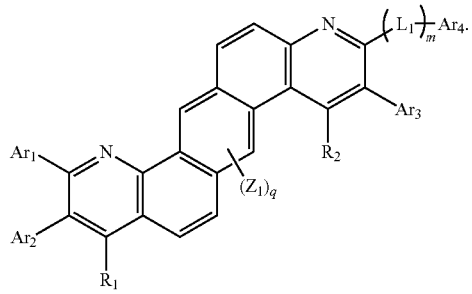
The heterocyclic compound represented by Formula 1 may be represented by one of Formulae 7A to 7F below:
Formula 7A
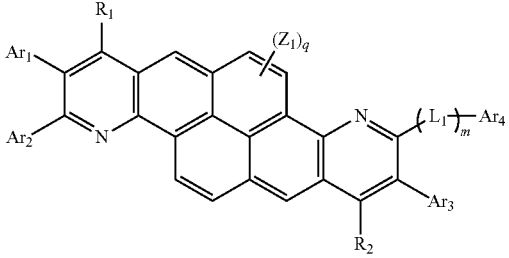
Formula 7B
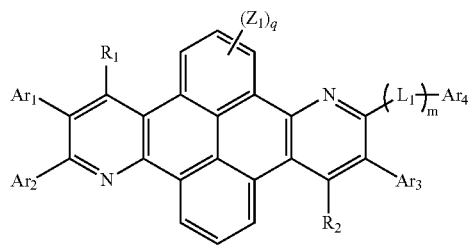
Formula 7C
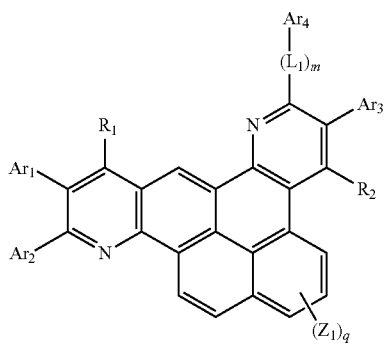
Formula 7D
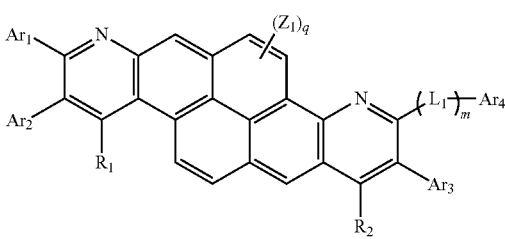

Formula 7E
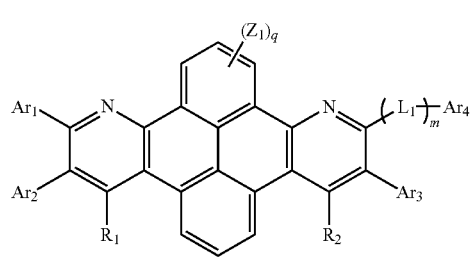
Formula 7F
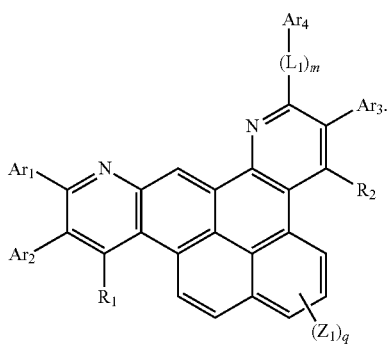
The heterocyclic compound represented by Formula 1 may be represented by one of Formulae 8A to 8F below:
Formula 8A
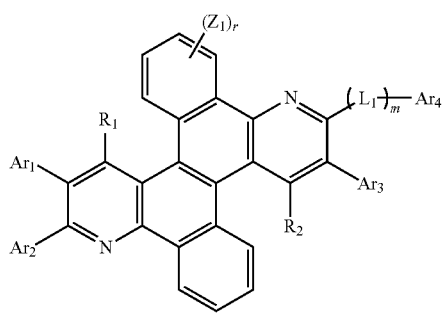
Formula 8B
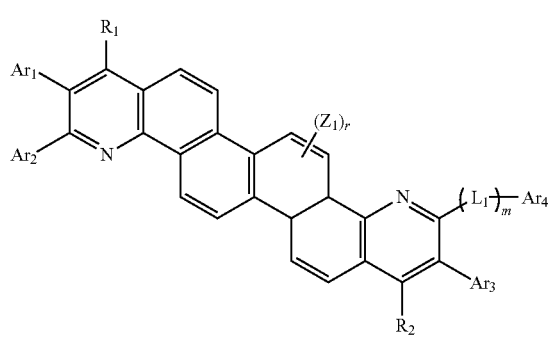
Formula 8C
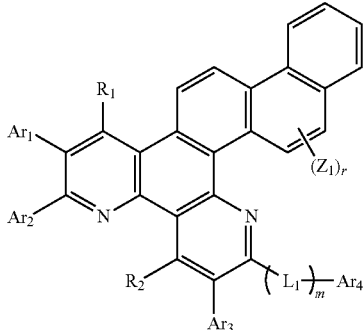
Formula 8D
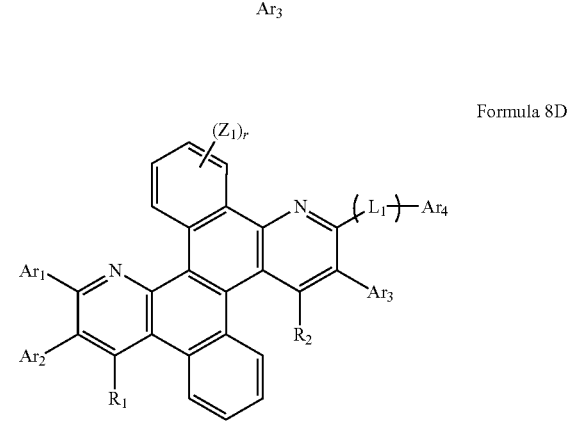
<Formula 8E>
Formula 8F
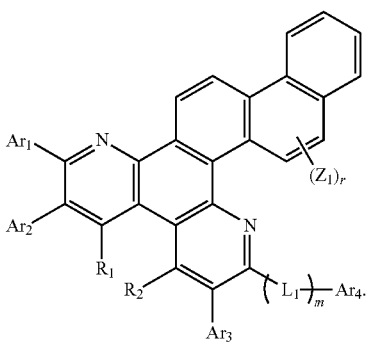
The heterocyclic compound represented by Formula 1 may be represented by Formula 9A or Formula 9B below:

Formula 9A
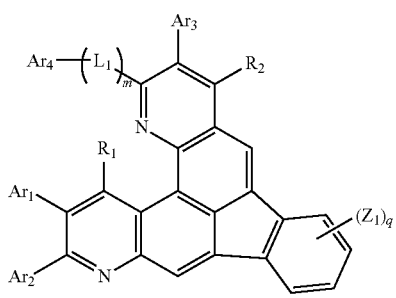
Formula 9B
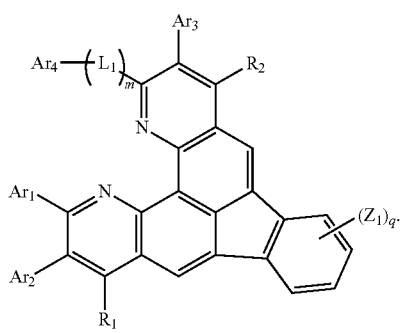
The heterocyclic compound represented by Formula 1 may be represented by one of Formulae 10A to 10F. below:
Formula 10A
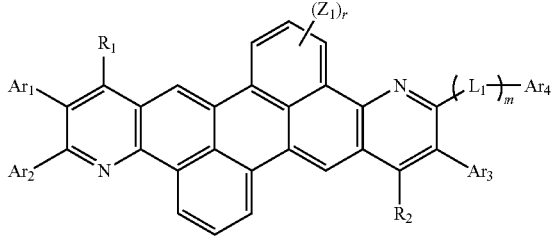
Formula 10B
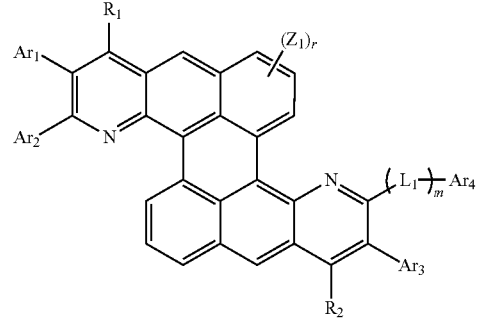
Formula 10C
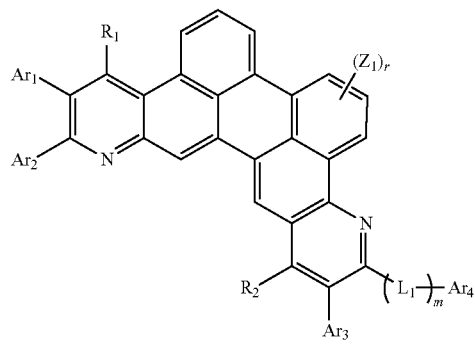
Formula 10D
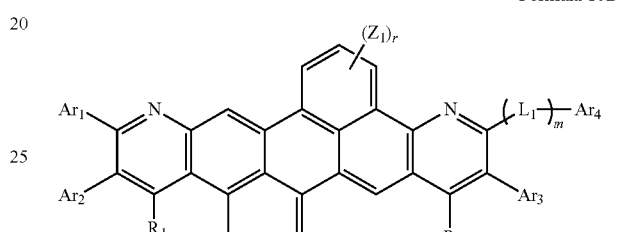
Formula 10E
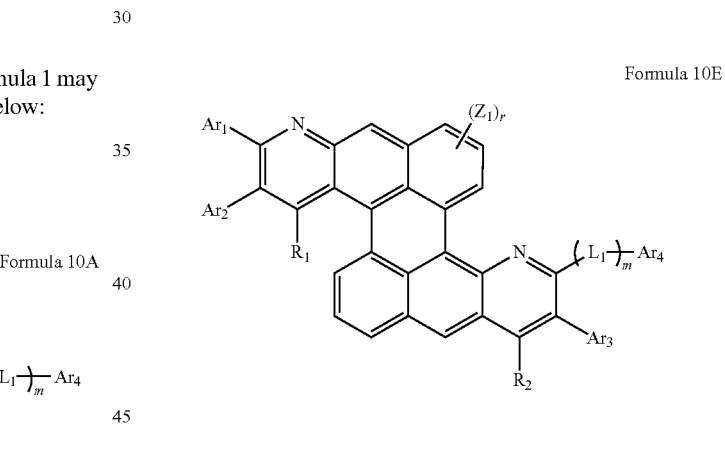
Formual 10F
The heterocyclic compound represented by Formula 1 may be represented by Formula 11A or Formula 11B below:

Formula 11A

[chemical structure]

Formula 11B

[chemical structure]

The heterocyclic compound represented by Formula 1 may be represented by Formula 12A or Formula 12B below:

Formula 12A

[chemical structure]

Formula 12B

[chemical structure]

The heterocyclic compound represented by Formula 1 may be represented by Formula 13A or Formula 13B below:

Formula 13A

[chemical structure]

Formula 13B

[chemical structure]

In Formulae 4A to 4H, 5A to 5F, 6A to 6F, 7A to 7F, 8A to 8F, 9A and 9B, 10A to 10F, 11A and 11B, 12A and 12B, and 13A and 13B, $Ar_1$, $Ar_2$, $Ar_3$ and $Ar_4$ may be each independently a hydrogen atom, a deuterium atom, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or, unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted fused polycyclic group, a group represented by $N(Q_1)(Q_2)$, or a group represented by $Si(Q_3)(Q_4)(Q_5)$ (wherein $Q_1$ to $Q_5$ may be each independently a hydrogen atom, a deuterium atom, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted $C_2$-$C_{60}$ fused polycyclic group, or a combination thereof.)

From among $Ar_1$ to $Ar_4$, adjacent two or more thereof may be bonded to form a saturated or unsaturated ring.

For example, $Ar_1$, $Ar_2$, $Ar_3$ and $Ar_4$ may be each independently a hydrogen atom, a deuterium atom, a halogen atom, a hydroxyl group, a cyano group, a nitro group, a carboxyl group, a silyl group, a substituted or unsubstituted methyl group, a substituted or unsubstituted ethyl group, a substituted or unsubstituted propyl group, a substituted or unsubstituted butyl group, a substituted or unsubstituted isobutyl group, a substituted or unsubstituted phenyl group, a substituted or unsubstituted biphenyl group, a substituted or unsubstituted naphthyl group, a substituted or unsubstituted imidazolyl group, a substituted or unsubstituted benzoimidazolyl group, a substituted or unsubstituted phenylbenzoimidazolyl group, a substituted or unsubstituted pyridinyl group, a substituted or unsubstituted phenylpyridinyl group, a substituted or unsubstituted bipyridinyl group, a substituted or unsubstituted imidazopyridinyl group, a substituted or unsubstituted phenylimidazopyridinyl group, a substituted or unsubstituted pyrimidinyl group, a substituted or unsubstituted phenylpyrimidinyl group, a substituted or unsubstituted imidazopyrimidinyl group, a substituted or unsubstituted phenylimidazopyrimidinyl group, a substituted or unsubstituted pyrazinyl group, a substituted or unsubstituted quinolinyl group, a substituted or unsubstituted isoquinolinyl group, a substituted or unsubstituted thiophenyl group, a substituted or unsubstituted benzo[b]thiophenyl group, a substituted or unsubstituted bithiophenyl group, a substituted or unsubstituted dibenzothiophenyl group, a substituted or unsubstituted oxadiazolyl group, a substituted or unsubstituted phenyloxadiazolyl group, a substituted or unsubstituted triazinyl group, a substituted or unsubstituted phenyltriazinyl group, a substituted or unsubstituted triazolyl group, a substituted or unsubstituted phenyltriazolyl group, or a combination thereof.

$L_1$ may be a substituted or unsubstituted phenylene group, a substituted or unsubstituted naphthylene group, a substituted or unsubstituted biphenylene group, a substituted or unsubstituted pentalenylene group, a substituted or unsubstituted indenylene group, a substituted or unsubstituted azulenylene group, a substituted or unsubstituted heptalenylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted triazolylene group, a substituted or unsubstituted oxadiazolylene group, a substituted or unsubstituted quinolinylene group, a substituted or unsubstituted thiophenylene group, or a combination thereof, and m may be an integer of 0 to 3.

$R_1$ and $R_2$ may be each independently a hydrogen atom, a deuterium atom, a halogen atom, a hydroxyl group, a cyano group, a nitro group, a nitrile group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, or a combination thereof.

For example, $R_1$ and $R_2$ may be each independently a hydrogen atom, a deuterium atom, a halogen atom, a hydroxyl group, a cyano group, a nitro group, a nitrile group, a carboxyl group, a silyl group, or a substituted or unsubstituted $C_1$-$C_{50}$ alkyl group.

$Z_1$ may be independently a hydrogen atom, a deuterium atom, a halogen atom, a hydroxyl group, a cyano group, a nitro group, a nitrile group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, or a combination thereof.

P may be an integer of 1 to 4, q may be an integer of 1 to 6, r may be an integer of 1 to 8, and when p, q or r are 2 or more, a plurality of $Z_1$ may be identical to or different from each other.

The heterocyclic compounds represented by Formulae 4A to 4H, 5A to 5F, 6A to 6F, 7A to 7F, 8A to 8F, 9A and 9B, 10A to 10F, 11A and 11B, 12A and 12B, and 13A and 13B may include a pyridine structure in their skeletons, in particular, at opposite terminals of their skeletons. Thus, an organic light-emitting diode including the heterocyclic compounds has high durability during preservation and operation.

Detailed examples of the heterocyclic compound represented by Formula 1 are Compounds 1 to 79, but are not limited thereto:

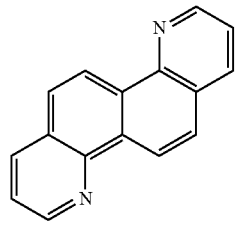

1

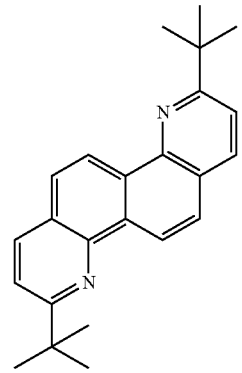

2

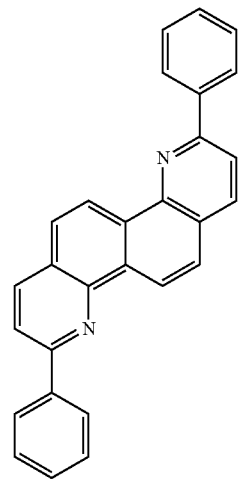

3

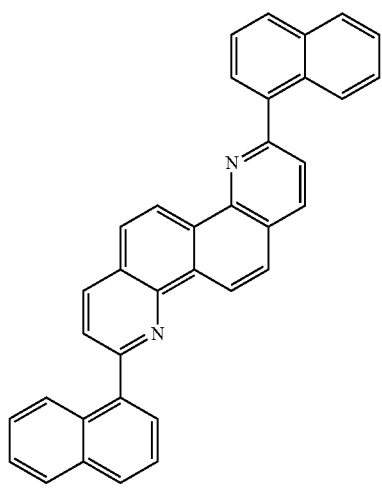
4
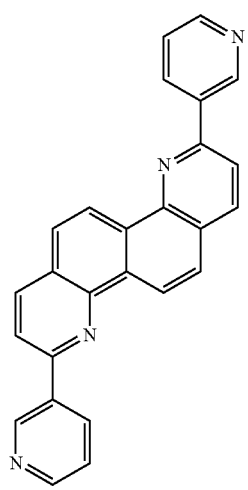
5
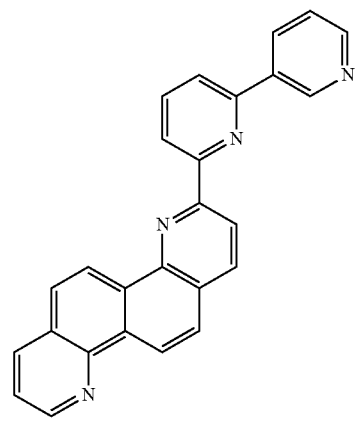
6
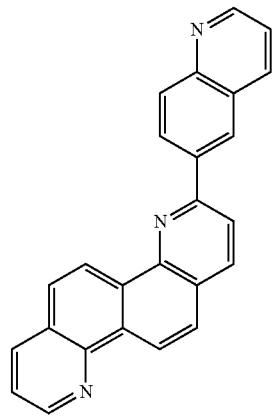
7
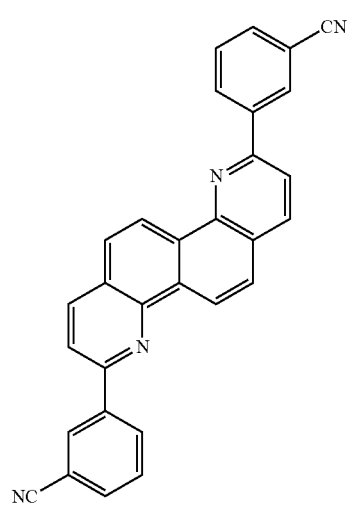
8
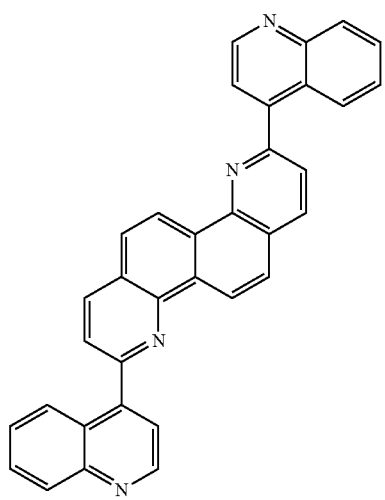
9

-continued
10
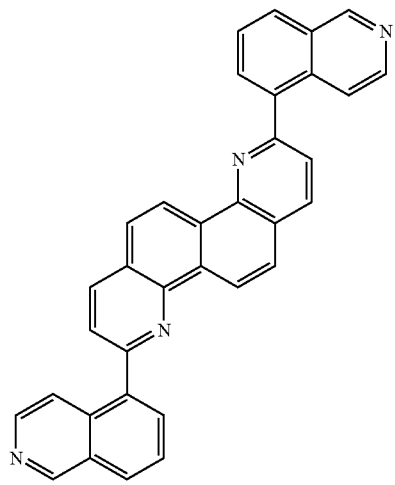
11
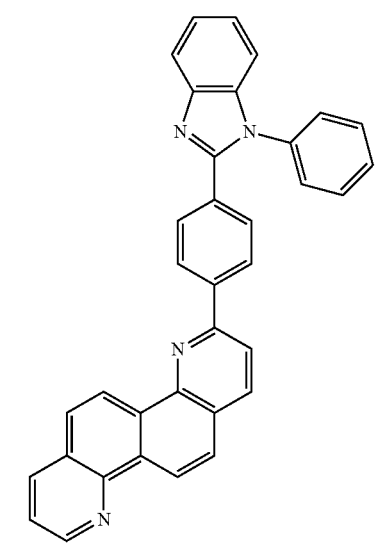
12
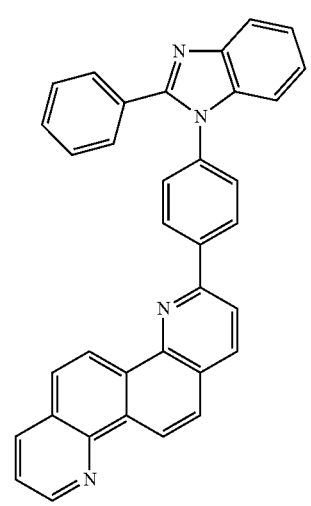
-continued
13
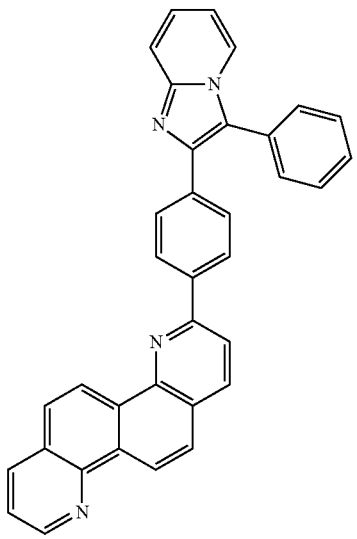
14
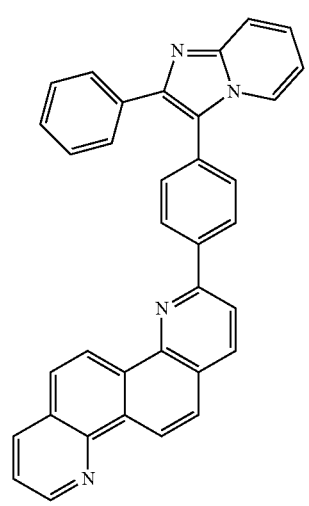
15
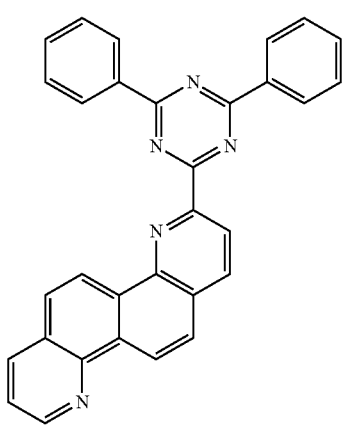

16
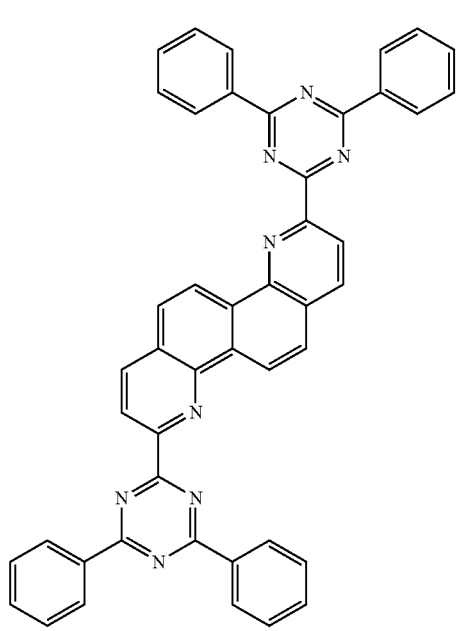
17
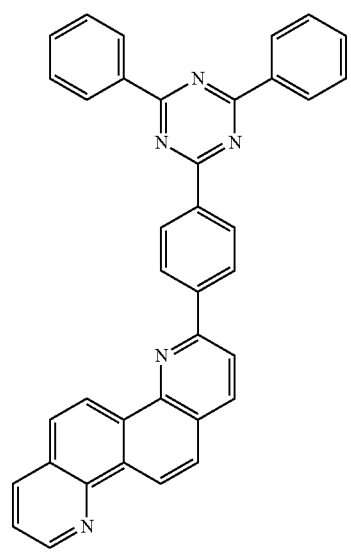
18
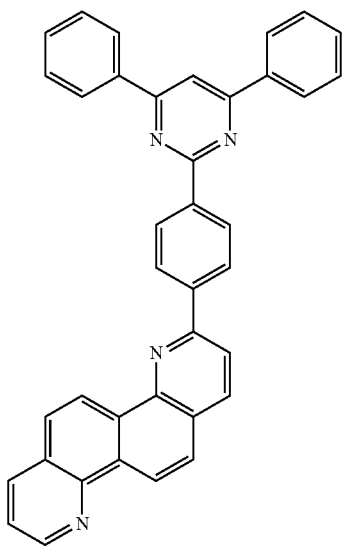
19
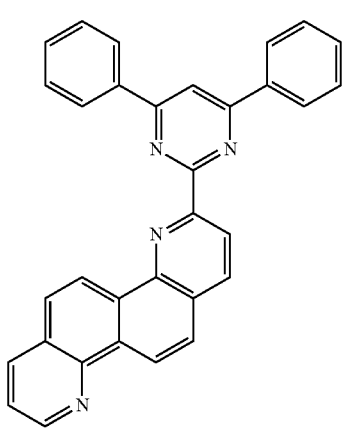
20
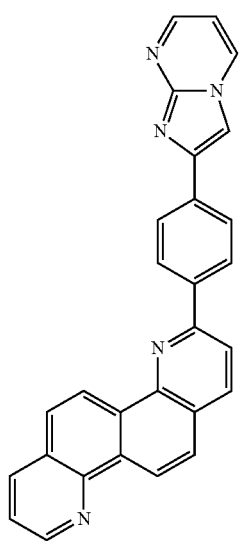

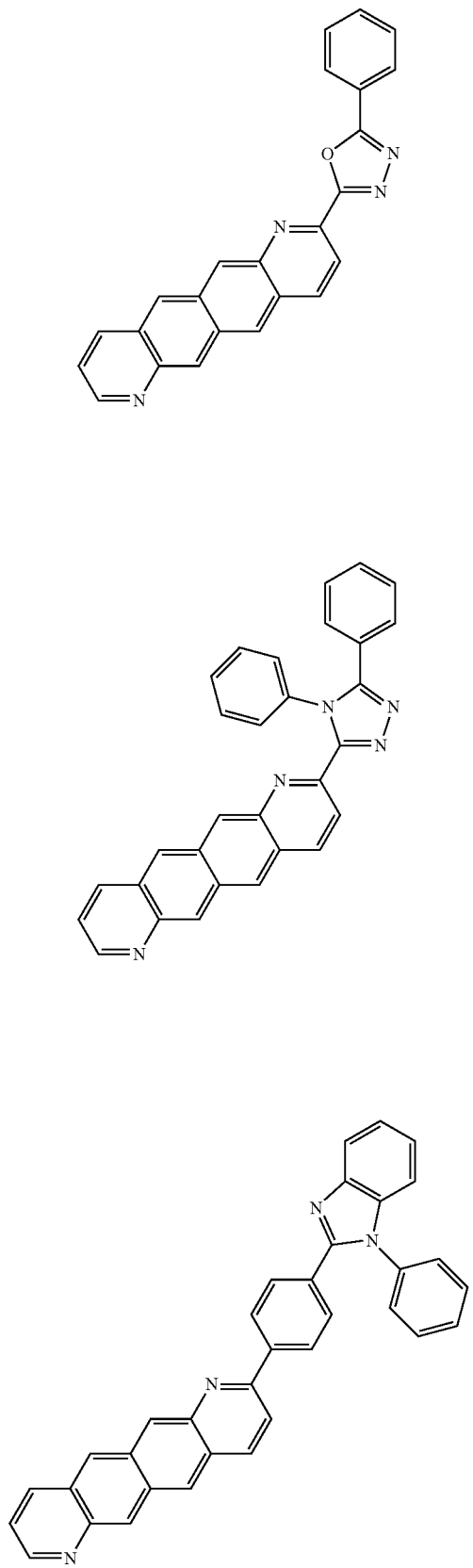
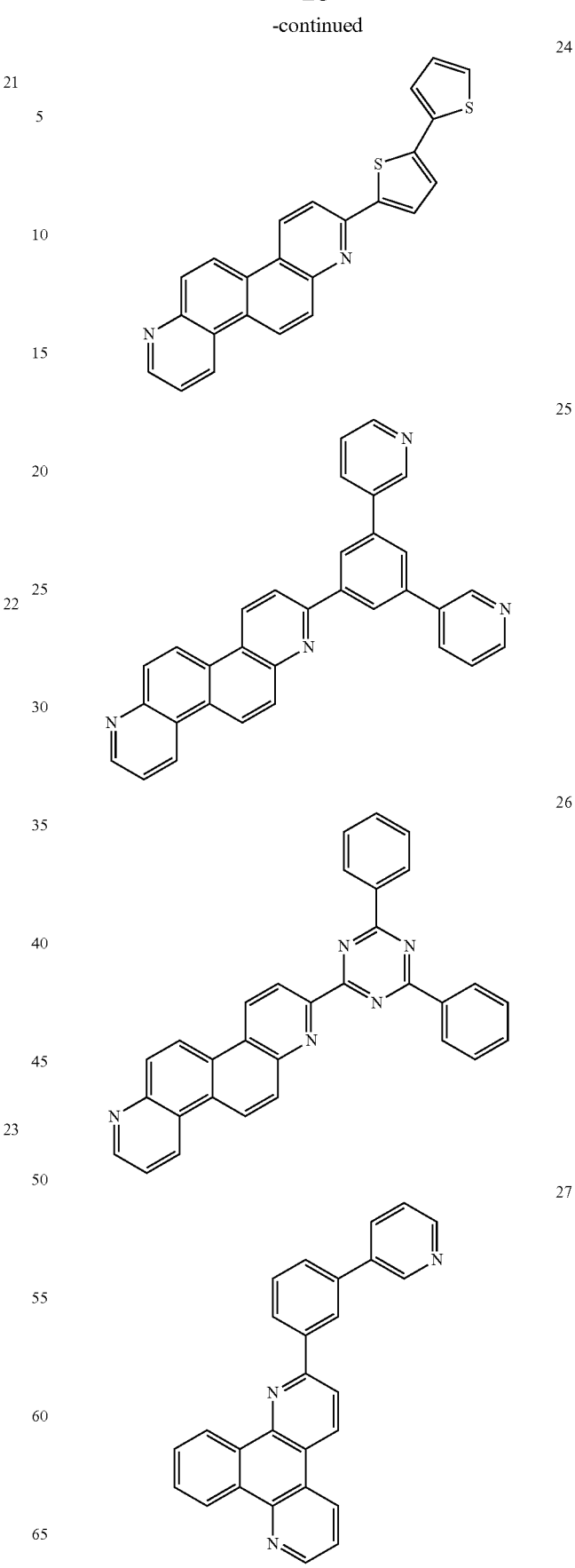

28
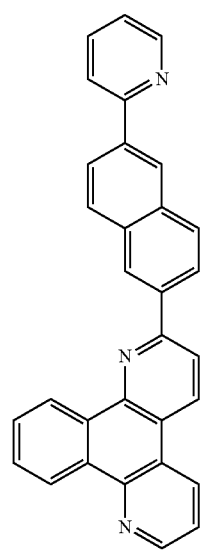
29
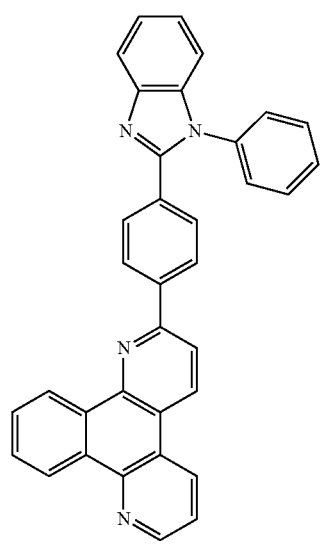
30
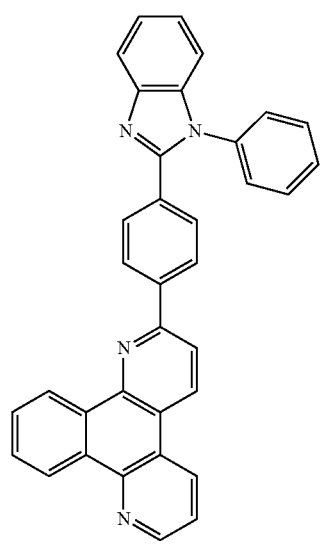
31
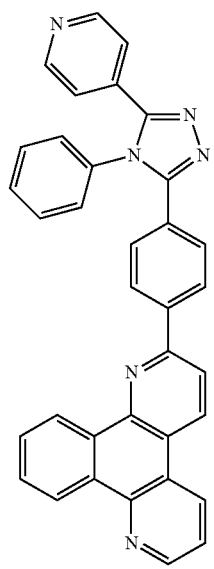
32
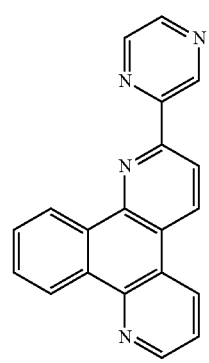
33
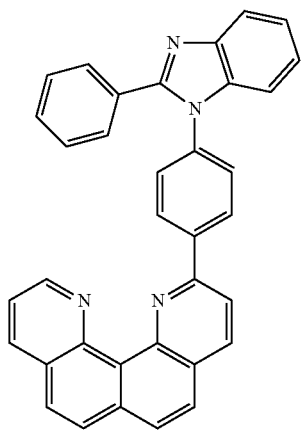

31
-continued
33
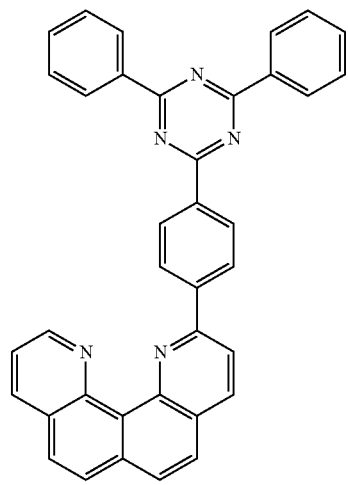
35
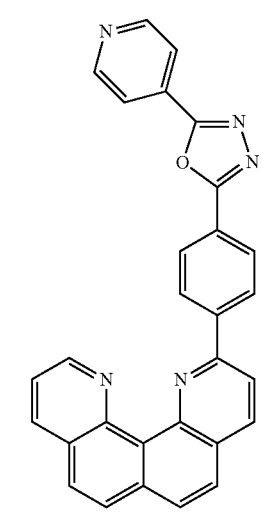
36
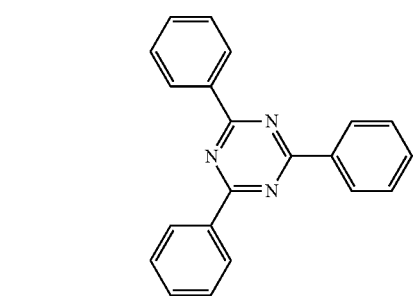
32
-continued
34
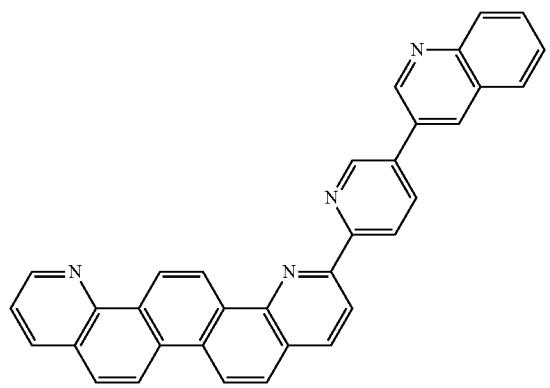
37
38
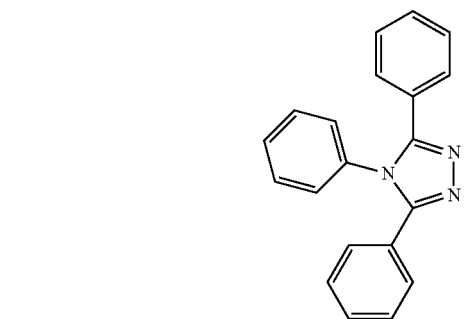
39
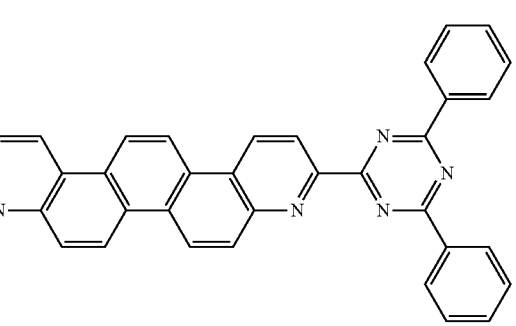
40
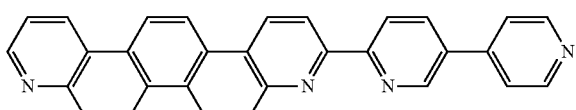
41
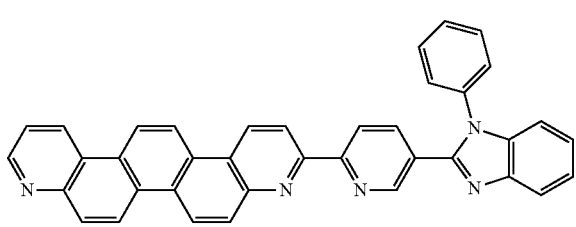

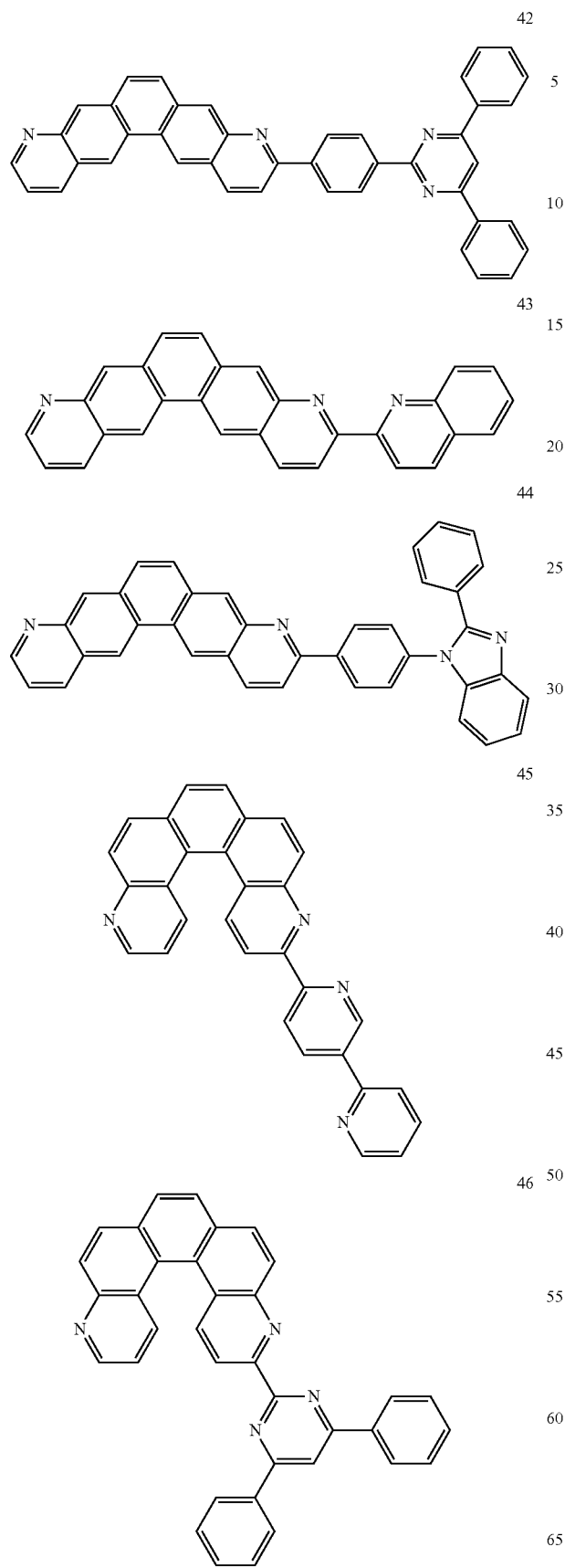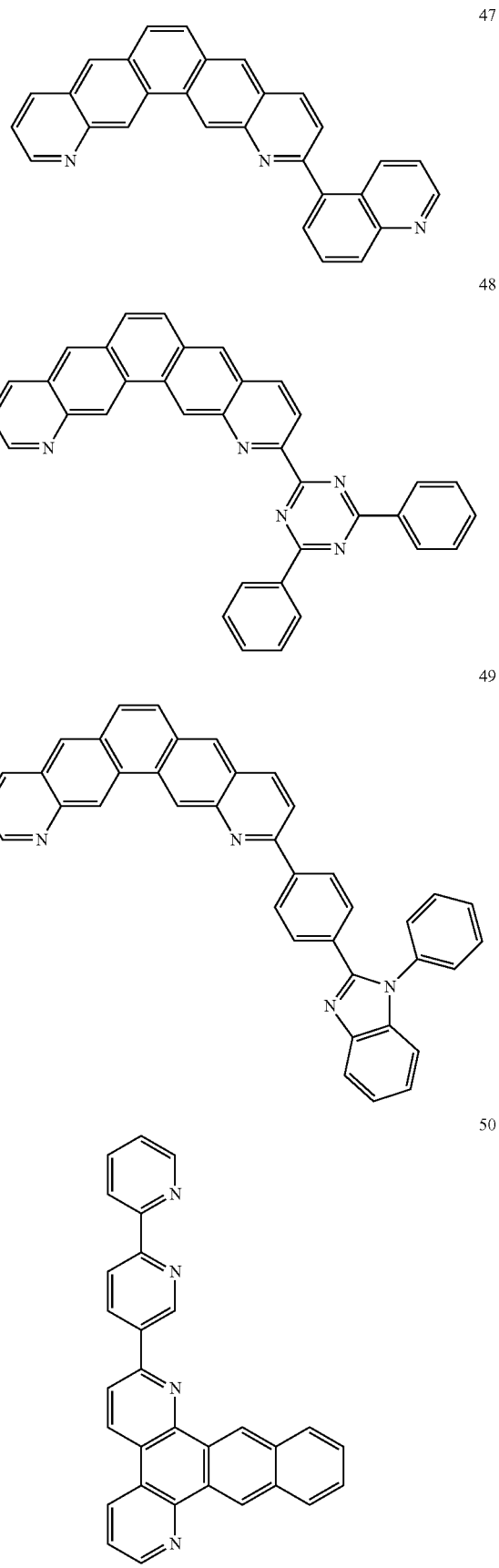

51
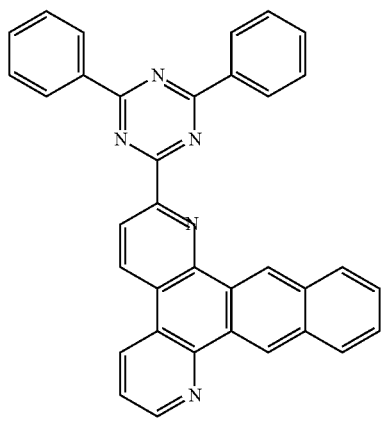
52
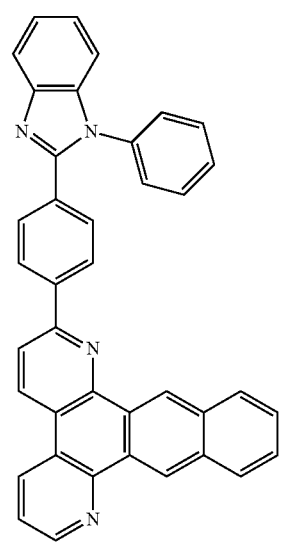
53
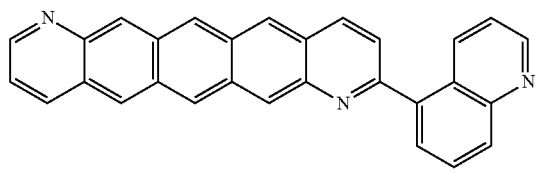
54
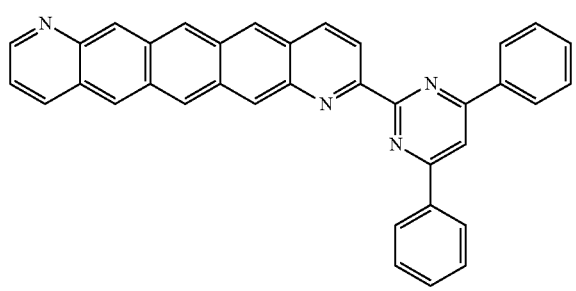
55
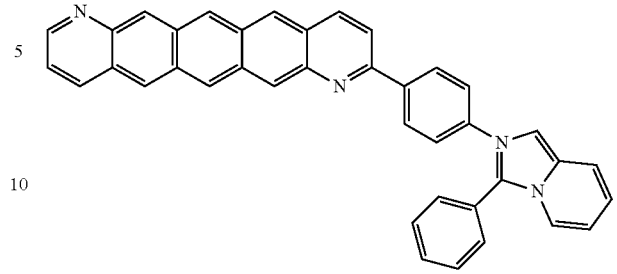
56
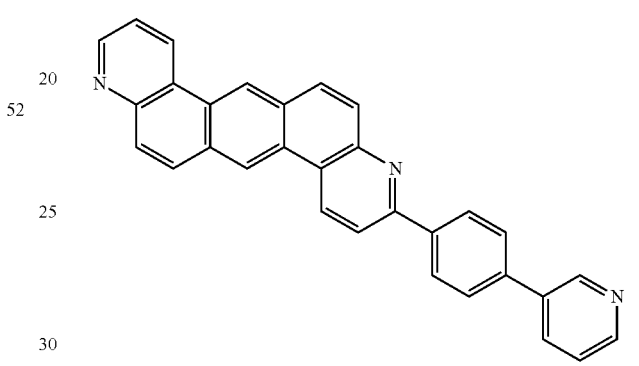
57
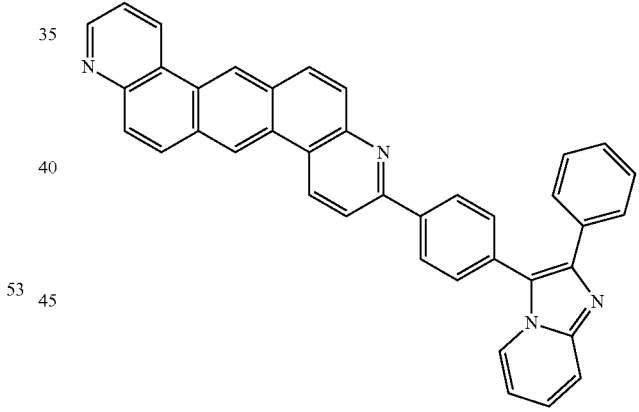
58
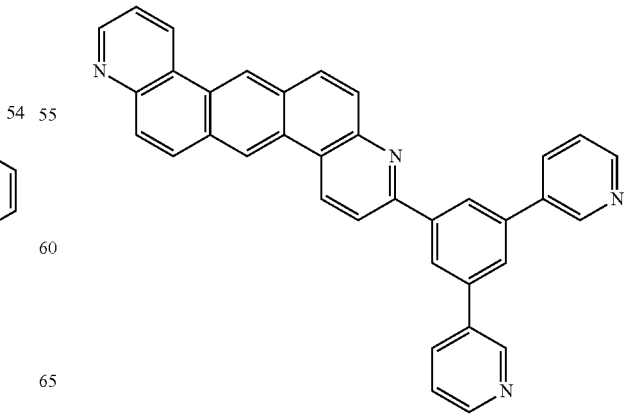

-continued
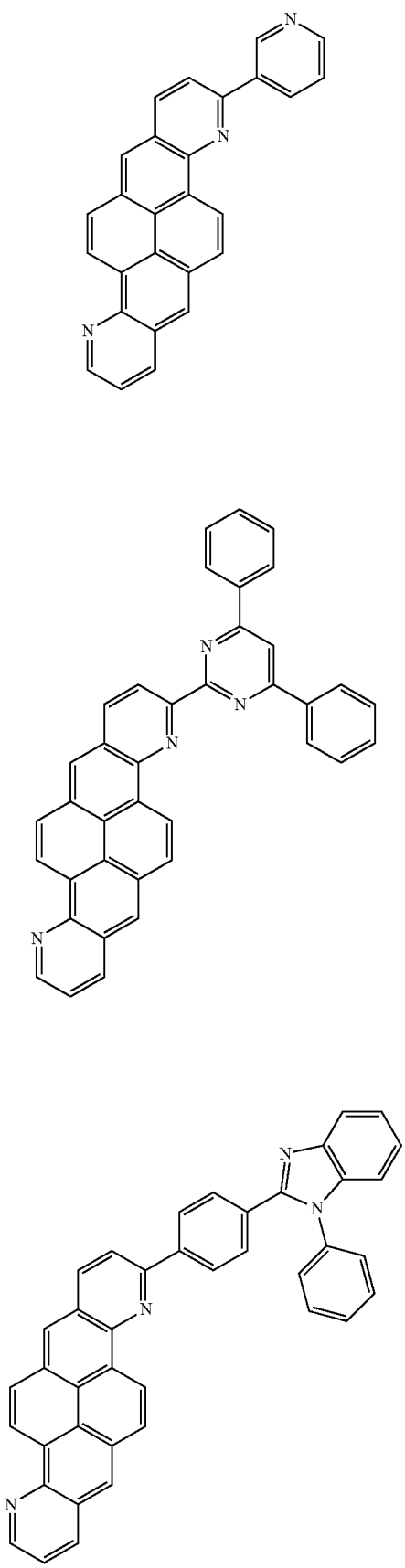
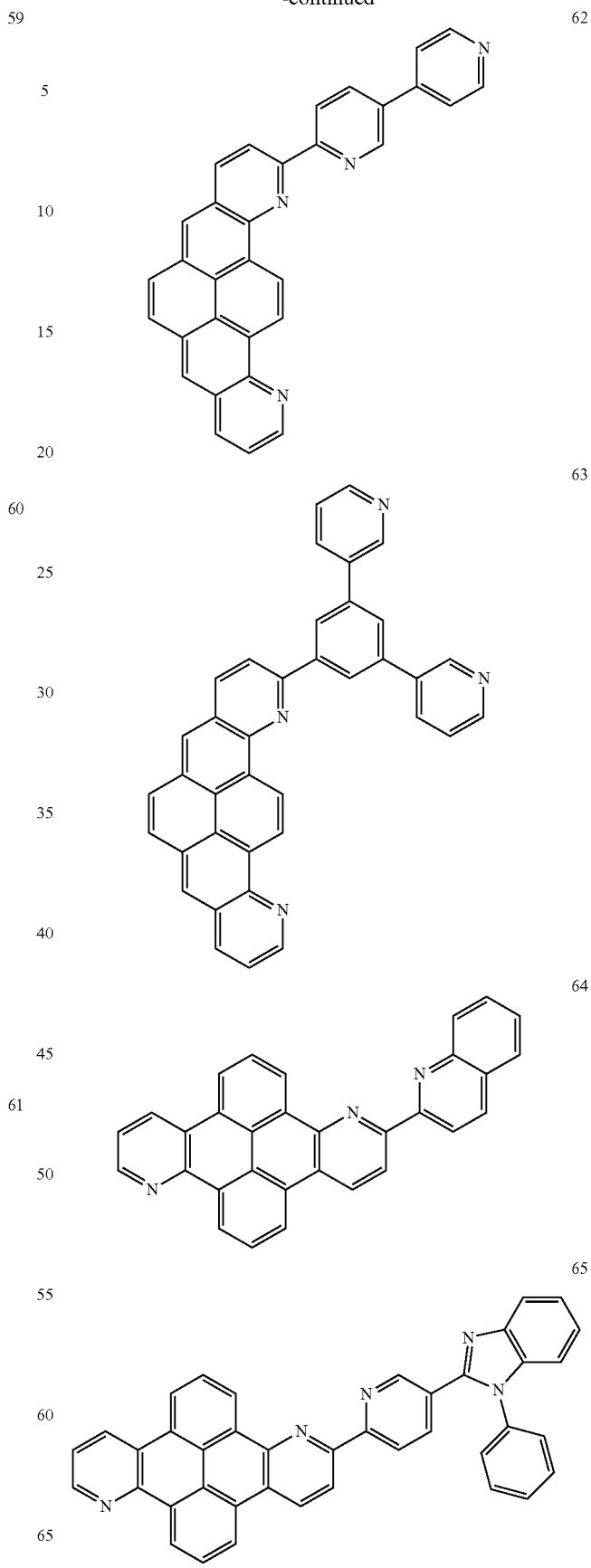

66
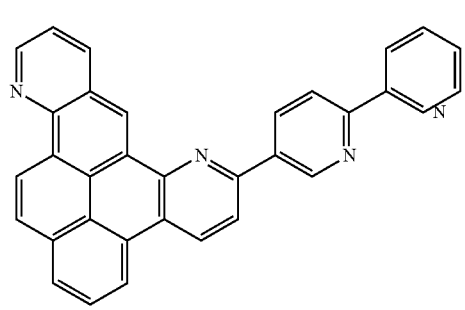
67
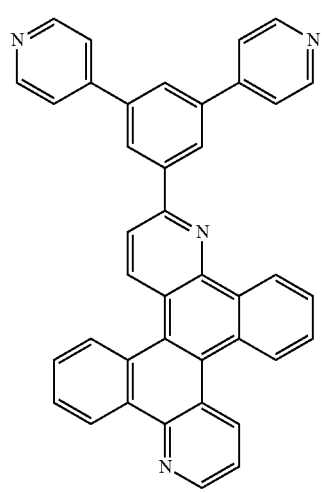
68
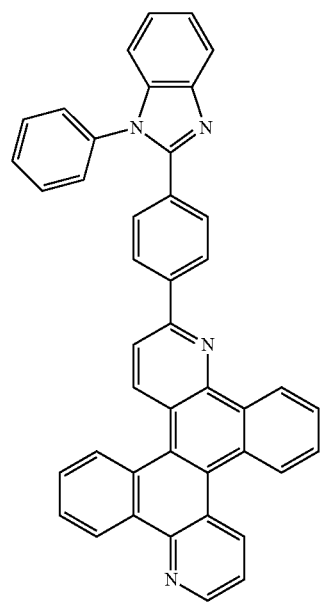
69
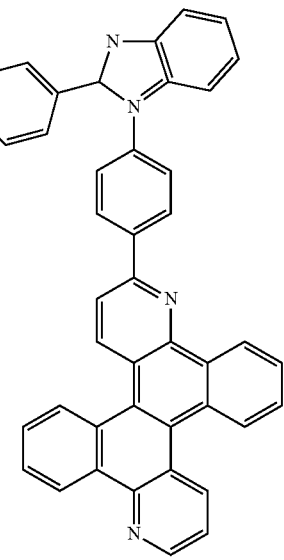
70
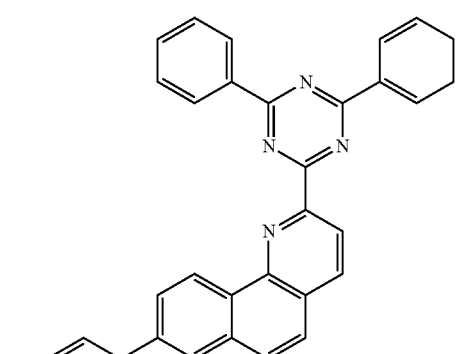
71
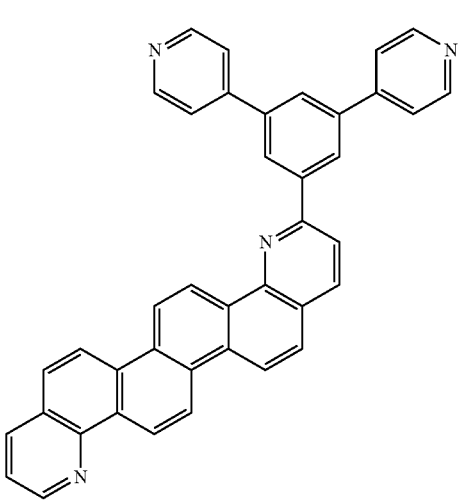

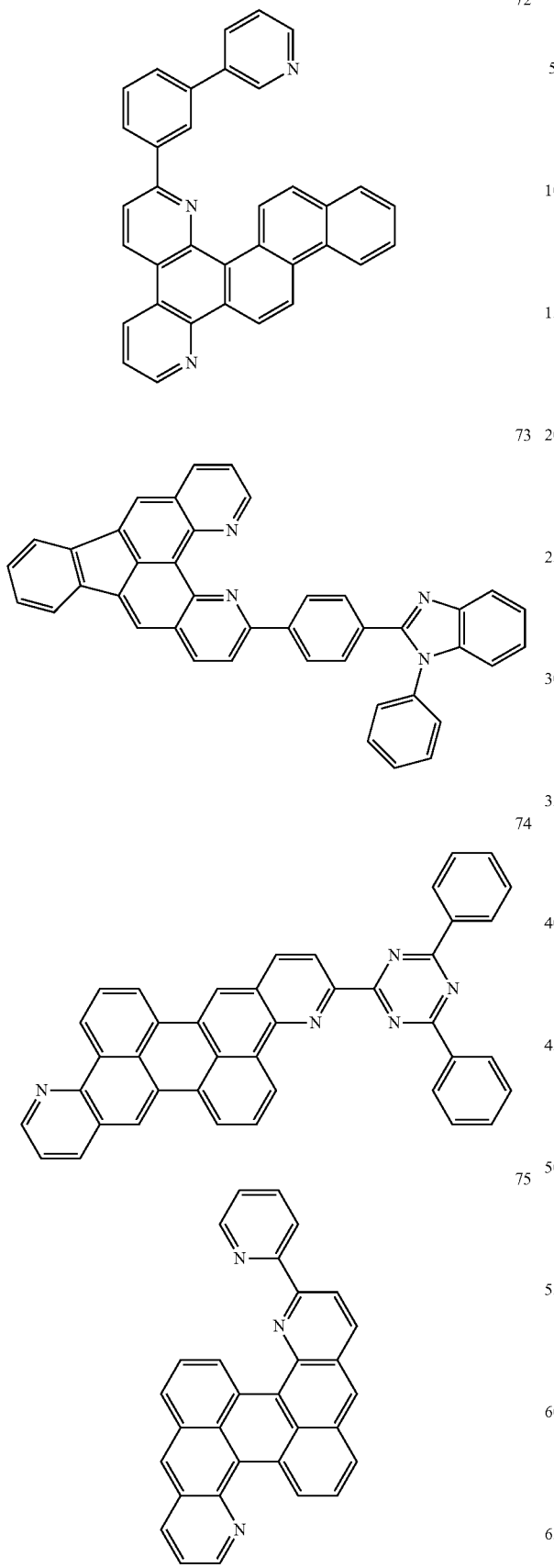
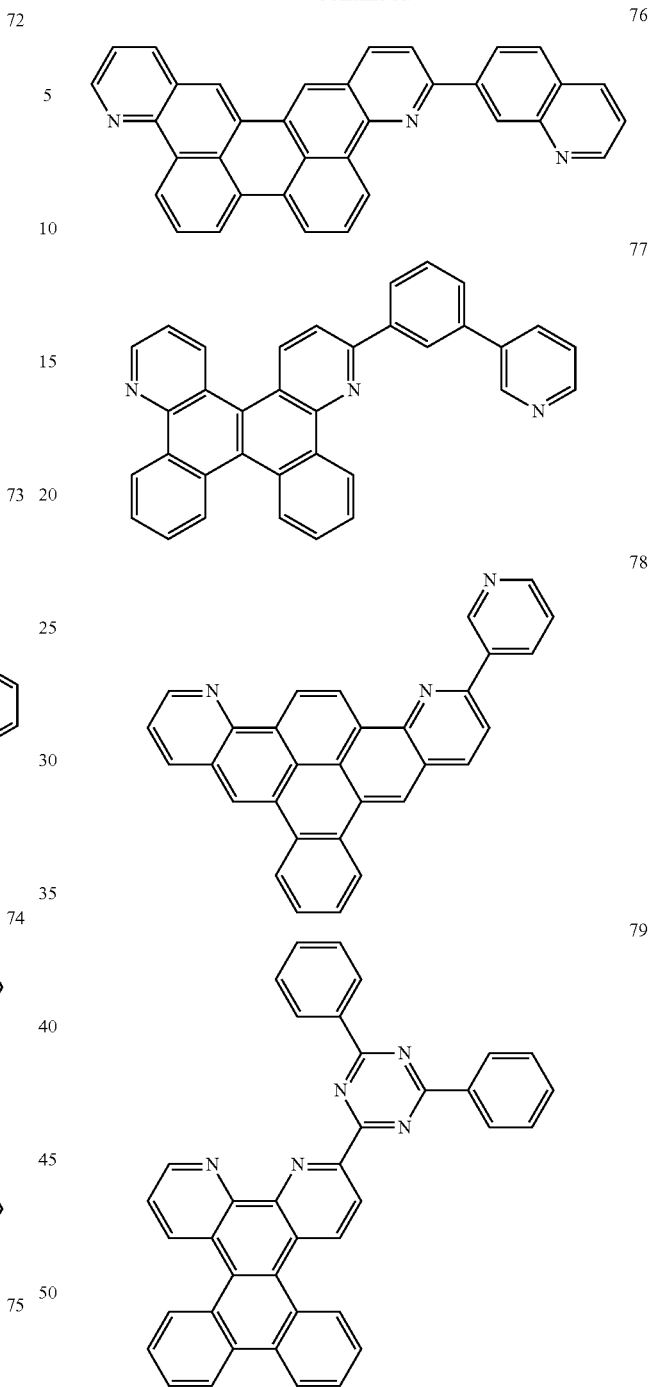

The term "substituted A" in the term "substituted or unsubstituted A (wherein A is an arbitrary substituent)" used herein refers to a case in which one or more hydrogen atoms of the A are substituted with a deuterium atom, a halogen atom, a hydroxyl group, a cyano group, a nitro group, a carboxyl group, a silyl group, or a salt derivative thereof, a sulfonic acid group or a salt derivative thereof, a phosphoric acid group or a salt derivative thereof, a $C_1$-$C_{50}$ alkyl group, a $C_2$-$C_{50}$ alkenyl group, a $C_2$-$C_{50}$ alkynyl group, a $C_1$-$C_{50}$ alkoxy group, a $C_3$-$C_{50}$ cycloalkyl group, a $C_3$-$C_{50}$ cycloalkenyl group, a $C_5$-$C_{60}$ aryl group, a $C_5$-$C_{60}$ aryloxy group, a $C_5$-$C_{60}$ arylthio group, a $C_2$-$C_{60}$ heteroaryl group, a $C_2$-$C_{60}$ fused polycyclic group, a group represented by N($Q_{101}$)($Q_{102}$), or a group represented by Si($Q_{103}$)($Q_{104}$)($Q_{105}$), wherein $Q_{101}$ to $Q_{105}$ may be each independently a hydrogen atom, a deuterium atom, a halogen atom, a hydroxyl group, a cyano group, an amino group, a nitro group, a nitrile group, a carboxyl group, a silyl group, a $C_1$-$C_{50}$ alkyl group, a $C_2$-$C_{50}$ alkenyl group, a $C_2$-$C_{50}$ alkynyl group, a $C_1$-$C_{50}$ alkoxy group, a $C_3$-$C_{50}$ cycloalkyl group, a $C_3$-$C_{50}$ cycloalkenyl group, a $C_5$-$C_{60}$ aryl group, a $C_5$-$C_{60}$ aryloxy group, a $C_5$-$C_{60}$ arylthio group, a $C_5$-$C_{60}$ heteroaryl group, or a $C_2$-$C_{60}$ fused polycyclic group.

For example, the term "substituted A" may refer to a case in which one or more hydrogen atoms of the A are substituted with a deuterium atom, a halogen atom, a hydroxyl group, a cyano group, a nitro group, a nitrile group, a carboxyl group, a silyl group, a methyl group, an ethyl group, a propyl group, a butyl group, an isobutyl group, a pentyl group, a phenyl group, a non-phenyl group, a pentalenyl group, an indenyl group, a naphthyl group, a azulenyl group, a heptalenyl group, an indacenyl group, an acenaphthyl group, a fluorenyl group, a spiro-fluorenyl group, a phenalenyl group, a phenanthrenyl group, an anthryl group, a fluorantenyl group, a triphenylenyl group, a pyrenyl group, a chrycenyl group, a naphthacenyl group, a pycenyl group, a perylenyl group, a pentaphenyl group, a hexacenyl group, a pyrrolyl group, an imidazolyl group, a benzoimidazolyl group, a phenylbenzoimidazolyl group, a pyrazolyl group, a pyridinyl group, a phenylpyridinyl group, a phenylimidazopyridinyl group, a pyrazinyl group, a pyrimidinyl group, a phenylimidazopyrimidinyl group, a pyridazinyl group, an indolyl group, an isoindolyl group, an indazolyl group, a purinyl group, a quinolinyl group, a benzoquinolinyl group, a phthallazinyl group, a naphthyridinyl group, a quinoxalinyl group, a quinazolinyl group, a cynolinyl group, a carbazolyl group, a phenanthridinyl group, an acridinyl group, a phenanthrolinyl group, a phenazinyl group, a puranyl group, a benzopuranyl group, a dibenzopuranyl group, a thiophenyl group, a benzo[b]thiophenyl group, a dibenzothiophenyl group, a thiazolyl group, an isothiazolyl group, a benzothiazolyl group, an oxazolyl group, an isoxazolyl group, a benzooxazolyl group, an isoxazolylatriazolyl group, a phenyltriazolyl group, a tetrazolyl group, an oxadiazolyl group, a phenyloxadiazolyl group, a triazinyl group, a phenyltriazinyl group, a group represented by N($Q_{101}$)($Q_{102}$), or a group represented by Si($Q_{103}$)($Q_{104}$)($Q_{105}$), wherein $Q_{101}$ to $Q_{105}$ may be each independently a hydrogen atom, a deuterium atom, a halogen atom, a hydroxyl group, a cyano group, an amino group, a nitro group, a nitrile group, a carboxyl group, a silyl group, a $C_1$-$C_{50}$ alkyl group, a $C_2$-$C_{50}$ alkenyl group, a $C_2$-$C_{50}$ alkynyl group, a $C_1$-$C_{50}$ alkoxy group, a $C_3$-$C_{50}$ cycloalkyl group, a $C_3$-$C_{50}$ cycloalkenyl group, a $C_5$-$C_{60}$ aryl group, a $C_5$-$C_{60}$ aryloxy group, a $C_5$-$C_{60}$ arylthio group, a $C_5$-$C_{60}$ heteroaryl group, or a $C_2$-$C_{60}$ fused polycyclic group.

The unsubstituted $C_1$-$C_{50}$ alkyl group may refer to a linear or branched saturated hydrocarbonyl group of alkane from which one hydrogen atom is deficient. Examples of the unsubstituted $C_1$-$C_{50}$ alkyl group may be methyl, ethyl, propyl, isobutyl, sec-butyl, pentyl, iso-amyl, hexyl, etc. A substituent of the substituted $C_1$-$C_{50}$ alkyl group may be any one of the substituents presented above where the term "substituted A" is described in detail.

The unsubstituted $C_2$-$C_{50}$ alkenyl group used herein may refer to a terminal group having at least one carbon-carbon double blond at the center or at a terminal of the substituted and unsubstituted $C_2$-$C_{50}$ alkyl group. Non-limiting examples of the unsubstituted $C_2$-$C_{50}$ alkenyl group may be an ethenyl group, a propenyl group, a butenyl group, a pentenyl group, a hexenyl group, a heptenyl group, an octenyl group, a propadienyl group, an isoprenyl group, and an allyl group. A substituent of the substituted $C_2$-$C_{50}$ alkenyl group may be any one of the substituents presented above where the term "substituted A" is described in detail.

The unsubstituted $C_2$-$C_{50}$ alkynyl group used herein may refer to a terminal group having at least one carbon-carbon triple bond at the center or at a terminal of the substituted and unsubstituted $C_2$-$C_{50}$ alkyl group. Non-limiting examples of the unsubstituted $C_2$-$C_{50}$ alkynyl group may be acetylenyl group, etc. A substituent of the substituted $C_2$-$C_{50}$ alkynyl group may be any one of the substituents presented above where the term "substituted A" is described in detail.

The unsubstituted $C_1$-$C_{50}$ alkoxy group used herein may have a formula represented by —OY wherein Y is the unsubstituted $C_1$-$C_{50}$ alkyl group as defined above. Non-limiting examples of the unsubstituted $C_1$-$C_{50}$ alkoxy group may be methoxy, ethoxy, isopropyloxy, butoxy, pentoxy, etc. A substituent of the substituted $C_1$-$C_{50}$ alkoxy group may be any one of the substituents presented above where the term "substituted A" is described in detail.

The unsubstituted $C_3$-$C_{50}$ cycloalkyl group used herein may refer to a cyclic saturated hydrocarbonyl group. Non-limiting examples of the unsubstituted $C_3$-$C_{50}$ cycloalkyl group may be cyclopropyl group, cyclobutyl group, cyclopentyl group, cyclohexyl group, cyclooctyl group, etc. A substituent of the substituted $C_3$-$C_{50}$ cycloalkyl group may be any one of the substituents presented above where the term "substituted A" is described in detail.

The unsubstituted $C_3$-$C_{50}$ cycloalkenyl group used herein may refer to a cyclic unsaturated hydrocarbonyl group having one or more carbon double bonds that are not an aromatic ring. Non-limiting examples of the unsubstituted $C_3$-$C_{50}$ cycloalkenyl group may be a cyclopropenyl group, a cyclobutenyl group, a cyclopentenyl group, a cyclohexenyl group, a cycloheptenyl group, a 1,3-cyclohexadienyl group, a 1,4-cyclohexadienyl group, a 2,4-cycloheptadienyl group, a 1,5-cyclooctadienyl group, etc. A substituent of the substituted $C_3$-$C_{50}$ cycloalkenyl group may be any one of the substituents presented above where the term "substituted A" is described in detail.

The unsubstituted $C_5$-$C_{60}$ aryl group used herein may refer to a monovalent group having a carbocyclic aromatic system in which the number of carbon atoms is 5 to 60, and may be a monocyclic group or a polycyclic group. If the unsubstituted $C_5$-$C_{60}$ aryl group is a polycyclic group, two or more rings contained in the unsubstituted $C_5$-$C_{60}$ aryl group may be fused. Non-limiting examples of the unsubstituted $C_5$-$C_{60}$ aryl group may be a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group, a picenyl group, a perylenyl group, a pentaphenyl, and a hexacenyl. A substituent of the substituted $C_5$-$C_{60}$ aryl group may be any one of the substituents presented above where the term "substituted A" is described in detail.

The unsubstituted $C_5$-$C_{60}$ aryloxy group used herein may refer to a monovalent group wherein a carbon atom of the $C_5$-$C_{60}$ aryl group is attached via an oxygen linker (—O—). A substituent of the substituted $C_5$-$C_{60}$ aryloxy group may be any one of the substituents presented above where the term "substituted A" is described in detail.

The unsubstituted $C_5$-$C_{60}$ arylthio group used herein may refer to a monovalent group wherein a carbon atom of the $C_5$-$C_{60}$ aryl group is attached via a sulfur linker (—S—).

Examples of the unsubstituted $C_5$-$C_{60}$ arylthio group may be a phenylthio group, a naphthylthio group, an indanylthio group, and an indenylthio group. A substituent of the substituted $C_5$-$C_{60}$ arylthio group may be any one of the substituents presented above where the term "substituted A" is described in detail.

The unsubstituted $C_2$-$C_{60}$ heteroaryl group used herein may refer to a monovalent group that has at least one ring having one or more heteroatoms selected from the group consisting of nitrogen (N), oxygen (O), phosphorous (P), and sulfur (S) and that has 2 to 60 carbon atoms, and may be a monocyclic or polycyclic group. If the unsubstituted $C_1$-$C_{60}$ heteroaryl group is a polycyclic group, two or more rings contained in the unsubstituted $C_2$-$C_{60}$ heteroaryl group may be fused. Examples of the unsubstituted $C_2$-$C_{60}$ heteroaryl group may be a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, etc. A substituent of the substituted $C_2$-$C_{60}$ heteroaryl group may be any one of the substituents presented above where the term "substituted A" is described in detail.

The unsubstituted $C_2$-$C_{60}$ fused polycyclic group used herein may refer to a monovalent group that includes two or more fused rings and 2 to 60 carbon atoms. The unsubstituted $C_2$-$C_{60}$ fused polycyclic group may be a polycyclic group, or the like. A substituent of the substituted $C_2$-$C_{60}$ fused polycyclic group may be any one of the substituents presented above where the term "substituted A" is described in detail.

The unsubstituted $C_1$-$C_{50}$ alkylene group used herein may be a linear or branched divalent group of alkane from which two hydrogen atoms are deficient. Examples of the unsubstituted $C_1$-$C_{50}$ alkylene group may be understood by referring to the examples of the unsubstituted $C_1$-$C_{50}$ alkyl group presented above. A substituent of the substituted $C_1$-$C_{50}$ alkylene group may be any one of the substituents presented above where the term "substituted A" is described in detail.

The unsubstituted $C_5$-$C_{60}$ arylene group used herein may refer to a divalent group having a carbocyclic aromatic system having 5 to 60 carbon atoms, and the divalent group may be a monocyclic or polycyclic group. Examples of the unsubstituted $C_5$-$C_{60}$ arylene group may be understood by referring to the examples of the unsubstituted $C_5$-$C_{60}$ aryl group. A substituent of the substituted $C_5$-$C_{60}$ arylene group may be any one of the substituents presented above where the term "substituted A" is described in detail.

The unsubstituted $C_5$-$C_{60}$ aryleneoxy group may refer to a divalent group wherein a carbon atom of the $C_5$-$C_{60}$ arylene group is attached via an oxygen linker (—O—). A substituent of the substituted $C_5$-$C_{60}$ aryleneoxy group may be any one of the substituents presented above where the term "substituted A" is described in detail.

The unsubstituted $C_5$-$C_{60}$ arylenethio group may refer to a divalent group wherein a carbon atom of the $C_5$-$C_{60}$ arylene is attached via a sulfur linker (—S—). A substituent of the substitute $C_5$-$C_{60}$ arylenethio group may be any one of the substituents presented above where the term "substituted A" is described in detail.

The unsubstituted $C_2$-$C_{60}$ heteroarylene group used herein may refer to a divalent group that has at least one ring having one or more heteroatoms selected from the group consisting of nitrogen (N), oxygen (O), phosphorous (P), and sulfur (S) and that has 2 to 60 carbon atoms, and may be a monocyclic or polycyclic group. If the unsubstituted $C_2$-$C_{60}$ heteroaryl group is a polycyclic group, two or more rings contained in the unsubstituted $C_2$-$C_{60}$ heteroaryl group may be fused. Examples of the unsubstituted $C_2$-$C_{60}$ heteroarylene group may be understood by referring to the examples of the unsubstituted $C_2$-$C_{60}$ heteroaryl group. A substituent of the substituted $C_2$-$C_{60}$ heteroarylene group may be any one of the substituents presented above where the term "substituted A" is described in detail.

The heterocyclic compound represented by Formula 1 may be synthesized by using known organic synthesis methods. The organic synthesis methods of the heterocyclic compound may be obvious to one of ordinary skill in the art with reference to examples, one of which will now be described in detail.

The heterocyclic compound represented by Formula 1 may be used in an organic layer interposed between a pair of electrodes of an organic light-emitting diode.

The heterocyclic compound represented by Formula 1 has excellent luminous characteristics and a charge transporting capability. Due to such features, the heterocyclic compound of Formula 1 is useful as an electron injection material or an electron transport material which are suitable for various colors, for example, red, green, blue, and white fluorescent and phosphorescent devices, and also useful as an light-emitting material that is suitable for green, blue, and white fluorescent devices. If the heterocyclic compound of Formula 1 is used, an organic light-emitting diode having high efficiency, low voltage, high brightness, and long lifetime may be obtainable.

Another aspect of the present invention provides an organic light-emitting diode including a first electrode; a second electrode disposed facing the first electrode; and an organic layer interposed between the first electrode and the second electrode, wherein the heterocyclic compound represented by Formula 1 may be used alone, or may be used in a mixed form with other materials.

The term "organic layer" used herein refers to a single or a multi-layer interposed between the first electrode and the second electrode.

The organic layer may include at least one layer selected from a hole injection layer, a hole transport layer, a functional layer having a hole injection capability and a hole transport capability, an electron blocking layer, an emission layer, a hole blocking layer, an electron transport layer, an electron injection layer, and a functional layer having an electron transport capability and an electron injection capability. Accordingly, the heterocyclic compound represented by Formula 1 may be included in at least one layer selected from a hole injection layer, a hole transport layer, a functional layer having a hole injection capability and a hole transport capability, an electron blocking layer, an emission layer, a hole blocking layer, an electron transport layer, an electron injection layer, and a functional layer having an electron transport capability and an electron injection capability. For example, the heterocyclic compound represented by Formula 1 may be included in an electron transport layer.

The heterocyclic compound represented by Formula 1 may be included alone or in a mixed form with other materials in the organic layer. For example, Compound 11 alone may be included in a single material form in the organic layer, or a combination of Compound 11 and Compound 17 may be included in the organic layer. If the organic layer includes Compound 11 and Compound 17, Compound 11 and Compound 17 may be presented in a mixed form either in one layer (for example, an electron transport layer) in the organic layer or in different layers (for example, Compound 11 may be included in an electron transport layer and Compound 17 may be included in an emission layer) in the organic layer.

The organic layer may include an emission layer and the emission layer may include the heterocyclic compound represented by Formula 1 alone or in a mixed form with other materials.

For example, the organic layer includes an emission layer and the emission layer includes a fluorescent or a phosphorescent host and the fluorescent or the phosphorescent host may include the heterocyclic compound represented by Formula 1. As a phosphorescent dopant, Ir, Pt, Os, Re, Ti, Zr, Hf, or an organometallic complex including a combination thereof may be used. However, the phosphorescent dopant may not be limited thereto. Alternatively, the organic layer includes an emission layer and the emission layer includes a fluorescent dopant and the fluorescent dopant may include the heterocyclic compound represented by Formula 1.

The organic layer may include at least one layer selected from an electron transport layer, an electron injection layer, and a functional layer having an electron transport capability and an electron injection capability and the at least one layer selected from an electron transport layer, an electron injection layer, and a functional layer having an electron transport capability and an electron injection capability may include the heterocyclic compound represented by Formula 1.

The organic layer may include at least one layer selected from an electron transport layer, an electron injection layer, and a functional layer having an electron transport capability and an electron injection capability and the at least one layer selected from an electron transport layer, an electron injection layer, and a functional layer having an electron transport capability and an electron injection capability may include the heterocyclic compound represented by Formula 1 and a metal-containing material. An example of the metal-containing material is a Li complex. Non-limited examples of the Li complex are lithium quinolate (LiQ) and Compound 101 below:

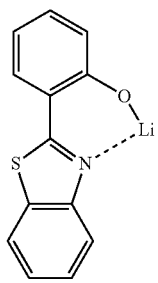

Compound 101

The organic layer includes at least one layer selected from an electron transport layer, an electron injection layer, and a functional layer having an electron transport capability and an electron injection capability; and at least one layer selected from a red emission layer, a green emission layer, a blue emission layer, and a white emission layer, wherein the at least one layer selected from an electron transport layer, an electron injection layer, and a functional layer having an electron transport capability and an electron injection capability includes the heterocyclic compound represented by Formula 1 and the at least one layer selected from a red emission layer, a green emission layer, a blue emission layer, and a white emission layer may include a phosphorescent compound.

At least one layer selected from a hole injection layer, a hole transport layer, a functional layer having a hole injection capability and a hole transport capability, an electron blocking layer, an emission layer, a hole blocking layer, an electron transport layer, an electron injection layer, and a functional layer having an electron transport capability and an electron injection capability in the organic layer may be formed by a deposition process or a wet process.

The term "wet process" used herein refers to a process in which a material is mixed with a solvent to prepare a mixture, and the mixture is provided on a substrate, followed by drying and/or heat treating so as to remove at least a portion of the solvent, thereby forming a film including the material on the substrate.

For example, the organic layer may be formed by using a typical vacuum deposition method. Alternatively, a mixture including the heterocyclic compound and a solvent may be provided on an organic layer formation region (for example, on an upper portion of a hole transport layer) by spin coating, spraying, ink-jet printing, dipping, casting, Gravia coating, bar coating, roll coating, wire bar coating, screen coating, flexo coating, offset coating, or laser transferring, and then, the mixture provided on the organic layer formation region is dried and/or heat treated to remove at least a portion of the solvent, thereby forming the organic layer.

Alternatively, after an organic layer is formed on a base film by using the wet process as described above, the organic layer may be transferred to an organic layer formation region (for example, an upper portion of the hole transport layer) by using, for example, a laser.

FIG. 1 is a schematic sectional view of an organic light-emitting diode 10 according to an embodiment of the present invention. Hereinafter, with reference to FIG. 1, the structure of the organic light-emitting diode 10, and a method of manufacturing the organic light-emitting diode 10, according to an embodiment of the present invention, will be described in detail.

The organic light-emitting diode 10 sequentially includes a substrate 11, a first electrode 12, a hole injection layer 13, a hole transport layer 14, an emission layer 15, an electron transport layer 16, an electron injection layer 17, and a second electrode 18 in this stated order.

The substrate 11 may be any one of various substrates that are used in a known organic light-emitting device. In some embodiments of the present invention, the substrate 11 may be a glass substrate or a transparent plastic substrate with excellent mechanical strength, thermal stability, transparency, surface smoothness, ease of handling, and water repellency.

The first electrode 12 may be formed by providing a first electrode material on the substrate 11 by deposition or sputtering. If the first electrode 12 is an anode, to allow holes to be injected thereinto easily, the first electrode material may be selected from materials having a high work function. Also, the first electrode 12 may be a reflection electrode or a transmission electrode. The first electrode material may be a transparent and highly conductive material, such as an indium tin oxide (ITO), or an indium zinc oxide (IZO), a tin oxide ($SnO_2$), a zinc oxide (ZnO), etc. Alternatively, if magnesium (Mg), aluminum (Al), aluminum-lithium (Al—Li), calcium (Ca), magnesium-indium (Mg—In), magnesium-silver (Mg—Ag), etc, are used as the first electrode material, the first electrode 12 may be formed as a reflection electrode. The first electrode 12 may include two different materials. For example, the first electrode 12 may have a two-layer structure including two different materials. However, the structure of the first electrode 12 is not limited thereto.

The hole injection layer (HIL) 13 is formed on the first electrode 12.

The hole injection layer 13 may be formed on the first electrode 12 by using various methods, such as the vacuum deposition, wet process, laser transferring, etc., as described above.

When the hole injection layer 13 is formed by vacuum deposition, the deposition conditions may vary according to a material that is used to form the hole injection layer 13, and the structure and thermal characteristics of the hole injection layer 13. For example, the deposition conditions may include a deposition temperature of about 100° C. to about 500° C., a vacuum pressure of about $10^{-8}$ torr to about $10^{-3}$ torr, and a deposition rate of about 0.01 Å/sec to about 100 Å/sec. However, the deposition conditions are not limited thereto.

When the hole injection layer 13 is formed using spin coating as a wet process, coating conditions may vary according to a material used to form the hole injection layer 13, and the structure and thermal properties of the hole injection layer 13. For example, a coating speed may be from about 2000 rpm to about 5000 rpm, and a temperature at which a heat treatment is performed to remove a solvent after coating may be from about 80° C. to about 200° C. However, the coating conditions are not limited thereto.

A hole injection layer material may be any one of known hole injecting materials. Non-limiting examples of the hole injection layer material are a phthalocyanine compound, such as copperphthalocyanine, m-MTDATA (a structure thereof is illustrated below), TDATA (a structure thereof is illustrated below), 2-TNATA (a structure thereof is illustrated below), polyaniline/dodecylbenzenesulfonic acid (Pani/DBSA), poly (3,4-ethylenedioxythiophene)/poly(4-styrenesulfonate) (PEDOT/PSS), polyaniline/camphor sulfonic acid (Pani/CSA), polyaniline/poly(4-styrenesulfonate) (Pani/PSS), etc.

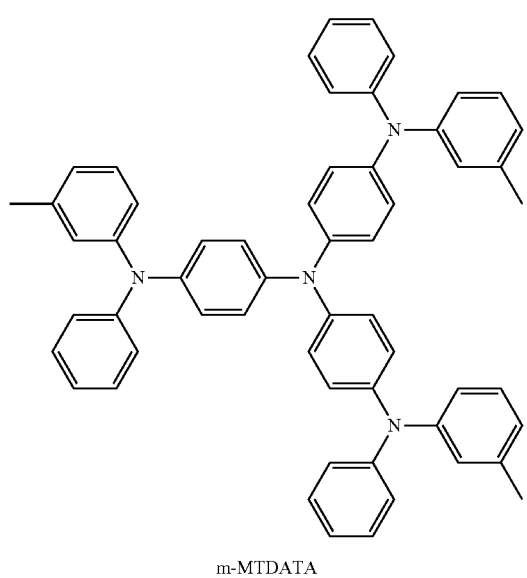

m-MTDATA

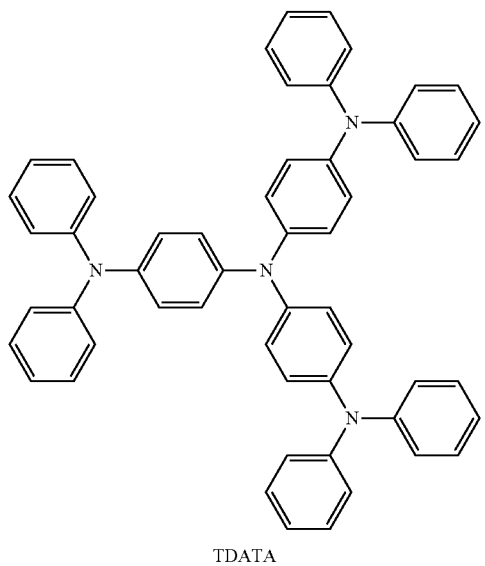

TDATA

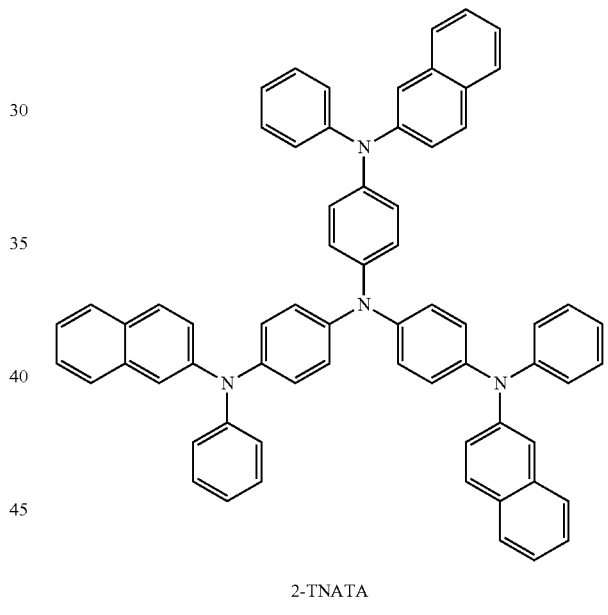

2-TNATA

The hole injection layer 13 may have a thickness of about 100 Å to about 10,000 Å, more preferably, a thickness of about 100 Å to about 1,000 Å. When the thickness of the hole injection layer 13 is within these ranges, the hole injection layer 13 may have satisfactory hole injection characteristics without an increase in driving voltage.

Then, the hole transport layer (HTL) 14 may be formed on the hole injection layer 13 by, for example, the vacuum deposition, wet process, or laser transferring. When the hole transport layer 14 may be formed on the hole injection layer 13 by vacuum deposition or spin coating, the deposition or coating conditions may be similar to those applied to form the hole injection layer 13, although the deposition or coating conditions may vary according to a material that is used to form the hole transport layer 14.

A hole transport layer material may be any one of known hole transport materials. Non-limiting examples of the hole transport layer material are TPD (a structure thereof is illustrated below), NPB (a structure thereof is illustrated below), etc.

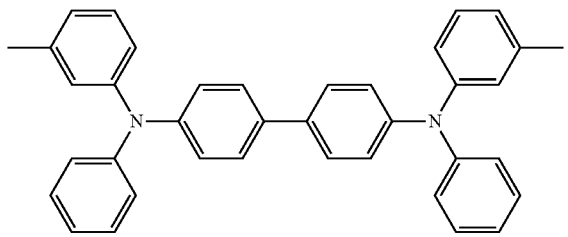

TPD

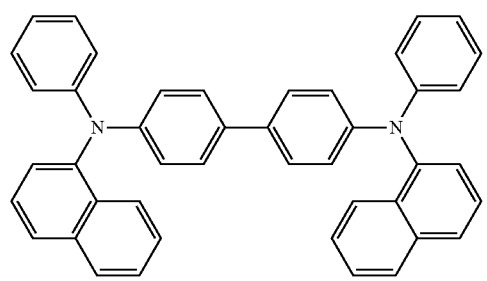

NPB

The hole transport layer 14 may have a thickness of about 50 Å to about 1000 Å, more preferably, a thickness of about 100 Å to about 800 Å. When the thickness of the hole transport layer 14 is within the above ranges, the hole transport layer 14 may have satisfactory hole transport characteristics without an increase in driving voltage.

The emission layer 15 may be formed on the hole transport layer 14 by, for example, the vacuum deposition, wet process, or laser transferring. When the emission layer 15 is formed by vacuum deposition or spin coating, the deposition or coating conditions may be similar to those applied to form the hole injection layer 13, although the deposition or coating conditions may vary according to a material that is used to form the emission layer 15.

The emission layer 15 may include a known phosphorescent host, a fluorescent host, a phosphorescent dopant, or a fluorescent dopant. Also, the emission layer 15 may include the heterocyclic compound of Formula 1. If the heterocyclic compound represented by Formula 1 is included, the heterocyclic compound may function as a phosphorescent host, a fluorescent host, or a fluorescent dopant.

As a known host, 4,4'-N,N'-dicarbazole-biphenyl (CBP), 9,10-di-naphthalene-2-yl-anthracene (AND, a structure thereof is illustrated below), TPBI (a structure thereof is illustrated below), TBADN (a structure thereof is illustrated below), E3 (a structure thereof is illustrated below), etc. may be used, but are not limited thereto.

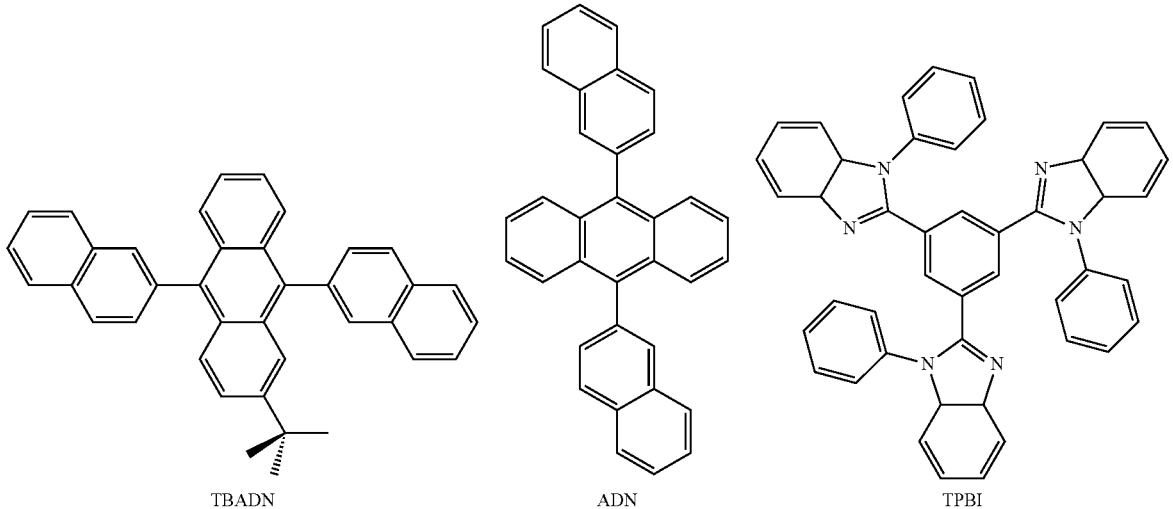

TBADN  ADN  TPBI

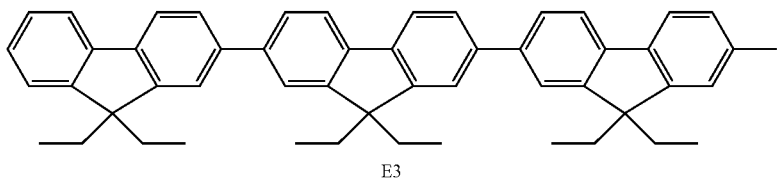

E3

As a red dopant, PtOEP (a structure thereof is illustrated below), Ir(piq)₃ (a structure thereof is illustrated below), Btp₂Ir(acac) (a structure thereof is illustrated below), etc. may be used, but are not limited thereto.

ture thereof is illustrated below), Ir(mpyp)₃ (a structure thereof is illustrated below), etc. may be used, but are not limited thereto.

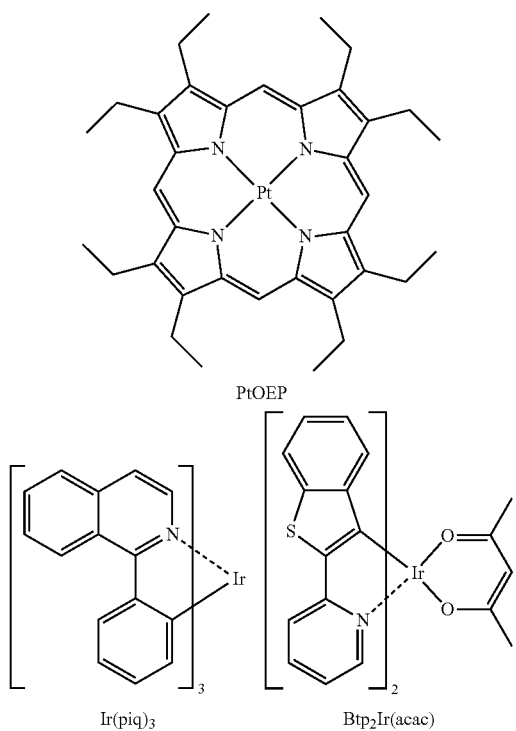

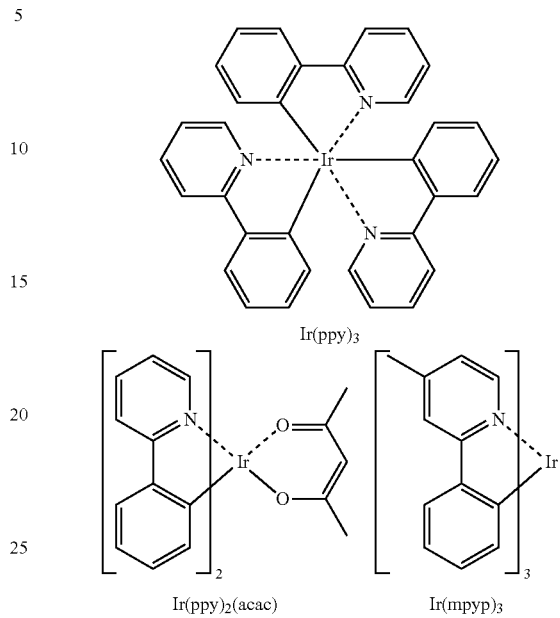

Also, as a green dopant, Ir(ppy)₃ (ppy=phenyl pyridine, a structure thereof is illustrated below), Ir(ppy)₂(acac) (a struc- As a blue dopant, F₂Irpic (a structure thereof is illustrated below), (F₂ppy)₂Ir(tmd) (a structure thereof is illustrated below), Ir(dfppz)₃ (a structure thereof is illustrated below), DPVBi (a structure thereof is illustrated below), 4,4'-bis(4-diphenyl aminostaryl)biphenyl (DPAVBi, a structure thereof is illustrated below), 2,5,8,11-tetra-tert-butyl perylene (TBPe, a structure thereof is illustrated below), etc. may be used, but are not limited thereto.

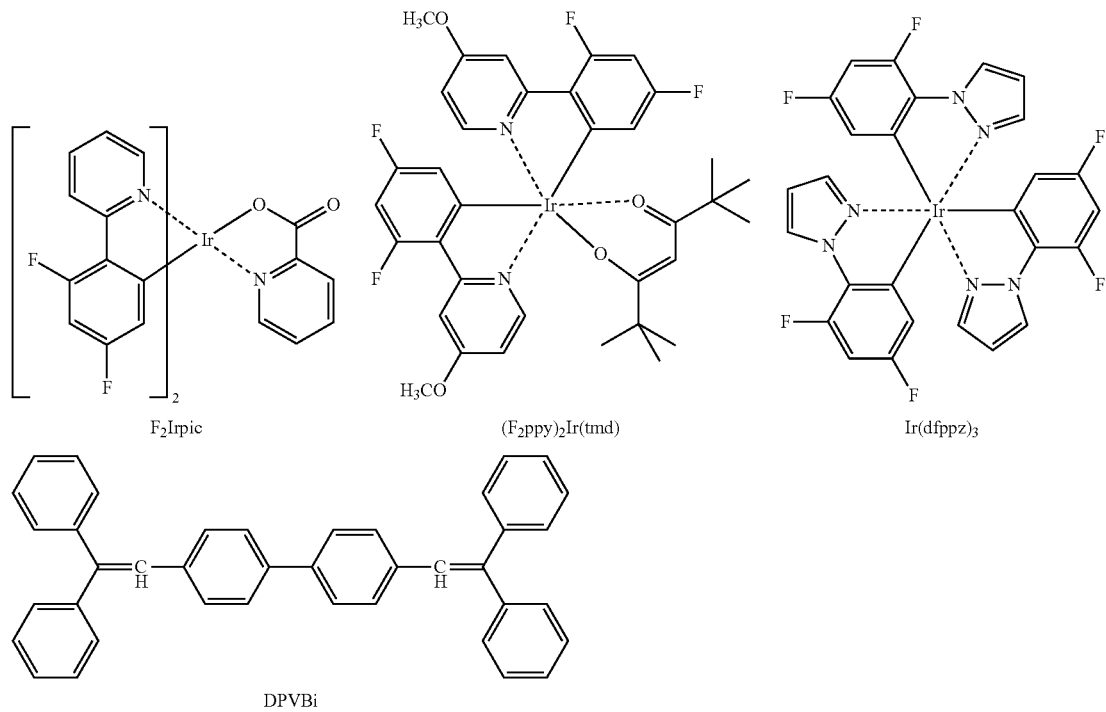

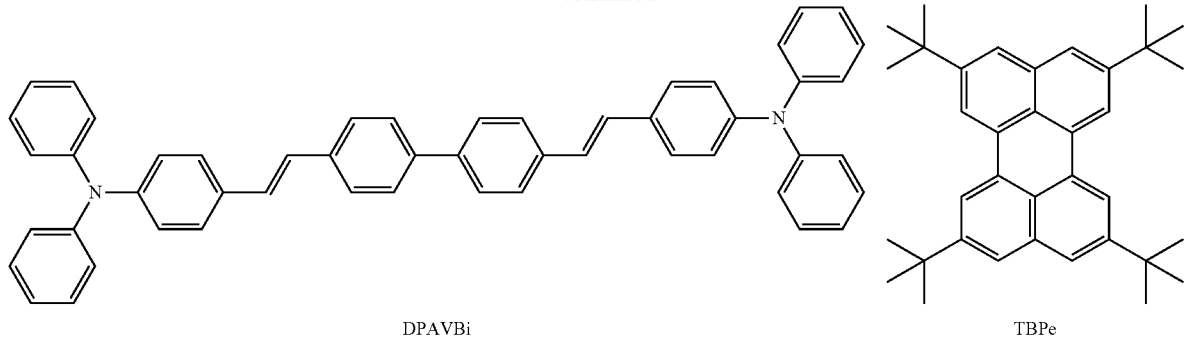

DPAVBi

TBPe

If the emission layer 15 includes a host and a dopant, the amount of the dopant may be from about 0.01 to about 15 parts by weight based on 100 parts by weight of the host, but are not limited thereto.

A thickness of the emission layer 15 may be from about 100 Å to about 1000 Å, more preferably, about 200 Å to about 600 Å. If the thickness of the emission layer 15 is within these ranges, excellent luminescence characteristics may be obtained without a substantial increase in driving voltage.

If the emission layer 15 includes a phosphorescent dopant, to prevent diffusion of a triple exciton or a hole into the electron transport layer 16, a hole blocking layer (HBL, not shown in FIG. 1) may be formed between the electron transport layer 16 and the emission layer 15 by vacuum deposition, wet process, or laser transferring. If the HBL is formed by vacuum deposition or spin coating, the deposition or coating conditions may be similar to those applied to form the hole injection layer 13, although the deposition or coating conditions may vary according to a material that is used to form the HBL. As a HBL material, any one of known hole blocking materials may be used, and examples thereof are an oxadiazole derivative, a triazole derivative, a phenanthroline derivative, etc.

A thickness of the HBL may be from about 50 Å to about 1000 Å, more preferably, about 100 Å to about 300 Å. If the thickness of the HBL is within the ranges described above, excellent hole blocking characteristics may be obtained without a substantial increase in driving voltage.

Then, the electron transport layer 16 may be formed by using various methods, such as the vacuum deposition, wet process, laser transferring, etc., as described above. The electron transport layer 16 may include the heterocyclic compound represented by Formula 1. Alternatively, the electron transport layer 16 may include either a known electron transport material alone, or a known electron transport material and the heterocyclic compound represented by Formula 1. Non-limiting examples of the known electron transport material are a quinoline derivative, such as tris(8-quinolinolate) aluminum ($Alq_3$), TAZ (a structure thereof is illustrated below), BAlq (a structure thereof is illustrated below), and beryllium bis(benzoquinolin-10-olate ($Bebq_2$).

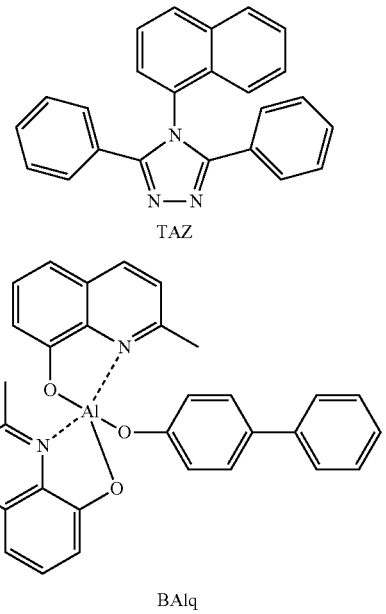

TAZ

BAlq

The electron transport layer 16 may include an electron transportable organic compound. Non-limiting examples of the electron transportable organic compound are 9,10-di (naphthalene-2-yl)anthracene (AND); and anthracene-based compounds, such as compounds 301 and 302 below.

Compound 301

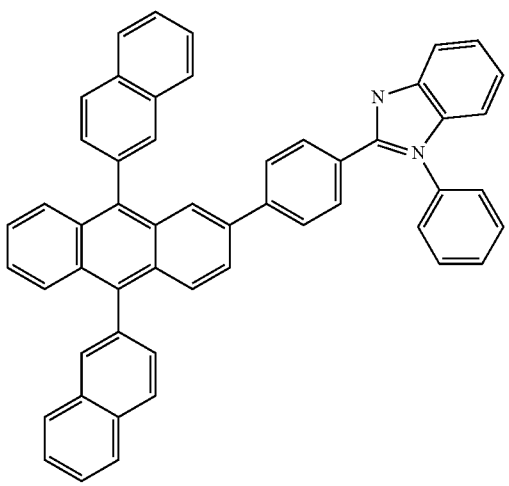

Compound 302

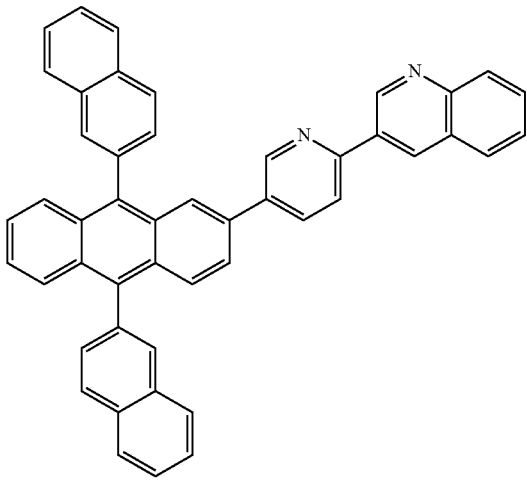

A thickness of the electron transport layer 16 may be from about 100 Å to about 1000 Å, more preferably, about 150 Å to about 500 Å. If the thickness of the electron transport layer 16 is within the ranges described above, excellent electron transporting characteristics may be obtained without a substantial increase in driving voltage.

If the electron transport layer 16 is formed by vacuum deposition or spin coating, the deposition or coating conditions may be similar to those applied to form the hole injection layer 13, although the deposition or coating conditions may vary according to a material that is used to form the electron transport layer 16.

The electron injection layer 17 may be deposited on the electron transport layer 16 by using a material that allows electrons to be easily injected from an anode. As a material for forming the electron injection layer 17, any known electron injection layer material, such as LiF, NaCl, CsF, $Li_2O$, or BaO, may be used. Alternatively, the heterocyclic compound of Formula 1 may also be used. The deposition conditions of the electron injection layer 17 may be similar to those applied to form the hole injection layer 13, although the deposition or coating conditions may vary according to a material that is used to form the electron injection layer 17.

A thickness of the electron injection layer 17 may be from about 1 Å to about 100 Å, more preferably, about 3 Å to about 90 Å. If the thickness of the electron injection layer 17 is within the ranges described above, excellent electron injection characteristics may be obtained without a substantial increase in driving voltage.

The second electrode 18 is formed as a reflection electrode on the electron injection layer 17. The second electrode 18 may be a cathode as an electron injection electrode, and in this case, a low work function metal, alloy, electrically conductive compound, and a mixture thereof may be used as a second electrode metal. In detail, lithium (Li), magnesium (Mg), aluminum (Al), aluminum-lithium (Al—Li), calcium (Ca), magnesium-indium (Mg—In), magnesium-silver (Mg—Ag), etc. may be formed as a thin film for use as a reflection electrode. Also, if the organic light-emitting diode is used in a top-emission light-emitting device, a transmission electrode may be formed using ITO or IZO.

The organic light-emitting diode may be included in a flat display device including a transistor. Accordingly, another aspect of the present invention provides a transistor including a source, a drain, a gate, and an active layer and an organic light-emitting diode including an organic layer that includes the heterocyclic compound represented by Formula 1, wherein the first electrode of the organic light-emitting diode is electrically connected to any one of the source and the drain.

The active layer of the transistor may be an amorphous silicon layer, a crystalloid silicon layer, an organic semiconductor layer, or an oxide semiconductor layer, and is not limited thereto.

Hereinafter, an organic light-emitting diode according to an embodiment of the present invention will be described in detail with reference to Synthesis Examples and Examples. However, the present invention is not limited to Synthesis Example, and Example below.

SYNTHESIS EXAMPLE 1

Synthesis of Compound 11

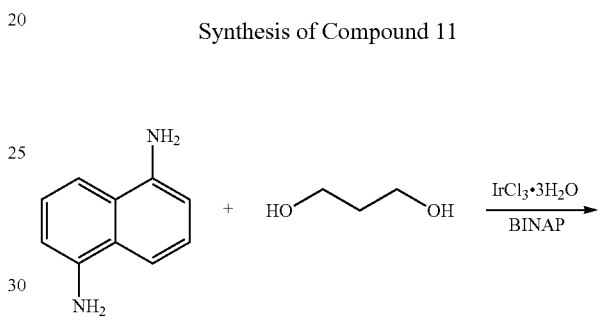

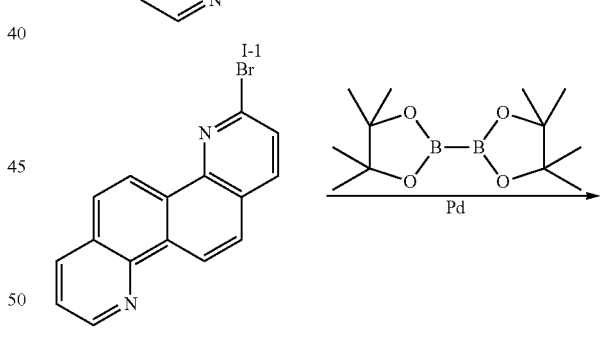

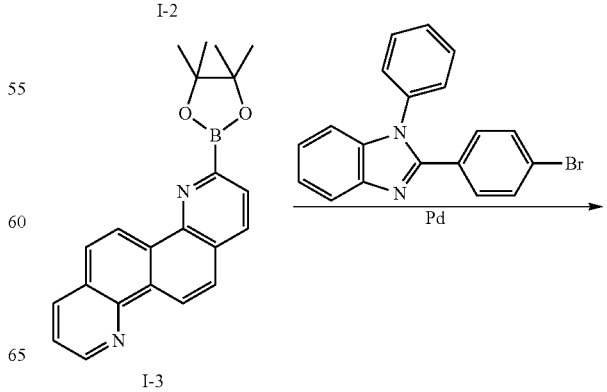

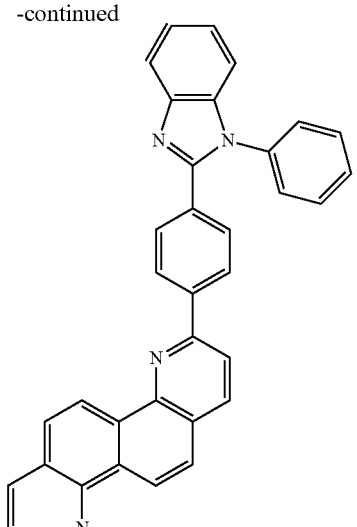

11

Synthesis of Intermediate I-1

1.58 g (10.0 mmol) of naphthalene-1,5-diamine and 0.30 g (4.0 mmol) of 1,3-propandiol were dissolved in 10 ml of mesitylene. Then; a mixture including 140 mg (0.40 mmol) of $IrCl_3 \cdot H_2O$, 372 mg (0.60 mmol) of BINAP, and 68 mg (0.64 mmol) of sodium carbonate was added thereto. The resultant mixture was stirred at a temperature of 169° C. for 15 hours. After a reaction finished, a solvent was evaporated and the residue was separation-purified by silicagel column chromatography to obtain Intermediate I-1 1.65 g (Yield: 72%). The formed compound was identified by mass spectroscopy/fast atom bombardment (MS/FAB). $C_{16}H_{10}N_2$: calc. 230.08, found 230.15

Synthesis of Intermediate I-2

In a nitrogen atmosphere, 2.30 g (10.0 mmol) of Intermediate I-1 was dissolved in 20 ml of dimethylaminoethanol and the temperature was decreased to −78° C., followed by gradual dropwise adding of 11.4 ml (1.6M in hexane) of n-butyllithium thereto. After the adding, the temperature was increased to 0° C. and then the mixture was stirred for 2 hours. At a temperature of 0° C. 1.75 g of bromine ($Br_2$) was added thereto and stirred for 2 hours, followed by stirring at room temperature for 24 hours. After the reaction finished, the resultant mixture was neutralized with a sodium thiosulfate aqueous solution, followed by extraction three times with 30 ml of ethylacetate and 30 ml of water. A collected organic layer was dried with a magnesium sulfate and the residual obtained by evaporating a solvent was separation-purified by silicagel column chromatography to obtain 2.31 g (Yield: 75%) of Intermediate I-2. The formed compound was identified by MS/FAB. $C_{16}H_9BrN_2$: calc. 307.99, found 308.08

Synthesis of Intermediate I-3

3.09 g (10.0 mmol) of Intermediate I-2, 2.54 g (10.0 mmol) of bis(pinacolato)diborane, 0.36 g (0.5 mmol) of [1,1'-bis(diphenylphosphino) ferrocene]dichloro palladium (II) (hereinafter referred to as $PdCl_2(dppf_2)$, and 2.94 g (30.0 mmol) of KOAc were dissolved in 40 ml of DMSO and stirred at a temperature of 80° C. for 6 hours. The reaction solution was cooled to room temperature, followed by extraction three times with 50 ml of water and 50 ml of diethylether. A collected organic layer was dried with a magnesium sulfate and the residual obtained by evaporating a solvent was separation-purified by silicagel column chromatography to obtain 2.84 g (Yield: 80%) of Intermediate I-3. The formed compound was identified by MS/FAB. $C_{22}H_{21}BN_2O_2$: calc. 356.16, found 356.24

Synthesis of Compound 11

3.56 g (10.0 mmol) of Intermediate I-3, 4.19 g (12.0 mmol) of 2-(4-bromophenyl)-1-phenyl-1-benzoimidazole, 0.577 g (0.5 mmol) of $Pd(PPh_3)_4$(tetrakis(triphenylphosphine)palladium), and 4.15 g (30.0 mmol) of $K_2CO_3$ were dissolved in 40 ml of a $THF/H_2O$ (2/1 volumetric ratio) mixed solution, and then the mixture was stirred at a temperature of 70° C. for 5 hours. The reaction solution was cooled to room temperature and 30 ml of water was added thereto, followed by extraction three times with ethylether. A collected organic layer was dried with a magnesium sulfate and the residual obtained by evaporating a solvent was separation-purified by silicagel column chromatography to obtain compound 11 3.78 g (Yield: 76%). The formed compound was identified by MS/FAB and $^1$H NMR. $C_{35}H_{22}N_4$ calc. 498.18, found 498.25.

$^1$H NMR ($CDCl_3$, 400 MHz) δ(ppm) 8.97-8.94 (m, 3H), 8.45 (d, 1H), 8.21-8.14 (m, 4H), 8.10-8.08 (m, 1H), 8.03 (d, 1H), 7.94 (d, 1H), 7.86 (d, 1H), 7.80-7.78 (m, 1H), 7.66-7.64 (m, 1H), 7.58-7.55 (m, 2H), 7.51-7.48 (m, 1H), 7.44-7.35 (m, 3H), 7.32-7.28 (m, 1H), 7.24-7.21 (m, 1H).

SYNTHESIS EXAMPLE 2

Synthesis of Compound 17

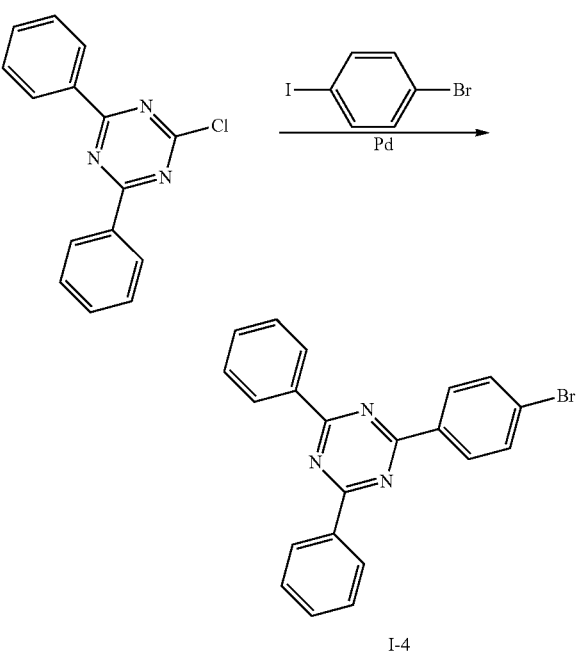

I-4

Synthesis of Intermediate I-4

2.68 g (10 mmol) of 2-chloro-4,6-diphenyl-[1,3,5]-triazine, 4.24 g (15.0 mmol) of 1-bromo-4-iodobenzene, 0.58 g (0.5 mmol) of Pd(PPh$_3$)$_4$, and 4.14 g (30.0 mmol) of K$_2$CO$_3$ were dissolved in 60 ml of a THF/H$_2$O (2/1) mixed solution and then stirred at a temperature of 70° C. for 5 hours. The reaction solution was cooled to room temperature, followed by extraction three times with 60 mL of water and 60 mL of diethylether. A collected organic layer was dried with a magnesium sulfate and the residual obtained by evaporating a solvent was separation-purified by silicagel column chromatography to obtain 2.56 g (Yield: 66%) of Intermediate I-4. The formed compound was identified by MS/FAB. C$_{21}$H$_{14}$BrN$_3$ calc. 387.03, found 387.11.

Synthesis of Compound 17

Compound 17 was obtained by using the same method as used to synthesize Compound 11 except that Intermediate I-4 was used instead of 2-(4-bromophenyl)-1-phenyl-1-benzoimidazole. The formed compound was identified by MS/FAB and $^1$H NMR. C$_{37}$H$_{23}$N$_5$: calc. 537.19, found 537.24.

$^1$H NMR (CDCl$_3$, 400 MHz) δ(ppm) 8.96-8.94 (m, 3H), 8.81-8.78 (m, 4H), 8.60-8.57 (m, 2H), 8.49-8.44 (d, 3H), 8.10-8.08 (m, 1H), 8.03 (d, 1H), 7.94 (d, 1H), 7.86 (d, 1H), 7.63-7.59 (m, 4H), 7.51-7.48 (m, 1H), 7.42-7.38 (m, 2H).

SYNTHESIS EXAMPLE 3

Synthesis of Compound 25

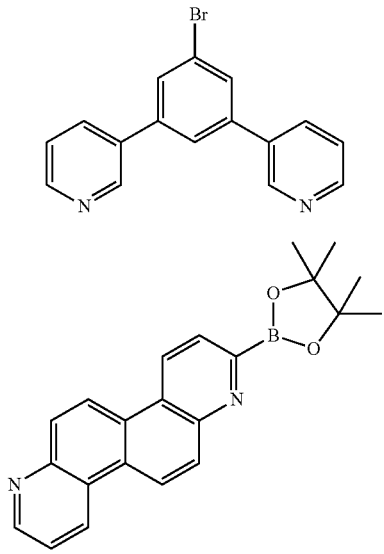

Synthesis of Intermediate I-5

Intermediate I-5 was obtained by using the same method as used to synthesize Compound 11 except that 1,3,5-tribromobenzene was used instead of 2-(4-bromophenyl)-1-phenyl-1-benzoimidazole and 3-pyridinylboric acid was used instead of Intermediate I-3. The formed compound was identified by MS/FAB. C$_{16}$H$_{11}$BrN$_2$: calc. 310.01, found 310.11

Synthesis of Intermediate I-6

Intermediate I-6 was obtained by using the same method as used to synthesize Intermediate I-3, except that naphthalene-2,6-diamine was used instead of naphthalene-1,5-diamine. The formed compound was identified by MS/FAB. C$_{22}$H$_{21}$BN$_2$O$_2$: calc. 356.16, found 356.24

Synthesis of Compound 25

Compound 25 was obtained by using the same method as used to synthesize Compound 11, except that Intermediate I-5 was used instead of 2-(4-bromophenyl)-1-phenyl-1-benzoimidazole and Intermediate I-6 was used instead of Intermediate I-3. The formed compound was identified by MS/FAB and $^1$H NMR. C$_{32}$H$_{20}$N$_4$: calc. 460.16, found 460.24.

$^1$H NMR (CDCl$_3$, 400 MHz) δ(ppm) 9.42-9.40 (m, 1H), 9.05-9.03 (m, 2H), 9.00-8.99 (m, 2H), 8.80-8.79 (m, 1H), 8.71-8.66 (m, 4H), 8.56-8.55 (m, 2H), 8.40-8.37 (m, 1H), 8.18 (d, 1H), 8.06-8.00 (m, 3H), 7.50-7.46 (m, 2H), 7.43-7.39 (m, 1H).

SYNTHESIS EXAMPLE 4

Synthesis of Compound 28

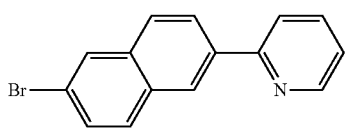

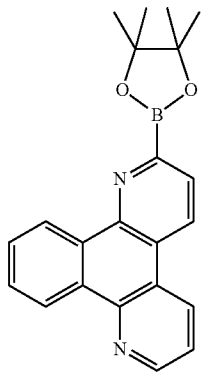

Intermediate I-7 was obtained by using the same method as used to synthesize Compound 11 of Synthesis Example 1 except that 2,6-dibromonaphthalene was used instead of 2-(4-bromophenyl)-1-phenyl-1-benzoimidazole and 2-pyridinylboric acid was used instead of Intermediate I-3. Intermediate I-8 was obtained by using the same method as used to synthesize Intermediate 1-3 of Synthesis Example 1 except that naphthalene-1,4-diamine was used instead of naphthalene-1, 5-diamine. Subsequently, Compound 28 was obtained by using the same method as used to synthesize Compound 11 of Synthesis Example 1, except that Intermediate I-8 was used instead of Intermediate I-3 and Intermediate I-7 was used instead of 2-(4-bromophenyl)-1-phenyl-1-benzoimidazole. The formed compound was identified by MS/FAB and $^1$H NMR. C$_{31}$H$_{19}$N$_3$: calc. 433.15, found 433.24.

$^1$H NMR (CDCl$_3$, 400 MHz) δ(ppm) 9.55-9.54 (m, 1H), 9.45-9.42 (m, 1H), 9.23-9.19 (m, 1H), 9.12-9.02 (m, 4H), 8.96-8.95 (m, 1H), 8.78-8.76 (m, 1H), 8.56-8.55 (m, 1H), 8.45-8.43 (m, 1H), 8.28-8.25 (m, 1H), 8.18-8.16 (d, 1H), 7.89-7.82 (m, 2H), 7.80-7.78 (m, 2H), 7.71-7.68 (m, 1H), 7.30-7.25 (m, 1H).

SYNTHESIS EXAMPLE 5

Synthesis of Compound 40

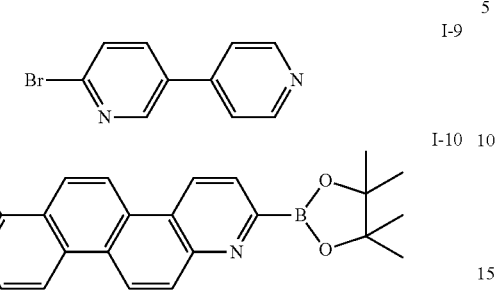

Intermediate I-9 was obtained by using the same method as used to synthesize Compound 11 of Synthesis Example 1 except that 2-bromo-5-iodopyridine was used instead of 2-(4-bromophenyl)-1-phenyl-1-benzoimidazole and 4-pyridinyl-boric acid was used instead of Intermediate I-3. Intermediate I-10 was obtained by using the same method as used to synthesize Intermediate I-3 of Synthesis Example 1, except that phenanthrene-2,7-diamine was used instead of naphthalene-1,5-diamine. Subsequently, Compound 40 was obtained by using the same method as used to synthesize Compound 11 of Synthesis Example 1, except that Intermediate I-10 was used instead of Intermediate I-3 and Intermediate I-9 was used instead of 2-(4-bromophenyl)-1-phenyl-1-benzoimidazole. The formed compound was identified by MS/FAB and $^1$H NMR. $C_{30}H_{18}N_4$: calc. 434.15, found 434.22.

$^1$H NMR (CDCl$_3$, 400 MHz) δ(ppm) 9.70-9.69 (m, 1H), 9.44-9.43 (m, 1H), 9.39-9.35 (m, 2H), 9.17-9.16 (m, 1H), 8.99-8.97 (m, 1H), 8.90-8.88 (m, 1H), 8.67-8.64 (m, 3H), 8.50 (d, 1H), 8.25 (d, 1H), 8.21-8.19 (m, 1H), 7.99 (d, 1H), 7.43-7.39 (m, 4H).

SYNTHESIS EXAMPLE 6

Synthesis of Compound 51

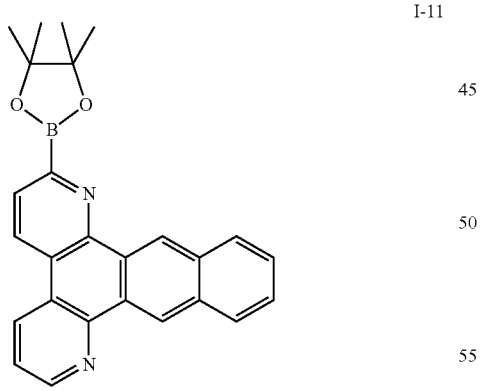

Intermediate I-11 was obtained by using the same method as used to synthesize Intermediate I-3 of Synthesis Example 1, except that anthracene-1,4-diamine was used instead of naphthalene-1,5-diamine. Subsequently, Compound 51 was obtained by using the same method as used to synthesize Compound 11 of Synthesis Example 1, except that Intermediate I-11 was used instead of Intermediate I-3 and 2-chloro-4,6-diphenyl-[1,3,5]-triazine was used instead of 2-(4-bromophenyl)-1-phenyl-1-benzoimidazole. The formed compound was identified by MS/FAB and $^1$H NMR. $C_{35}H_{21}N_5$: calc. 511.17, found 511.22.

$^1$H NMR (CDCl$_3$, 400 MHz) δ(ppm) 9.64-9.62 (m, 1H), 9.57 (s, 1H), 9.39 (s, 1H), 9.11 (d, 1H), 9.05-9.04 (m, 1H), 8.90-8.87 (m, 4H), 8.83 (d, 1H), 8.28-8.24 (m, 2H), 7.71-7.68 (m, 1H), 7.63-7.54 (m, 6H), 7.42-7.38 (m, 2H).

SYNTHESIS EXAMPLE 7

Synthesis of Compound 57

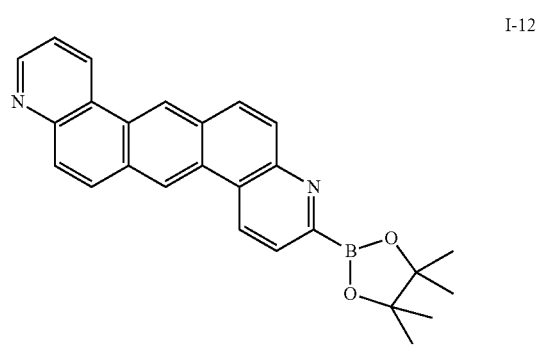 [SMILES: CC1(C)OB(c2ccc3c(ccc4cc5c(ccc6ncccc65)cc43)n2)OC1(C)C]

Intermediate I-12 was obtained by using the same method as used to synthesize Intermediate 1-3 of Synthesis Example 1, except that anthracene-2,6-diamine was used instead of naphthalene-1,5-diamine. Subsequently, Compound 57 was obtained by using the same method as used to synthesize Compound 11 of Synthesis Example 1, except that Intermediate I-12 was used instead of Intermediate I-3 and 3-(4-bromophenyl)-2-phenyl-imidazolepyridine was used instead of 2-(4-bromophenyl)-1-phenyl-1-benzoimidazole. The formed compound was identified by MS/FAB and $^1$H NMR. $C_{39}H_{24}N_4$: calc. 548.20, found 548.27

$^1$H NMR (CDCl$_3$, 400 MHz) δ(ppm) 8.96-8.94 (m, 2H), 8.87-8.85 (m, 1H), 8.80-8.79 (m, 1H), 8.67-8.64 (m, 2H), 8.38-8.15 (m, 7H), 7.98-7.95 (m, 2H), 7.84-7.77 (m, 2H), 7.66-7.64 (m, 1H), 7.43-7.36 (m, 4H), 7.28-7.24 (m, 1H), 6.91-6.87 (m, 1H)

SYNTHESIS EXAMPLE 8

Synthesis of Compound 60

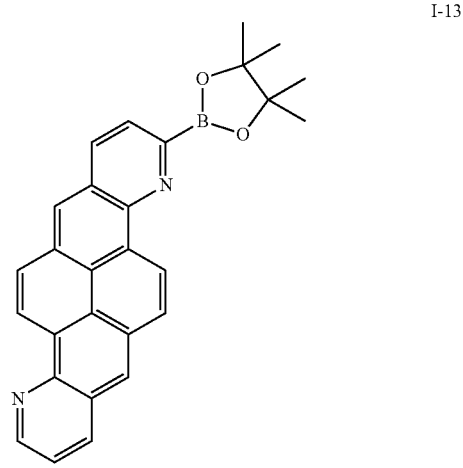 [SMILES: CC1(C)OB(c2ccc3cc4ccc5c6ncccc6cc6ccc(c3n2)c4c65)OC1(C)C]

Intermediate I-13 was obtained by using the same method as used to synthesize Intermediate 1-3 of Synthesis Example 1, except that pyrene-1,6-diamine was used instead of naphthalene-1,5-diamine. Subsequently, Compound 51 was obtained by using the same method as used to synthesize Compound 11 of Synthesis Example 1, except that Intermediate I-13 was used instead of Intermediate I-3 and 2-chloro-4,6-diphenyl-[1,3,5]-triazine was used instead of 2-(4-bromophenyl)-1-phenyl-1-benzoimidazole. The formed compound was identified by MS/FAB and $^1$H NMR. $C_{37}H_{21}N_6$: calc. 535.17, found 535.25.

$^1$H NMR (CDCl$_3$, 400 MHz) δ(ppm) 9.18-9.15 (m, 1H), 8.94-8.66 (m, 6H), 8.76 (d, 1H), 8.57-8.54 (m, 2H), 8.38-8.35 (m, 3H), 8.26-8.24 (m, 1H), 7.64-7.59 (m, 4H), 7.45-7.38 (m, 3H).

SYNTHESIS EXAMPLE 9

Synthesis of Compound 65

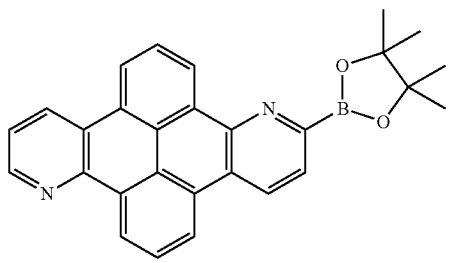

I-14

Intermediate I-14 was obtained by using the same method as used to synthesize Intermediate 1-3 of Synthesis Example 1, except that pyrene-4,9-diamine was used instead of naphthalene-1,5-diamine. Subsequently Compound 65 was obtained by using the same method as used to synthesize Compound 11 of Synthesis Example 1, except that Intermediate I-14 was used instead of Intermediate I-3 and 2-(4-bromophenyl)-1-phenyl-1-benzoimidazole was used. The formed compound was identified by MS/FAB and $^1$H NMR. $C_{41}H_{24}N_4$: calc. 572.20, found 572.27.

$^1$H NMR (CDCl$_3$, 400 MHz) δ(ppm) 9.74-9.68 (m, 2H), 9.35 (d, 1H), 8.90-8.87 (m, 2H), 8.72-8.70 (m, 2H), 8.24-8.21 (m, 3H), 8.17-8.14 (m, 2H), 7.90-7.84 (m, 2H), 7.99-7.97 (m, 1H), 7.66-7.64 (m, 1H), 7.58-7.53 (m, 2H), 7.44-7.36 (m, 3H), 7.32-7.28 (m, 2H), 7.24-7.21 (m, 1H).

SYNTHESIS EXAMPLE 10

Synthesis of Compound 67

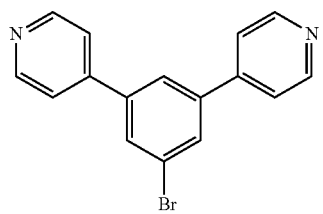

I-15

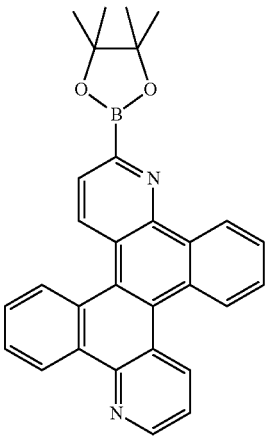

I-16

Intermediate I-15 was obtained by using the same method as used to synthesize Intermediate I-5 of Synthesis Example 3, except that 4-pyridinylboric acid was used instead of 3-pyridinylboric acid. Subsequently, Compound 67 was obtained by using the same method as used to synthesize Compound 11 of Synthesis Example 1, except that Intermediate 1-16 was used instead of Intermediate I-3 and Intermediate I-15 was used instead of 2-(4-bromophenyl)-1-phenyl-1-benzoimidazole. The formed compound was identified by MS/FAB and $^1$H NMR. $C_{40}H_{24}N_4$: calc. 560.20, found 560.27

$^1$H NMR (CDCl$_3$, 400 MHz) δ(ppm) 9.60-9.57 (m, 1H), 9.53-9.51 (m, 1H), 9.42-9.39 (m, 1H), 8.98-8.89 (m, 3H), 8.80-8.78 (m, 4H), 8.58-8.53 (m, 1H), 8.33-8.32 (m, 2H), 8.11-8.07 (m, 2H), 7.86-7.78 (m, 4H), 7.63-7.60 (m, 4H), 7.34-7.32 (m, 1H)

SYNTHESIS EXAMPLE 11

Synthesis of Compound 1

Compound 1 was obtained by using the same method as used to synthesize Intermediate I-1 of Synthesis Example 1. The formed compound was identified by MS/FAB and $^1$H NMR. calc. 230.08, found 230.15

$^1$H NMR (CDCl$_3$, 400 MHz) δ(ppm) 8.95-8.91 (m, 4H), 8.10-8.07 (m, 2H), 7.89 (d, 2H), 7.51-7.48 (m, 2H)

SYNTHESIS EXAMPLE 12

Synthesis of Compound 2

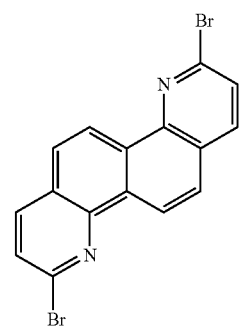

I-17-1

-continued

I-17-2

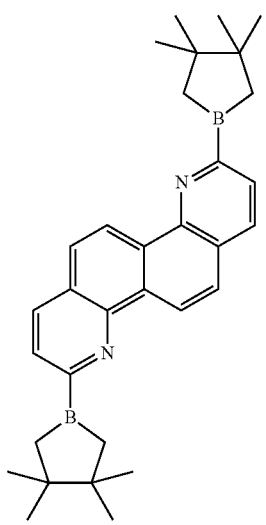

Intermediate I-17-1 was obtained by using the same method as used to synthesize Intermediate I-2 of Synthesis Example 1, except that an equivalent number of bromine was increased twice. Intermediate I-17-2 was obtained by using the same method as used to synthesize Intermediate I-3, except that Intermediate I-17-1 was used instead of Intermediate 1-2. Subsequently, Compound 2 was obtained by using the same method as used to synthesize Compound 11 of Synthesis Example 1, except that Intermediate I-17-2 was used instead of Intermediate I-3 and 2-bromo-2-methylpropane was used instead of 2-(4-bromophenyl)-1-phenyl-1-benzoimidazole. The formed compound was identified by MS/FAB and $^1$H NMR. calc. 342.20, found 342.28

$^1$H NMR (CDCl$_3$, 400 MHz) δ(ppm) 8.92 (d, 2H), 8.22-8.20 (m, 2H), 7.87 (d, 2H), 7.47 (d, 2H), 1.41 (s, 18H)

SYNTHESIS EXAMPLE 13

Synthesis of Compound 3

Compound 3 was obtained by using the same method as used to synthesize Compound 11 of Synthesis Example 1, except that Intermediate I-17-2 was used instead of Intermediate I-3 and bromobenzene was used instead of 2-(4-bromophenyl)-1-phenyl-1-benzoimidazole. The formed compound was identified by MS/FAB and $^1$H NMR. calc. 382.14, found 382.21.

$^1$H NMR (CDCl$_3$, 400 MHz) δ(ppm) 8.98 (d, 2H), 8.43 (d, 2H), 8.14-8.10 (m, 4H), 7.99 (d, 2H), 7.89 (d, 2H), 7.59-7.55 (m, 4H), 7.50-7.46 (m, 2H).

SYNTHESIS EXAMPLE 14

Synthesis of Compound 6

Compound 6 was obtained by using the same method as used to synthesize Compound 11 of Synthesis Example 1, except that Intermediate I-3 was used and 6-bromo-2,3'-bipyridine was used instead of Intermediate 2-(4-bromophenyl)-1-phenyl-1-benzoimidazole. The formed compound was identified by MS/FAB and $^1$H NMR. calc. 384.13, found 384.21.

$^1$H NMR (CDCl$_3$, 400 MHz) δ(ppm) 9.08-9.06 (m, 1H), 9.02-9.00 (m, 1H), 8.97-8.94 (m, 2H), 8.80 (d, 1H), 8.66-8.64 (d, 1H), 8.42-8.39 (m, 1H), 8.36 (d, 1H), 8.26-8.22 (m, 1H), 8.10-8.07 (m, 1H), 7.95-7.91 (m, 2H), 7.86 (d, 1H), 7.59 (d, 1H), 7.51-7.48 (m, 1H), 7.41-7.37 (m, 1H).

SYNTHESIS EXAMPLE 15

Synthesis of Compound 8

Compound 8 was obtained by using the same method as used to synthesize Compound 11 of Synthesis Example 1, except that Intermediate I-17-2 was used instead of Intermediate I-3 and 3-bromobenzonitrile was used instead of Intermediate 2-(4-bromophenyl)-1-phenyl-1-benzoimidazole. The formed compound was identified by MS/FAB and $^1$H NMR. calc. 432.13, found 432.20.

$^1$H NMR (CDCl$_3$, 400 MHz) δ(ppm) 8.98 (d, 2H), 8.64-8.62 (d, 2H), 8.53-8.51 (m, 2H), 8.14-8.09 (m, 4H), 7.89 (d, 2H), 7.79-7.76 (m, 2H), 7.62-7.58 (m, 2H).

SYNTHESIS EXAMPLE 16

Synthesis of Compound 15

Compound 15 was obtained by using the same method as used to synthesize Compound 11 of Synthesis Example 1, except that Intermediate I-3 was used and Intermediate I-4 was used instead of Intermediate 2-(4-bromophenyl)-1-phenyl-1-benzoimidazole. The formed compound was identified by MS/FAB and $^1$H NMR. calc. 461.16, found 461.24.

$^1$H NMR (CDCl$_3$, 400 MHz) δ(ppm) 9.07-9.05 (m, 1H), 8.97-8.94 (m, 2H), 8.89-8.86 (m, 4H), 8.71 (d, 1H), 8.62 (d, 1H), 8.10-8.08 (m, 1H), 7.95 (d, 1H), 7.86 (d, 1H), 7.63-7.59 (m, 4H), 7.51-7.48 (m, 1H), 7.42-7.38 (m, 2H).

SYNTHESIS EXAMPLE 17

Synthesis of Compound 20

Compound 20 was obtained by using the same method as used to synthesize Compound 11 of Synthesis Example 1, except that Intermediate I-3 was used and 2-(4-bromophenyl)imidazopyrimidine was used instead of Intermediate 2-(4-bromophenyl)-1-phenyl-1-benzoimidazole. The formed compound was identified by MS/FAB and $^1$H NMR. calc. 423.14, found 423.20.

$^1$H NMR (CDCl$_3$, 400 MHz) δ(ppm) 8.96-8.94 (m, 3H), 8.49-8.42 (m, 3H), 8.33-8.27 (m, 4H), 8.10-8.08 (m, 1H), 8.03 (d, 1H), 7.94 (d, 1H), 7.89-7.85 (m, 2H), 7.51-7.48 (m, 1H), 6.82-6.80 (m, 1H).

SYNTHESIS EXAMPLE 18

Synthesis of Compound 23

I-18

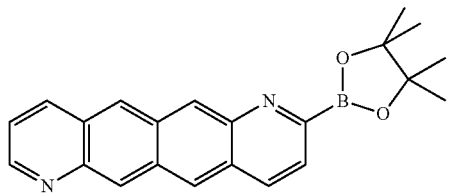

Intermediate I-18 was obtained by using the same method as used to synthesize Intermediate I-3 of Synthesis Example 1, except that naphthalene-2,6-diamine was used instead of naphthalene-1,5-diamine. Subsequently, Compound 23 was obtained by using the same method as used to synthesize Compound 11 of Synthesis Example 1, except that Intermediate I-18 was used instead of Intermediate I-3 and 2-(4-bromophenyl)-1-phenyl-1-benzoimidazole was used. The formed compound was identified by MS/FAB and ¹H NMR. calc. 498.18, found 498.24.

¹H NMR (CDCl₃, 400 MHz) δ(ppm) 8.96-8.94 (m, 1H), 8.86 (s, 1H), 8.80 (s, 1H), 8.50-8.45 (m, 3H), 8.29-8.26 (m, 1H), 8.22-8.20 (m, 2H), 8.13-8.11 (m, 2H), 8.03 (d, 1H), 7.80-7.78 (m, 1H), 7.66-7.64 (m, 1H), 7.57-7.53 (m, 2H), 7.44-7.35 (m, 3H), 7.32-7.28 (m, 1H), 7.24-7.15 (m, 2H).

SYNTHESIS EXAMPLE 19

Synthesis of Compound 27

Compound 27 was obtained by using the same method as used to synthesize Compound 11 of Synthesis Example 1, except that Intermediate I-8 was used instead of Intermediate I-3 and 3-(3-bromophenyl)pyridine was used instead of 2-(4-bromophenyl)-1-phenyl-1-benzoimidazole. The formed compound was identified by MS/FAB and ¹H NMR. calc. 383.14, found 383.21.

¹H NMR (CDCl₃, 400 MHz) δ(ppm) 9.44-9.42 (m, 1H), 9.23-9.18 (m, 1H), 9.11-9.09 (m, 1H), 9.03-9.02 (m, 1H), 8.96-8.95 (m, 1H), 8.92 (d, 1H), 8.66-8.64 (m, 1H), 8.56-8.55 (m, 1H), 8.32 (d, 1H), 8.12-8.09 (m, 1H), 7.97-7.95 (m, 1H), 7.87-7.83 (m, 2H), 7.70-7.68 (m, 1H), 7.48-7.39 (m, 2H), 7.39-7.36 (m, 1H).

SYNTHESIS EXAMPLE 20

Synthesis of Compound 30

Compound 30 was obtained by using the same method as used to synthesize Compound 11 of Synthesis Example 1, except that Intermediate I-8 was used instead of Intermediate I-3 and Intermediate I-4 was used instead of 2-(4-bromophenyl)-1-phenyl-1-benzoimidazole. The formed compound was identified by MS/FAB and ¹H NMR. calc. 537.19, found 537.24.

¹H NMR (CDCl₃, 400 MHz) δ(ppm) 9.44-9.42 (m, 1H), 9.22-9.19 (m, 1H), 9.11-9.09 (m, 1H), 9.03-9.02 (m, 1H), 8.81-8.78 (m, 6H), 8.59-8.57 (m, 2H), 8.51-8.49 (m, 1H), 8.31 (d, 1H), 7.88-7.82 (m, 2H), 7.71-7.68 (m, 1H), 7.63-7.59 (m, 4H), 7.42-7.38 (m, 2H).

SYNTHESIS EXAMPLE 21

Synthesis of Compound 33

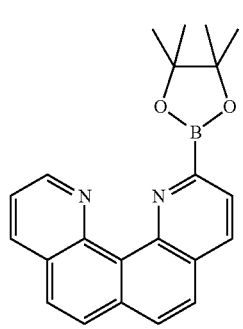

I-19

Intermediate I-19 was obtained by using the same method as used to synthesize Intermediate I-3 of Synthesis Example 1, except that naphthalene-1,8-diamine was used instead of naphthalene-1,5-diamine. Subsequently Compound 33 was obtained by using the same method as used to synthesize Compound 11 of Synthesis Example 1, except that Intermediate I-19 was used instead of Intermediate I-3 and 1-(4-bromophenyl)-2-phenyl-1-benzoimidazole was used instead of 2-(4-bromophenyl)-1-phenyl-1-benzoimidazole. The formed compound was identified by MS/FAB and ¹H NMR. calc. 498.18, found 498.23.

¹H NMR (CDCl₃, 400 MHz) δ(ppm) 9.02-9.00 (m, 1H), 8.50-8.48 (m, 1H), 8.24-8.21 (m, 2H), 8.08-8.03 (m, 4H), 7.84-7.75 (m, 5H), 7.66-7.64 (m, 1H), 7.51-7.48 (m, 1H), 7.42-7.28 (m, 6H), 7.24-7.21 (m, 1H).

SYNTHESIS EXAMPLE 22

Synthesis of Compound 34

Compound 34 was obtained by using the same method as used to synthesize Compound 11 of Synthesis Example 1, except that Intermediate I-19 was used instead of Intermediate I-3 and Intermediate I-4 was used instead of 2-(4-bromophenyl)-1-phenyl-1-benzoimidazole. The formed compound was identified by MS/FAB and ¹H NMR. calc. 537.19, found 537.25.

¹H NMR (CDCl₃, 400 MHz) δ(ppm) 9.17-9.06 (m, 6H), 8.97 (d, 1H), 8.89-8.88 (m, 1H), 8.79 (d, 1H), 8.57-8.56 (m, 1H), 8.49-8.47 (m, 1H), 8.35-8.33 (m, 1H), 8.16-8.10 (m, 4H), 7.99 (d, 1H), 7.90-7.86 (m, 3H), 7.70-7.66 (m, 1H), 7.52-7.43 (m, 2H).

SYNTHESIS EXAMPLE 23

Synthesis of Compound 42

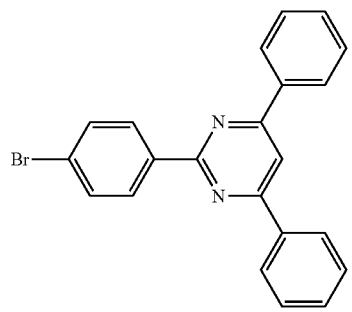

I-20-1

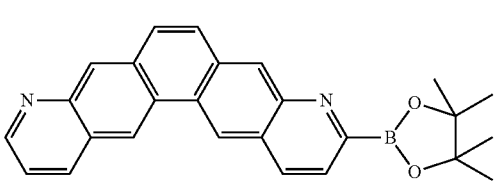

I-20-2

Intermediate I-20-1 was obtained by using the same method as used to synthesize Intermediate I-4 of Synthesis Example 2, except that 2-chloro-4,6-diphenyl-pyrimidine was used instead of 2-chloro-4,6-diphenyl-[1,3,5]-triazine. Intermediate I-20-2 was obtained by using the same method as used to synthesize Intermediate I-3 of Synthesis Example 1, except that phenanthrene-2,7-diamine was used instead of naphthalene-1,5-diamine. Subsequently, Compound 42 was obtained by using the same method as used to synthesize Compound 11 of Synthesis Example 1, except that Intermediate I-20-2 was used instead of Intermediate I-3 and Intermediate I-20-1 was used instead of 2-(4-bromophenyl)-1-phenyl-1-benzoimidazole. The formed compound was identified by MS/FAB and $^1$H NMR. calc. 586.15, found 586.22.

$^1$H NMR (CDCl$_3$, 400 MHz) δ(ppm) 9.60 (s, 1H), 9.51 (s, 1H), 8.95-8.94 (m, 1H), 8.79-8.78 (m, 1H), 8.73-8.72 (m, 1H), 8.56-8.53 (m, 2H), 8.45-8.40 (m, 3H), 8.33-8.27 (m, 5H), 8.12-8.04 (m, 3H), 7.96 (s, 1H), 7.52-7.49 (m, 4H), 7.31-7.27 (m, 2H), 7.17-7.14 (m, 1H).

SYNTHESIS EXAMPLE 24

Synthesis of Compound 43

Compound 43 was obtained by using the same method as used to synthesize Compound 11 of Synthesis Example 1, except that Intermediate I-20-2 was used instead of Intermediate I-3 and 2-bromoquinoline was used instead of 2-(4-bromophenyl)-1-phenyl-1-benzoimidazole. The formed compound was identified by MS/FAB and $^1$H NMR. calc. 407.14, found 407.21.

$^1$H NMR (CDCl$_3$, 400 MHz) δ(ppm) 9.51 (s, 1H), 9.18 (s, 1H), 8.91 (d, 1H), 8.86-8.85 (m, 1H), 8.79 (d, 1H), 8.73-8.72 (m, 1H), 8.39 (d, 1H), 8.32-8.30 (m, 1H), 8.26-8.22 (m, 2H), 8.12-8.04 (m, 2H), 7.86-7.84 (m, 1H), 7.75-7.71 (m, 1H), 7.57-7.53 (m, 2H), 7.17-7.14 (m, 1H).

SYNTHESIS EXAMPLE 25

Synthesis of Compound 46

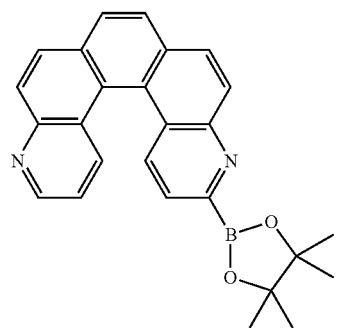

I-21

Intermediate I-21 was obtained by using the same method as used to synthesize Intermediate I-3 of Synthesis Example 1, except that phenanthrene-3,6-diamine was used instead of naphthalene-1,5-diamine. Subsequently, Compound 46 was obtained by using the same method as used to synthesize Compound 11 of Synthesis Example 1, except that Intermediate I-21 was used instead of Intermediate I-3 and 2-bromo-4,6-diphenylpyrimidine was used instead of 2-(4-bromophenyl)-1-phenyl-1-benzoimidazole. The formed compound was identified by MS/FAB and $^1$H NMR. calc. 510.18, found 510.25.

$^1$H NMR (CDCl$_3$, 400 MHz) δ(ppm) 9.41-9.39 (m, 1H), 8.95-8.94 (m, 1H), 8.78-8.76 (m, 1H), 8.67-8.65 (m, 2H), 8.49-8.47 (m, 1H), 8.35-8.31 (m, 4H), 8.23-8.15 (m, 2H), 8.08-8.00 (m, 2H), 7.95 (s, 1H), 7.52-7.49 (m, 4H), 7.30-7.25 (m, 3H).

SYNTHESIS EXAMPLE 26

Synthesis of Compound 47

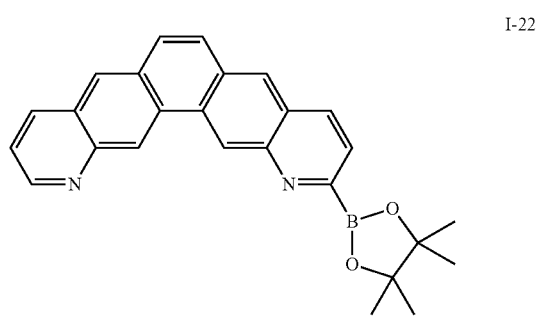 [SMILES: CC1(C)OB(c2ccc3cc4ccc5cc6cccnc6cc5c4cc3n2)OC1(C)C]

I-22

Intermediate I-22 was obtained by using the same method as used to synthesize Intermediate I-3 of Synthesis Example 1, except that phenanthrene-3,6-diamine was used instead of naphthalene-1,5-diamine. Subsequently, Compound 47 was obtained by using the same method as used to synthesize Compound 11 of Synthesis Example 1, except that Intermediate I-22 was used instead of Intermediate I-3 and 5-bromoquinoline was used instead of 2-(4-bromophenyl)-1-phenyl-1-benzoimidazole. The formed compound was identified by MS/FAB and $^1$H NMR. calc. 407.14, found 407.21.

$^1$H NMR (CDCl$_3$, 400 MHz) δ(ppm) 9.20-9.19 (m, 1H), 9.14-9.13 (m, 1H), 9.06-9.04 (m, 1H), 8.92-8.91 (m, 1H), 8.74-8.73 (m, 1H), 8.49-8.47 (m, 2H), 8.39-8.35 (m, 3H), 8.29-8.21 (m, 3H), 7.79-7.75 (m, 1H), 7.68-7.66 (m, 1H), 7.58-7.55 (m, 1H), 7.19-7.15 (m, 1H).

SYNTHESIS EXAMPLE 27

Synthesis of Compound 50

Compound 50 was obtained by using the same method as used to synthesize Compound 11 of Synthesis Example 1, except that Intermediate I-11 was used instead of Intermediate I-3 and 5-bromo-2,2'-bipyridine was used instead of, 2-(4-bromophenyl)-1-phenyl-1-benzoimidazole. The formed compound was identified by MS/FAB and $^1$H NMR. calc. 511.17, found 511.24.

$^1$H NMR (CDCl$_3$, 400 MHz) δ(ppm) 9.64-9.62 (m, 1H), 9.41-9.39 (m, 2H), 9.16-9.15 (m, 1H), 9.08 (m, 1H), 9.05-9.03 (m, 1H), 8.71-8.69 (m, 1H), 8.61-8.59 (m, 1H), 8.52-8.50 (m, 1H), 8.41-8.39 (m, 1H), 8.28-8.24 (m, 3H), 7.84-7.80 (m, 1H), 7.71-7.68 (m, 11-1), 7.59-7.54 (m, 2H), 7.32-7.29 (m, 1H).

SYNTHESIS EXAMPLE 28

Synthesis of Compound 52

Compound 52 was obtained by using the same method as used to synthesize Compound 11 of Synthesis Example 1, except that Intermediate I-11 was used instead of Intermediate I-3 and 2-(4-bromophenyl)-1-phenyl-1-benzoimidazole was used. The formed compound was identified by MS/FAB and $^1$H NMR. calc. 548.20, found 548.29.

$^1$H NMR (CDCl$_3$, 400 MHz) δ(ppm) 9.64-9.62 (m, 1H), 9.40-9.39 (m, 2H), 9.05-9.04 (m, 1H), 8.95 (d, 1H), 8.32-8.21 (m, 5H), 8.17-8.14 (m, 2H), 7.79-7.77 (m, 1H), 7.71-7.64 (m, 2H), 7.60-7.55 (m, 4H), 7.44-7.35 (m, 3H), 7.32-7.28 (m, 1H), 7.24-7.21 (m, 1H).

SYNTHESIS EXAMPLE 29

Synthesis of Compound 55

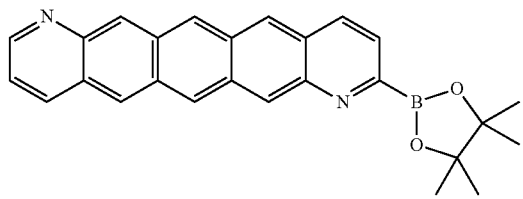

I-23

Intermediate I-23 was obtained by using the same method as used to synthesize Intermediate I-3 of Synthesis Example 1, except that anthracene-2,6-diamine was used instead of naphthalene-1,5-diamine. Subsequently Compound 55 was obtained by using the same method as used to synthesize Compound 11 of Synthesis Example 1, except that Intermediate I-23 was used instead of Intermediate I-3 and 2-(4-bromophenyl)-3-phenylimidazolepyridine was used instead of 2-(4-bromophenyl)-1-phenyl-1-benzoimidazole. The formed compound was identified by MS/FAB and $^1$H NMR. calc. 548.20, found 548.28.

$^1$H NMR (CDCl$_3$, 400 MHz) δ(ppm) 8.96-8.94 (m, 1H), 8.78 (s, 1H), 8.72 (s, 1H), 8.66-8.65 (m, 2H), 8.63-8.60 (m, 1H), 8.47 (d, 2H), 8.40 (d, 1H), 8.25-8.16 (m, 5H), 8.03 (d, 1H), 7.78-7.73 (m, 2H), 7.66-7.64 (m, 1H), 7.52-7.44 (m, 3H), 7.28-7.24 (m, 1H), 7.19-7.15 (m, 1H), 6.91-6.97 (m, 1H).

SYNTHESIS EXAMPLE 30

Synthesis of Compound 56

Compound 56 was obtained by using the same method as used to synthesize Compound 11 of Synthesis Example 1, except that Intermediate I-12 was used instead of Intermediate I-3 and 3-(4-bromophenyl)pyridine was used instead of 2-(4-bromophenyl)-1-phenyl-1-benzoimidazole. The formed compound was identified by MS/FAB and $^1$H NMR. calc. 434.15, found 434.21.

$^1$H NMR (CDCl$_3$, 400 MHz) δ(ppm) 9.16-9.14 (m, 1H), 8.97-8.93 (m, 3H), 8.81-8.79 (m, 1H), 8.67-8.60 (m, 2H); 8.56-8.52 (m, 2H), 8.44-8.39 (d, 2H), 8.30-8.28 (m, 1H), 8.25-8.21 (m, 2H), 7.80-8.73 (d, 2H), 7.43-7.39 (m, 1H), 7.29-7.26 (m, 1H).

SYNTHESIS EXAMPLE 31

Synthesis of Compound 58

Compound 58 was obtained by using the same method as used to synthesize Compound 11 of Synthesis Example 1, except that Intermediate I-12 was used instead of Intermediate I-3 and Intermediate I-5 was used instead of 2-(4-bromophenyl)-1-phenyl-1-benzoimidazole. The formed compound was identified by MS/FAB and $^1$H NMR. calc. 510.18, found 510.25.

$^1$H NMR (CDCl$_3$, 400 MHz) δ(ppm) 9.16-9.13 (m, 1H), 9.00-8.99 (m, 2H), 8.96-8.94 (m, 2H), 8.81-8.80 (m, 1H), 8.68-8.64 (m, 3H), 8.56-8.55 (m, 2H), 8.38-8.28 (m, 3H), 8.23-8.17 (m, 2H), 8.06-8.00 (m, 3H), 7.50-7.46 (m, 2H), 7.43-7.39 (m, 1H).

SYNTHESIS EXAMPLE 32

Synthesis of Compound 61

Compound 61 was obtained by using the same method as used to synthesize Compound 11 of Synthesis Example 1, except that Intermediate I-13 was used instead of Intermediate I-3 and 2-(4-bromophenyl)-1-phenyl-1-benzoimidazole was used. The formed compound was identified by MS/FAB and $^1$H NMR. calc. 572.20, found 572.27.

$^1$H NMR (CDCl$_3$, 400 MHz) δ(ppm) 9.16 (d, 1H), 8.92-8.90 (m, 1H), 8.83 (d, 1H), 8.44-8.42 (m, 1H), 8.39-8.35 (m, 4H), 8.26-8.14 (m, 5H), 8.08-8.06 (m, 1H), 7.80-7.78 (m, 1H), 7.66-7.64 (m, 1H), 7.58-7.55 (m, 2H), 7.45-7.35 (m, 4H), 7.32-7.28 (m, 1H), 7.24-7.21 (m, 1H).

SYNTHESIS EXAMPLE 33

Synthesis of Compound 63

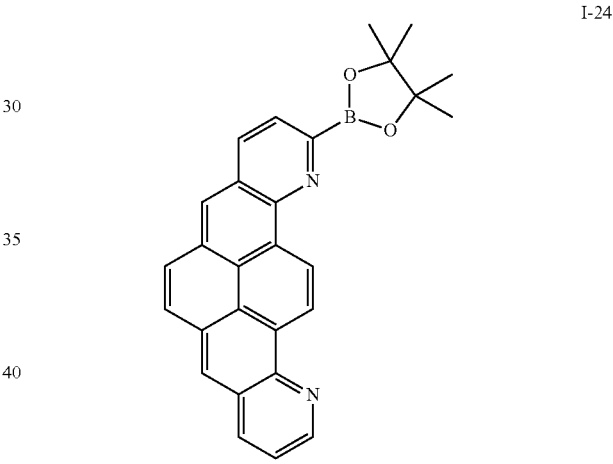

I-24

Intermediate I-24 was obtained by using the same method as used to synthesize Intermediate I-3 of Synthesis Example 1, except that pyrene-1,8-diamine was used instead of naphthalene-1,5-diamine. Subsequently, Compound 63 was obtained by using the same method as used to synthesize Compound 11 of Synthesis Example 1, except that Intermediate I-24 was used instead of Intermediate I-3 and Intermediate I-5 was used instead of 2-(4-bromophenyl)-1-phenyl-1-benzoimidazole. The formed compound was identified by MS/FAB and $^1$H NMR. calc. 534.18, found 534.27.

$^1$H NMR (CDCl$_3$, 400 MHz) δ(ppm) 9.00-8.98 (m, 2H), 8.94-8.93 (m, 2H), 8.92-8.90 (m, 1H), 8.68-8.66 (m, 2H), 8.62-8.60 (m, 2H), 8.44-8.33 (m, 5H), 8.26-8.21 (m, 2H), 8.06-8.00 (m, 3H), 7.50-7.41 (m, 3H).

SYNTHESIS EXAMPLE 34

Synthesis of Compound 69

Compound 69 was obtained by using the same method as used to synthesize Compound 11 of Synthesis Example 1, except that Intermediate I-16 was used instead of Intermediate I-3 and 1-(4-bromophenyl)-2-phenyl-1-benzoimidazole was used instead of 2-(4-bromophenyl)-1-phenyl-1-benzoimidazole. The formed compound was identified by MS/FAB and ¹H NMR. calc. 598.21, found 598.29.

¹H NMR (CDCl₃, 400 MHz) δ(ppm) 9.60-9.50 (m, 2H), 9.06-9.04 (m, 1H), 8.97-8.91 (m, 3H), 8.58-8.53 (m, 1H), 8.29 (d, 1H), 8.08-8.03 (m, 4H), 7.86-7.77 (m, 5H), 7.66-7.64 (m, 1H), 7.41-7.29 (m, 7H), 7.24-7.21 (m, 1H).

SYNTHESIS EXAMPLE 35

Synthesis of Compound 70

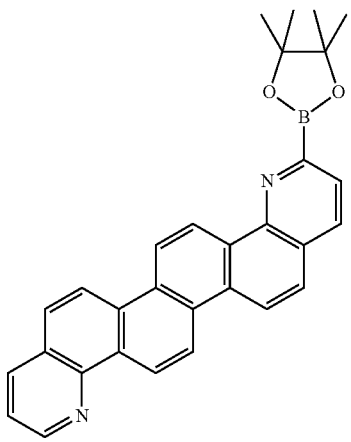

I-25

Intermediate I-25 was obtained by using the same method as used to synthesize Intermediate I-3 of Synthesis Example 1, except that chrysene-1,7-diamine was used instead of naphthalene-1,5-diamine. Subsequently, Compound 70 was obtained by using the same method as used to synthesize Compound 11 of Synthesis Example 1, except that Intermediate I-25 was used instead of Intermediate I-3 and Intermediate I-4 was used instead of 2-(4-bromophenyl)-1-phenyl-1-benzoimidazole. The formed compound was identified by MS/FAB and ¹H NMR. calc. 561.19, found 561.25.

¹H NMR (CDCl₃, 400 MHz) δ(ppm) 9.12-9.10 (m, 1H), 8.99-8.97 (m, 1H), 8.93-8.87 (m, 8H), 8.76-8.70 (m, 2H), 8.55-8.52 (m, 1H), 8.12-8.10 (m, 1H), 8.00-7.98 (m, 1H), 7.83-7.81 (m, 1H), 7.63-7.60 (m, 4H), 7.46-7.38 (m, 3H).

SYNTHESIS EXAMPLE 36

Synthesis of Compound 72

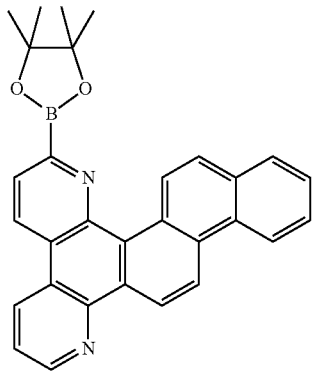

I-26

Intermediate I-26 was obtained by using the same method as used to synthesize Intermediate I-3 of Synthesis Example 1, except that chrysene-1,4-diamine was used instead of naphthalene-1,5-diamine. Subsequently, Compound 72 was obtained by using the same method as used to synthesize Compound 11 of Synthesis Example 1, except that Intermediate I-26 was used instead of Intermediate I-3 and 3-(3-bromophenyl)pyridine was used instead of 2-(4-bromophenyl)-1-phenyl-1-benzoimidazole. The formed compound was identified by MS/FAB and ¹H NMR. calc. 484.16, found 484.23.

¹H NMR (CDCl₃, 400 MHz) δ(ppm) 9.64-9.62 (m, 1H), 9.23-9.21 (m, 1H), 9.08-8.98 (m, 4H), 8.93-8.91 (m, 1H), 8.84-8.83 (m, 1H), 8.68-8.65 (m, 3H), 8.62 (d, 1H), 8.24 (d, 1H), 8.06-8.04 (m, 1H), 8.00-7.87 (m, 1H), 7.82-7.78 (m, 1H), 7.71-7.65 (m, 2H), 7.43-7.41 (m, 2H).

SYNTHESIS EXAMPLE 37

Synthesis of Compound 76

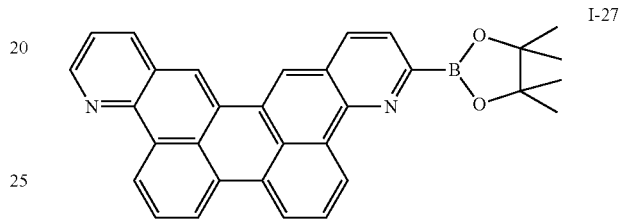

I-27

Intermediate I-27 was obtained by using the same method as used to synthesize Intermediate I-3 of Synthesis Example 1, except that perylene-3,10-diamine was used instead of naphthalene-1,5-diamine. Subsequently, Compound 76 was obtained by using the same method as used to synthesize Compound 11 of Synthesis Example 1, except that Intermediate I-27 was used instead of Intermediate I-3 and 7-bromoquinoline was used instead of 2-(4-bromophenyl)-1-phenyl-1-benzoimidazole. The formed compound was identified by MS/FAB and ¹H NMR. calc. 481.15, found 481.22.

¹H NMR (CDCl₃, 400 MHz) δ(ppm) 9.59-9.54 (m, 2H), 9.17 (s, 1H), 9.11 (s, 1H), 9.05-9.03 (m, 1H), 8.92-8.90 (m, 1H), 8.70-8.66 (m, 2H), 8.62-8.60 (m, 1H), 8.55 (d, 1H), 8.48-8.46 (m, 1H), 8.36-8.34 (m, 1H), 8.27 (d, H), 8.23-8.18 (m, 2H), 7.85-7.78 (m, 2H), 7.46-7.43 (m, 1H), 7.40-7.36 (m, 1H).

EXAMPLE 1

As an anode, 15 Ω/cm² (1200 Å) ITO glass substrate manufactured by Corning Co., Ltd was cut to a size of 50 mm×50 mm×0.7 mm and sonicated with isopropyl alcohol and pure water each for 5 minutes, and then a ultraviolet ray was irradiated thereto for 30 minutes, followed by exposure to ozone. Then, the resultant ITO glass substrate was installed in a vacuum deposition device.

2-TNATA was vacuum deposited on the ITO glass substrate to form a hole injection layer having a thickness of 600 Å, and 4,4'-bis[N-(1-naphthyl)-N-phenyl amino]biphenyl (NPB) was vacuum deposited on the hole injection layer to form a hole transport layer having a thickness of 300 Å.

On the hole transport layer, Alq₃ as a green fluorescent host and C545T as a blue fluorescent dopant were co-deposited at a weight ratio of 98:2 to form an emission layer having a thickness of 300 Å.

Subsequently, Compound 11 was vacuum deposited on the emission layer to form an electron transport layer having a thickness of 300 Å. LiF, which is a halgenaized alkali metal, was vacuum deposited on the electron transport layer to form an electron injection layer having a thickness of 10 Å, and then, Al was vacuum deposited thereon to a thickness of 3000 Å (andoe), thereby completing manufacture of a LiF/Al electrode. Thus, manufacture of an organic light-emitting diode was completed.

EXAMPLE 2

An organic light-emitting diode was manufactured in the same manner as in Example 1, except that Compound 17 was used instead of Compound 11 in forming an electron transport layer.

EXAMPLE 3

An organic light-emitting diode was manufactured in the same manner as in Example 1, except that Compound 25 was, used instead of Compound 11 in forming an electron transport layer.

EXAMPLE 4

An organic light-emitting diode was manufactured in the same manner as in Example 1, except that Compound 28 was used instead of Compound 11 in forming an electron transport layer.

EXAMPLE 5

An organic light-emitting diode was manufactured in the same manner as in Example 1, except that Compound 40 was used instead of Compound 11 in forming an electron transport layer.

EXAMPLE 6

An organic light-emitting diode was manufactured in the same manner as in Example 1, except that Compound 51 was used instead of Compound 11 in forming an electron transport layer.

EXAMPLE 7

An organic light-emitting diode was manufactured in the same manner as in Example 1, except that Compound 57 was used instead of Compound 11 in forming an electron transport layer.

EXAMPLE 8

An organic light-emitting diode was manufactured in the same manner as in Example 1, except that Compound 60 was used instead of Compound 11 in forming an electron transport layer.

EXAMPLE 9

An organic light-emitting diode was manufactured in the same manner as in Example 1, except that Compound 65 was used instead of Compound 11 in forming an electron transport layer.

EXAMPLE 10

An organic light-emitting diode was manufactured in the same manner as in Example 1, except that Compound 67 was used instead of Compound 11 in forming an electron transport layer.

COMPARITIVE EXAMPLE 1

An organic light-emitting diode was manufactured in the same manner as in Example 1 except that $Alq_3$, which is a known material, was used instead of Compound 11 in forming an electron transport layer.

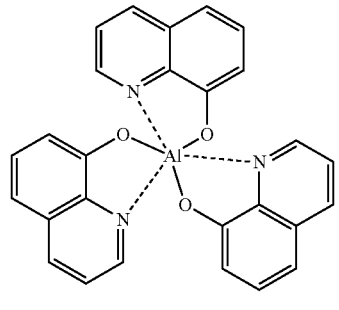

$Alq_3$

EVALUATION EXAMPLE

The driving voltage, current density, brightness, luminescence efficiency, emission color, and half lifetime of each of the organic light-emitting diodes of Examples 1 to 10 and Comparative Example 1 were measured by using a PR650 (Spectroscan) Source Measurement Unit (product of Photo-Research Co., Ltd). Results thereof are shown in Table 1 below.

TABLE 1

| | Electron transport material | Driving voltage (V) | Current density (mA/cm$^2$) | Brightness (cd/m$^2$) | Luminous efficiency (cd/A) | Emission color | Half lifetime (hr @ 100 mA/cm$^2$) |
|---|---|---|---|---|---|---|---|
| Example 1 | Compound 11 | 6.26 | 50 | 2.645 | 5.29 | blue | 215 hr |
| Example 2 | Compound 17 | 6.35 | 50 | 2.687 | 5.37 | blue | 221 hr |
| Example 3 | Compound 25 | 6.51 | 50 | 2.352 | 4.70 | blue | 202 hr |
| Example 4 | Compound 28 | 6.55 | 50 | 2.233 | 4.46 | blue | 210 hr |
| Example 5 | Compound 40 | 6.72 | 50 | 2.214 | 4.43 | blue | 198 hr |
| Example 6 | Compound 51 | 6.28 | 50 | 2.577 | 5.15 | blue | 209 hr |
| Example 7 | Compound 57 | 6.87 | 50 | 2.135 | 4.27 | blue | 194 hr |
| Example 8 | Compound 60 | 6.33 | 50 | 2.467 | 4.93 | blue | 207 hr |
| Example 9 | Compound 65 | 6.81 | 50 | 2.613 | 5.23 | blue | 219 hr |
| Example 10 | Compound 67 | 6.68 | 50 | 2.587 | 5.17 | blue | 211 hr |
| Comparative Example 1 | $Alq_3$ | 7.85 | 50 | 1.560 | 3.12 | blue | 113 hr |

Referring to Table 1, it can be confirmed that when the heterocyclic compound represented by Formula 1 is used as an electron transport material of an organic light-emitting diode (Examples 1 to 10), the driving voltage of each organic light-emitting diode was decreased by about 1 V or more and the Luminous efficiency thereof was increased by about 1 to 2 cd/A than when the known material Alq$_3$ was used (Comparative Example 1). That is, the organic light-emitting diodes of Examples 1 to 10 show more excellent Current-Voltage-Luminance characteristics (I-V-L characteristics) than the Comparative Example 1. The excellent I-V-L characteristics mean low driving voltage and high luminous efficiency.

In particular, the lifetime of Examples 1 to 10 was about 80 to 110 hours longer. than that of Comparative Example 1.

From these results, it can be confirmed that the organic light-emitting diodes including the heterocyclic compound of Formula 1 have reduced driving voltage and improved luminous efficiency and thus, have excellent electrical stability, high charge transporting capability, and excellent light-emitting capability.

The heterocyclic compound represented by Formula 1 has high glass transition temperature and a crystallization prevention capability and thus, is useful for an electron transport material or an electron injection material that is suitable for various colors, such as red, green, blue, and white fluorescent and phosphorescent devices. Also, when the heterocyclic compound represented by Formula 1 is used as green, blue and white emission materials, it shows electrical stability, a high charge transporting capability, and an excellent light-emitting capability. An organic light-emitting diode including the heterocyclic compound represented by Formula 1 as an electron transport material or an emission material shows high efficiency, low voltage, high brightness, and long lifetime characteristics.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 below:

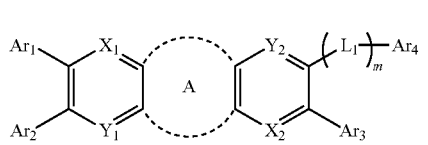

Formula 1 wherein one of $X_1$ and $Y_1$ is N and the other one is $CR_1$; one of $X_2$ and $Y_2$ is N and the other one is $CR_2$;

A is an unsubstituted phenanthrene ring, an unsubstituted anthracene ring, an unsubstituted fluoranthene ring, an unsubstituted triphenylene ring, an unsubstituted pyrene ring, an unsubstituted chrysene ring, an unsubstituted tetrahelicene ring, an unsubstituted perylene ring and an unsubstituted benzopyrene ring;

Ar$_1$ to Ar$_3$ are each independently a hydrogen atom, a deuterium atom, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted $C_2$-$C_{60}$ fused polycyclic group, a group represented by N(Q$_1$)(Q$_2$), or a group represented by Si(Q$_3$)(Q$_4$)(Q$_5$), wherein Q$_1$ to Q$_5$ are each independently a hydrogen atom, a deuterium atom, a halogen atom, a hydroxyl group, a cyano group, a nitro group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a substituted or unsubstituted $C_2$-$C_{60}$ fused polycyclic group, or a combination thereof; Ar$_4$ is a substituted or unsubstituted $C_2$-$C_{60}$ heteroaryl group; and from among Ar$_1$ to Ar$_4$, adjacent two or more thereof are optionally bonded to form a saturated or unsaturated ring;

L$_1$ is a substituted or unsubstituted phenylene group, a substituted or unsubstituted naphthylene group, a substituted or unsubstituted biphenylene group, a substituted or unsubstituted pentalenylene group, a substituted or unsubstituted indenylene group, a substituted or unsubstituted azulenylene group, a substituted or unsubstituted heptalenylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted triazolylene group, a substituted or unsubstituted oxadiazolylene group, a substituted or unsubstituted quinolinylene group, a substituted or unsubstituted thiophenylene group, or a combination thereof;

m is an integer of 0 to 3; and

R$_1$ and R$_2$ are each independently a hydrogen atom, a deuterium atom, a halogen atom, a hydroxyl group, a cyano group, a nitro group, a nitrile group, a carboxyl group, a silyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_1$-$C_{50}$ alkoxy group, a substituted or unsubstituted $C_3$-$C_{50}$ cycloalkyl group, a substituted or unsubstituted $C_3$-$C_{50}$ cycloalkenyl group, a substituted or unsubstituted $C_5$-$C_{60}$ aryl group, or a combination thereof.

2. The heterocyclic compound of claim 1, wherein the heterocyclic compound is represented by one of Formulae 5A to 5F below:

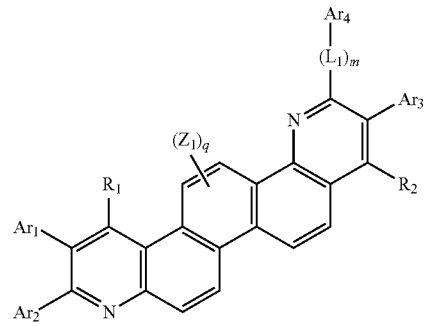

Formula 5A

Formula 5B
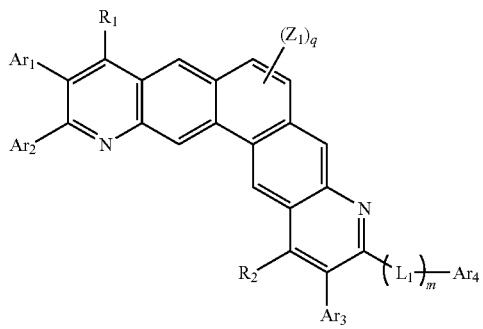
Formula 5C
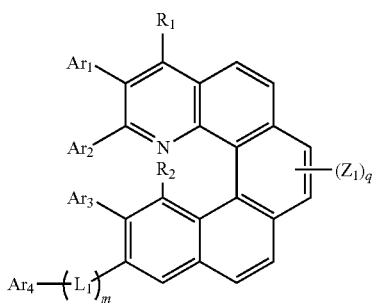
Formula 5D
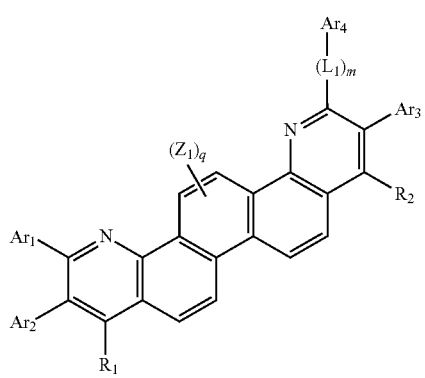
Formula 5E
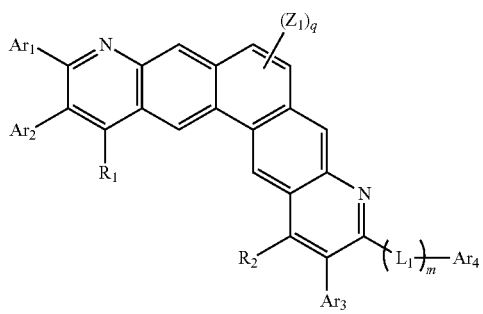
Formula 5F
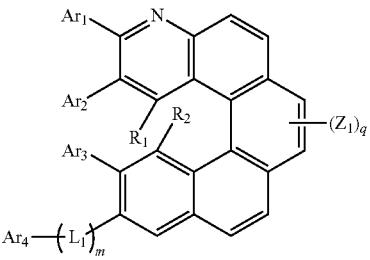
Wherein $Ar_1$, $Ar_2$, $Ar_3$, $Ar_4$, $L_1$, m, $R_1$ and $R_2$ have already been defined with reference to Formula 1;
$Z_1$ is a hydrogen atom; and
q is an integer of 1 to 6.
3. The heterocyclic compound of claim 1, wherein the heterocyclic compound is represented by one of Formulae 6A to 6F below:
Formula 6A
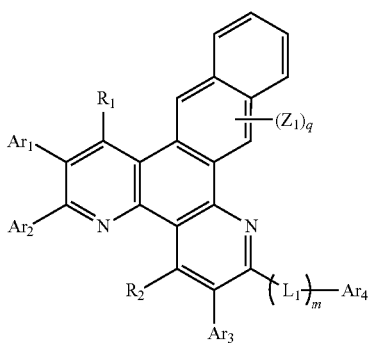
Formula 6B
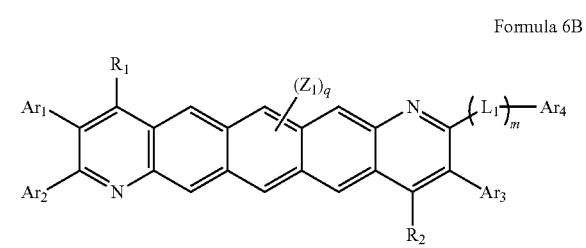
Formula 6C
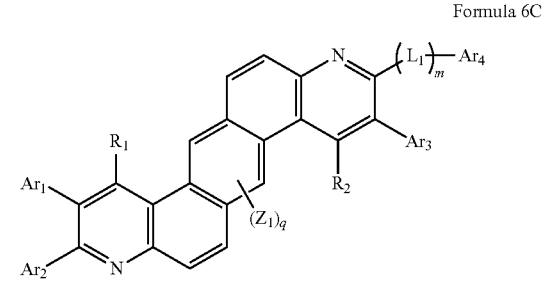

Formula 6D

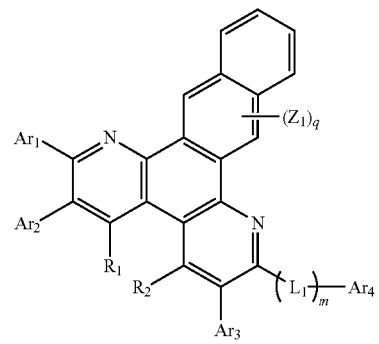

Formula 6E

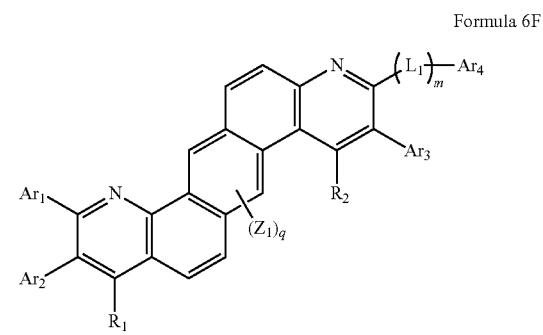

Formula 6F

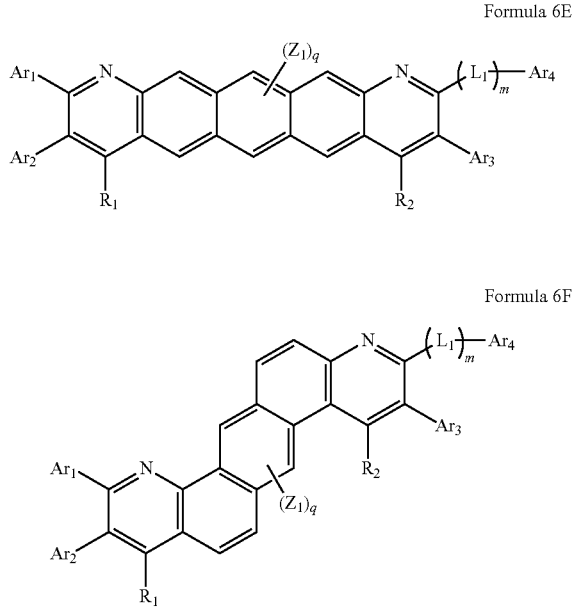

Wherein Ar$_1$, Ar$_2$, Ar$_3$, Ar$_4$, L$_1$, m, R$_1$ and R$_2$ have already been defined with reference to Formula 1;

Z$_1$ is a hydrogen atom; and q is an integer of 1 to 6.

4. The heterocyclic compound of claim 1, wherein the heterocyclic compound is represented by one of Formulae 7A to 7F below:

Formula 7A

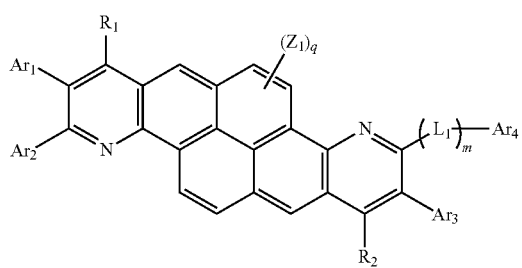

Formula 7B

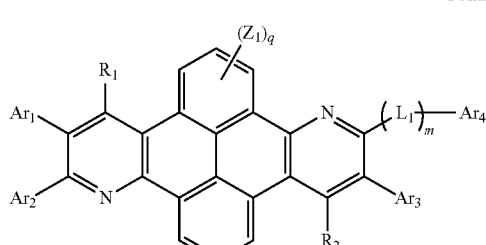

Formula 7C

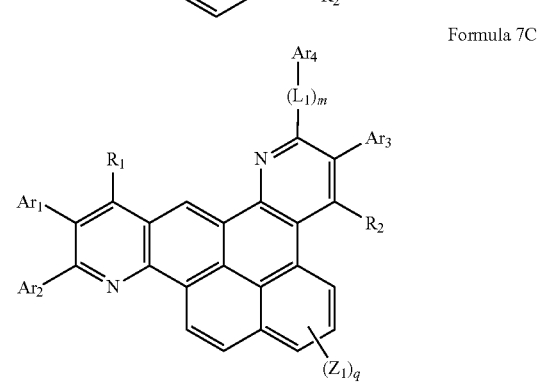

Formula 7D

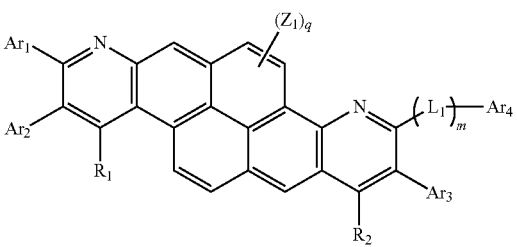

Formula 7E

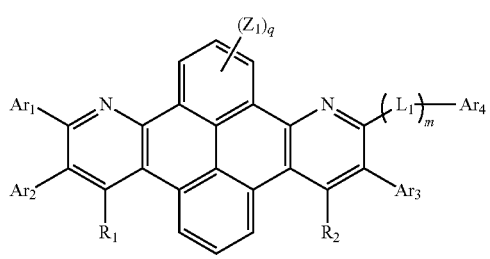

Formula 7F

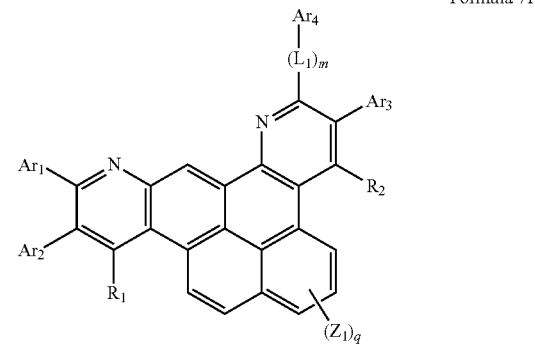

Wherein Ar$_1$, Ar$_2$, Ar$_3$, Ar$_4$, L$_1$, m, R$_1$ and R$_2$ have already been defined with reference to Formula 1;

Z$_1$ is a hydrogen atom; and q is an integer of 1 to 6.

5. The heterocyclic compound of claim 1, wherein the heterocyclic compound is represented by one of Formulae 8A to 8F below:

Formula 8A

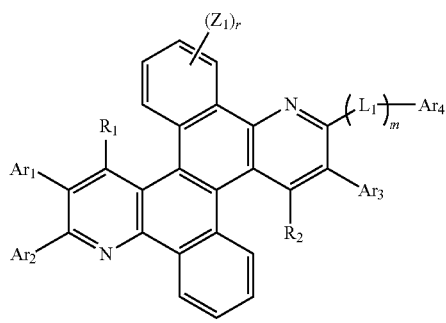

Formula 8B

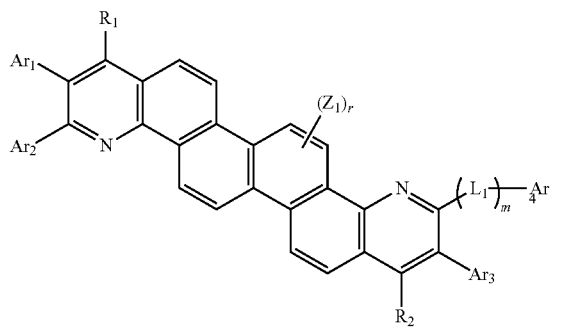

Formula 8C

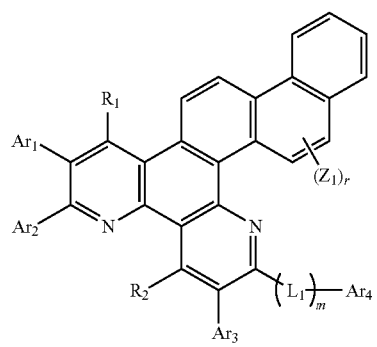

Formula 8D

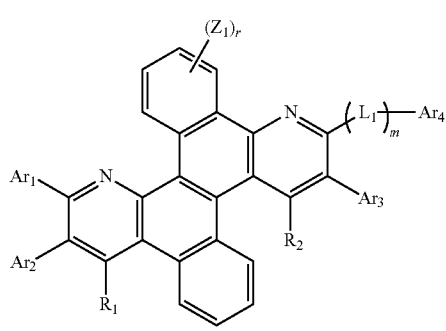

Formula 8E

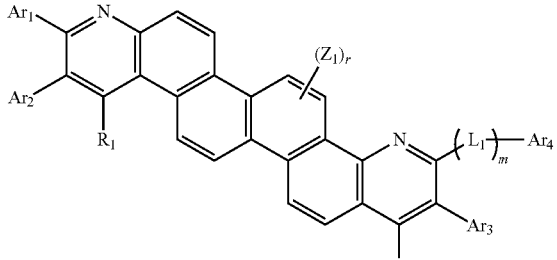

Formula 8F

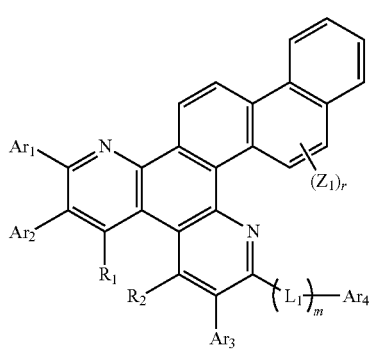

Wherein $Ar_1$, $Ar_2$, $Ar_3$, $An_4$, $L_1$, m, $R_1$ and $R_2$ have already been defined with reference to Formula 1;
$Z_1$ is a hydrogen atom; and
r is an integer of 1 to 8.

6. The heterocyclic compound of claim 1, wherein the heterocyclic compound is represented by Formula 9A or 9B:

Formula 9A

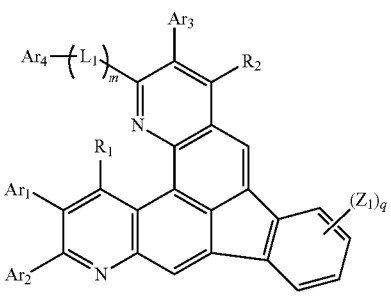

Formula 9B

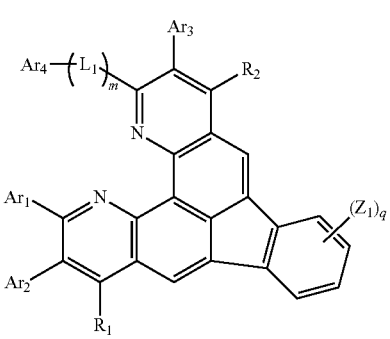

Wherein $Ar_1$, $Ar_e$, $Ar_a$, $An_r$, $L_1$, m, $R_1$ and $R_2$ have already been defined with reference to Formula 1;
$Z_1$ is a hydrogen atom; and
q is an integer of 1 to 6.

7. The heterocyclic compound of claim 1, wherein the heterocyclic compound is represented by one of Formulae 10A to 10F below:

Formula 10A

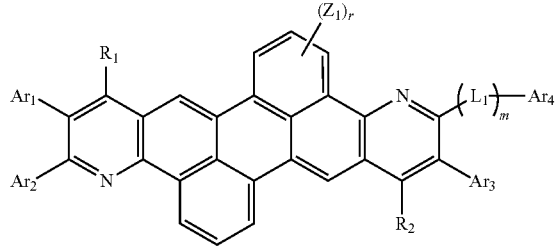

Formula 10B

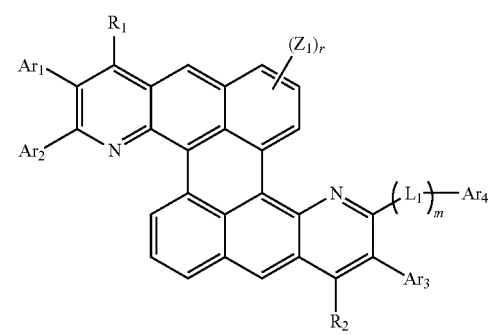

Formula 10C

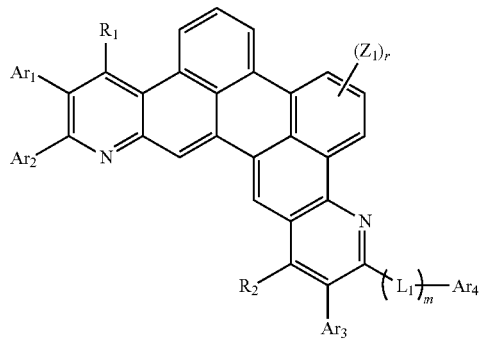

Formula 10D

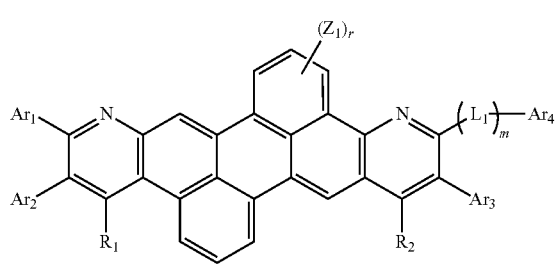

Formula 10E

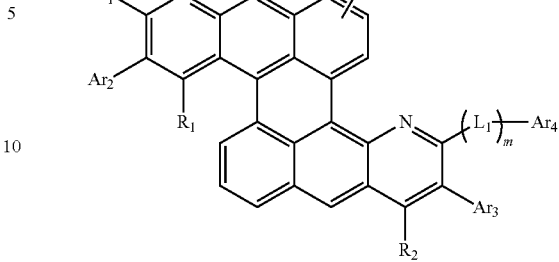

Formula 10F

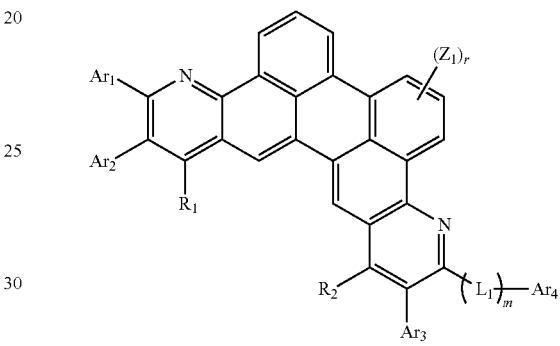

Wherein $Ar_1$, $Ar_2$, $Ar_3$, $An_4$, $L_1$, m, $R_1$ and $R_2$ have already been defined with reference to Formula 1;

$Z_1$ is a hydrogen atom; and r is an integer of 1 to 8.

8. The heterocyclic compound of claim 1, wherein the heterocyclic compound is represented by Formula 11A or 11B below:

Formula 11A

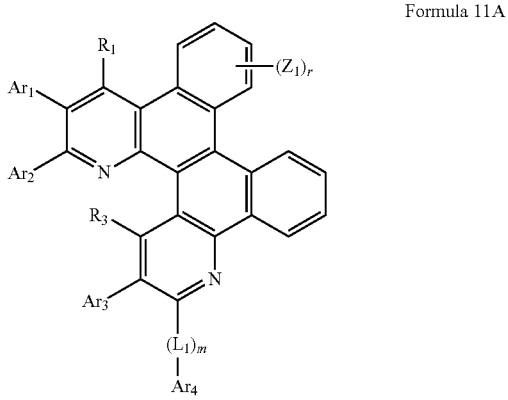

-continued

Formula 11B

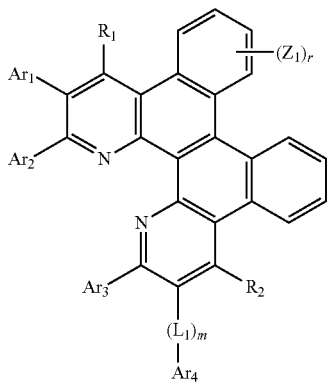

Formula 13A

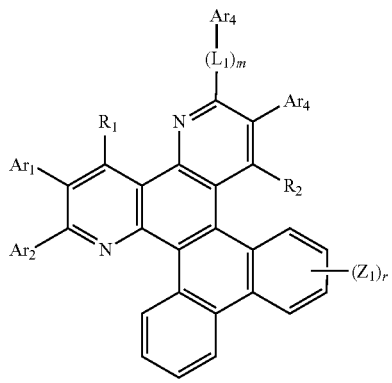

Wherein Ar₁, Ar₂, Ar₃, Ar₄, L₁, m, R₁ and R₂ have already been defined with reference to Formula 1;

Z₁ is a hydrogen atom; and r is an integer of 1 to 8.

9. The heterocyclic compound of claim 1, wherein the heterocyclic compound is represented by one of Formula 12A or 12B below:

Formula 12A

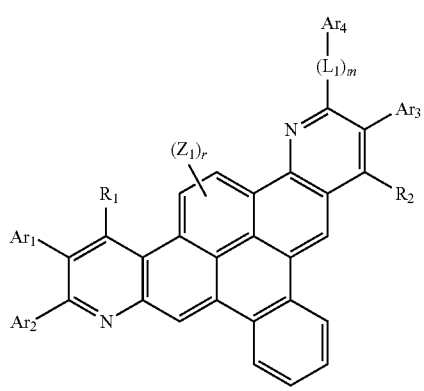

Formula 13B

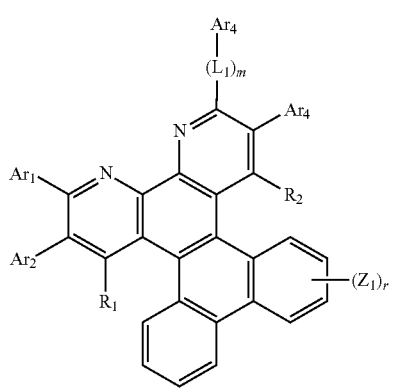

Formula 12B

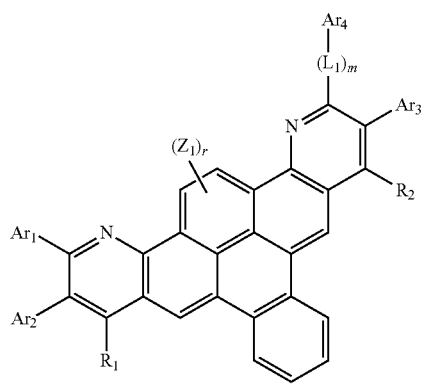

Wherein Ar₁, Ar₂, Ar₃, An₄, L₁, m, R₁ and R₂ have already been defined with reference to Formula 1;

Z₁ is a hydrogen atom; and r is an integer of 1 to 8.

11. A heterocyclic compound represented by one of Compounds 1 to 79:

2

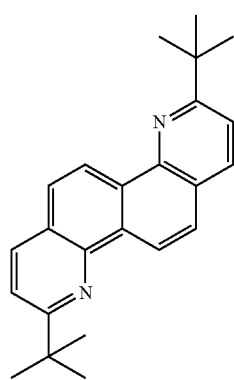

Wherein Ar₁, Ar₂, Ar₃, An₄, L₁, m, R₁ and R₂ have already been defined with reference to Formula 1;

Z₁ is a hydrogen atom; and r is an integer of 1 to 8.

10. The heterocyclic compound of claim 1, wherein the heterocyclic compound is represented by Formula 13A or 13B below:

6
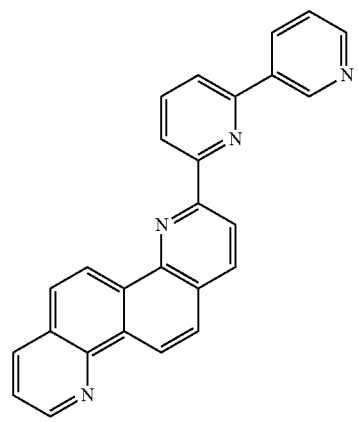
11
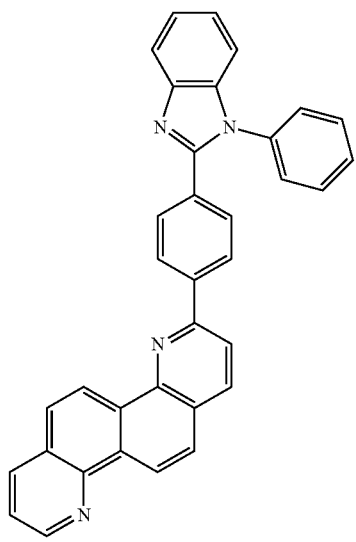
12
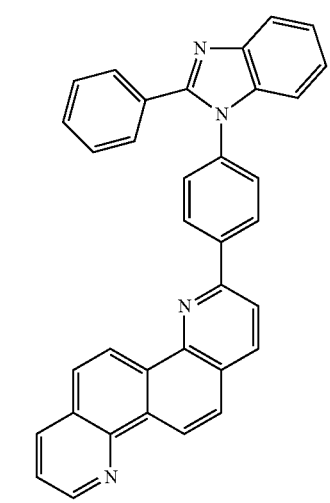
13
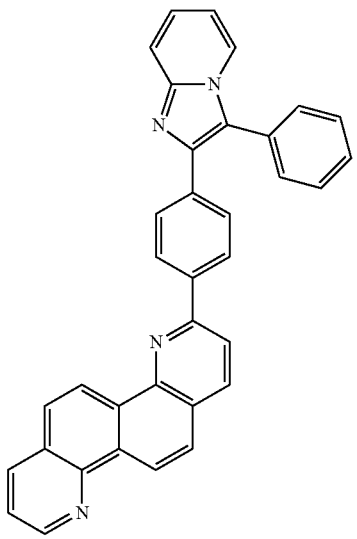
14
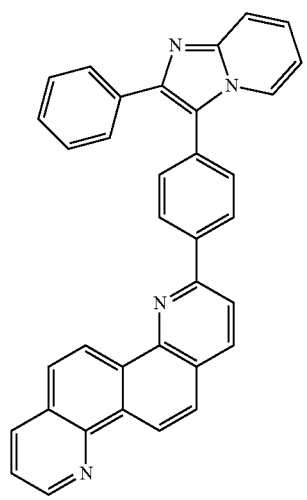
15
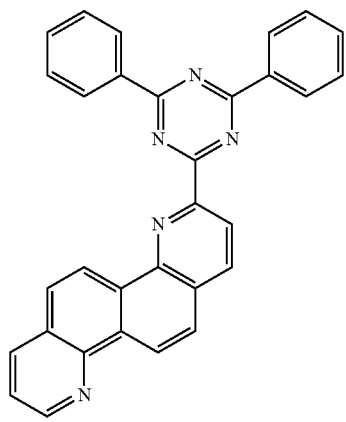

16
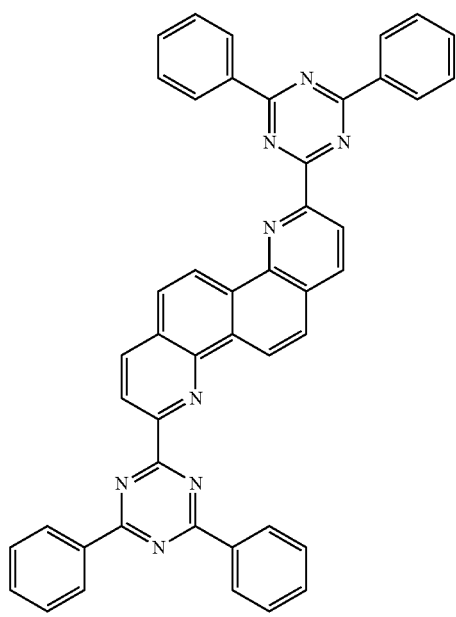
17
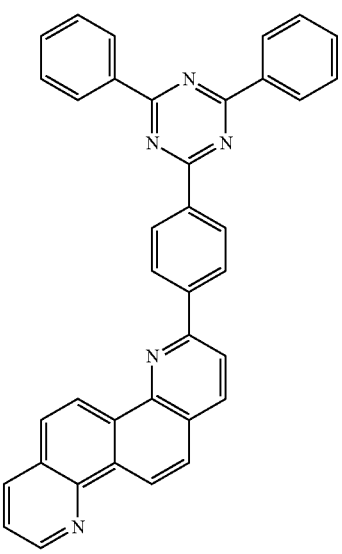
18
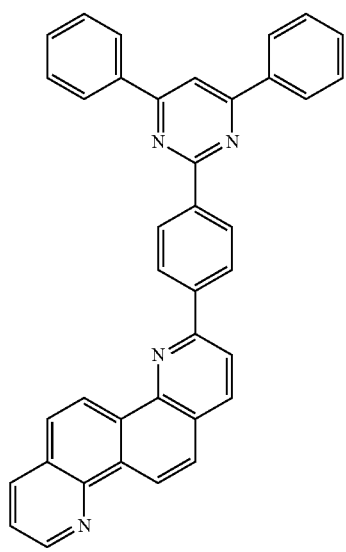
19
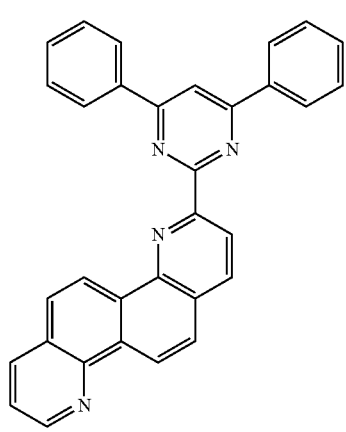
20
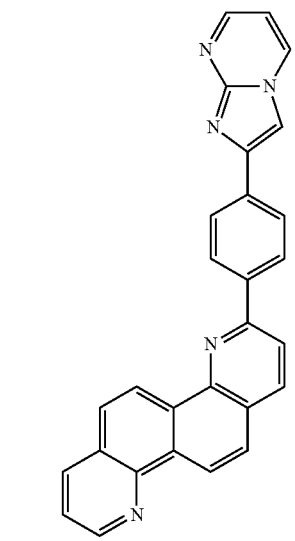

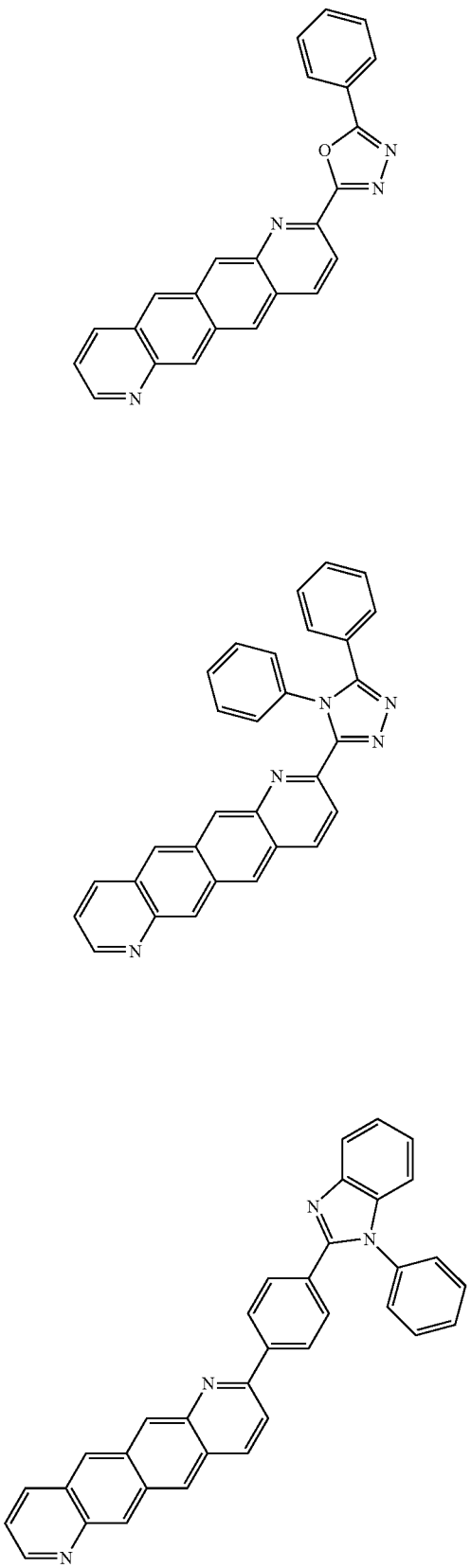
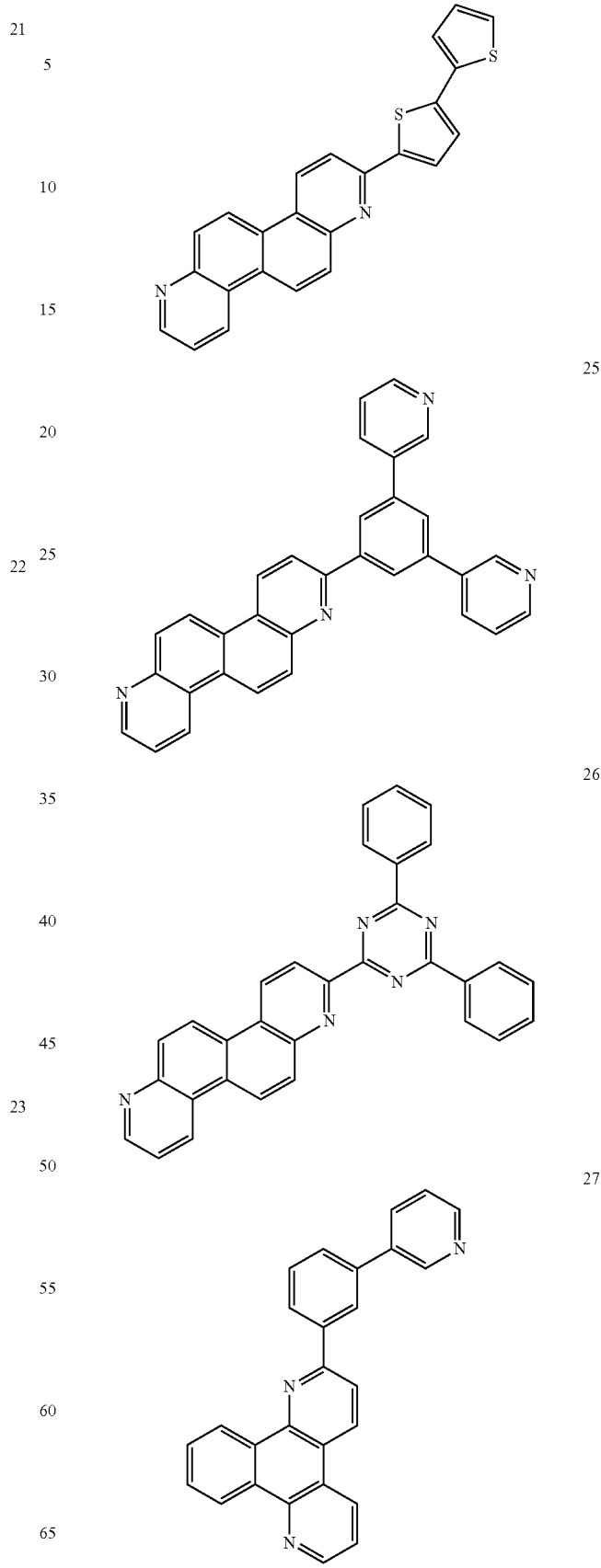

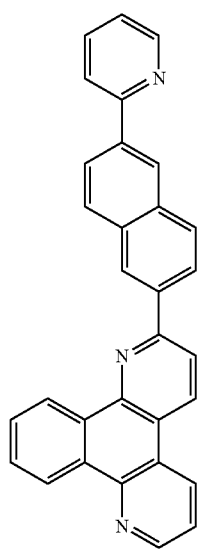
28
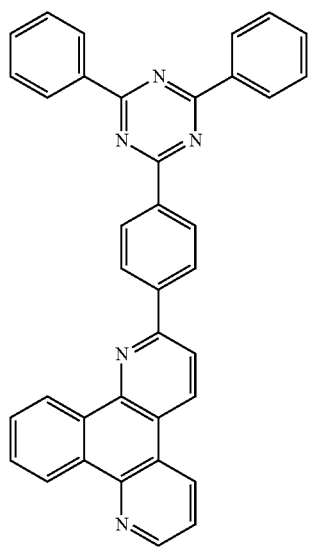
29
30
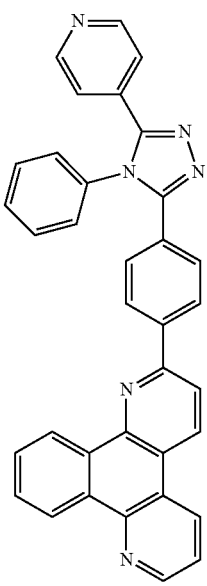
31
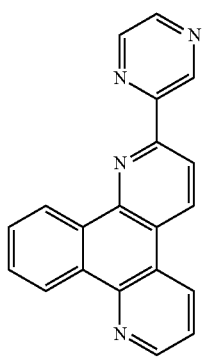
32
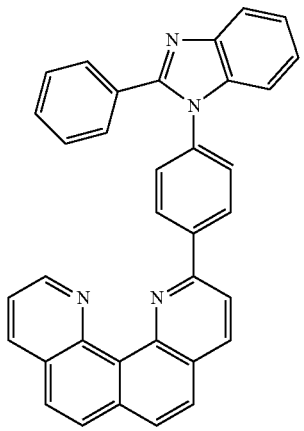
33

34
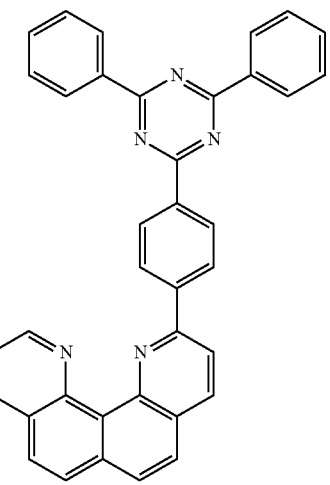
35
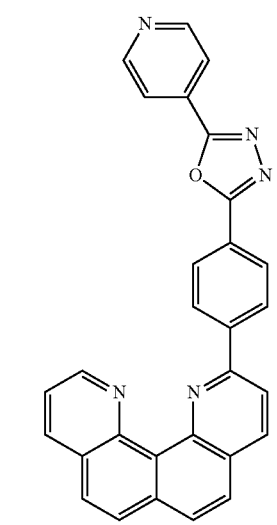
36
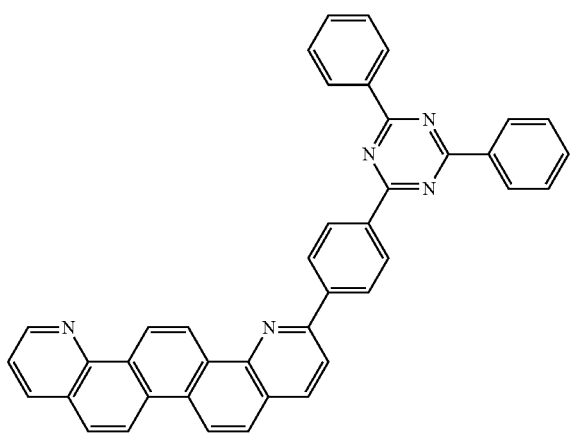
37
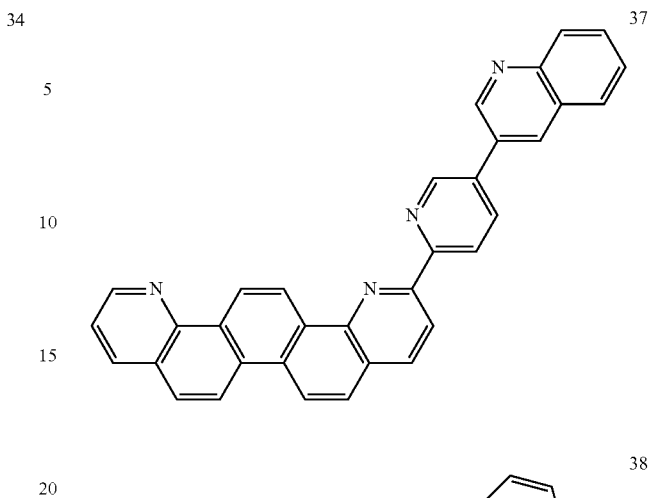
38
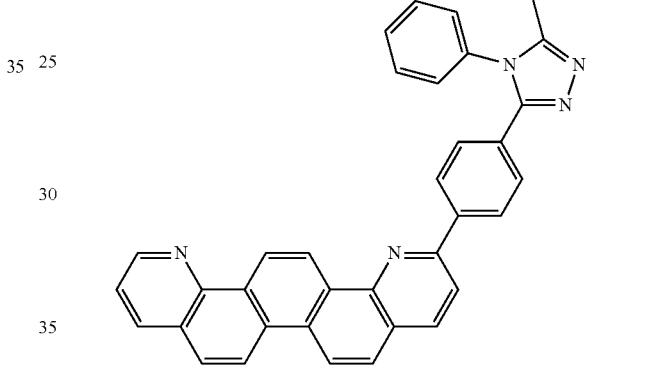
39
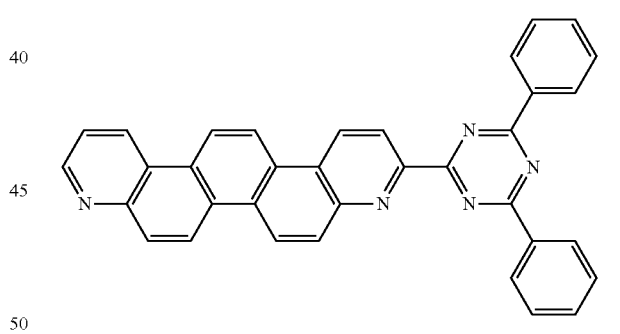
40
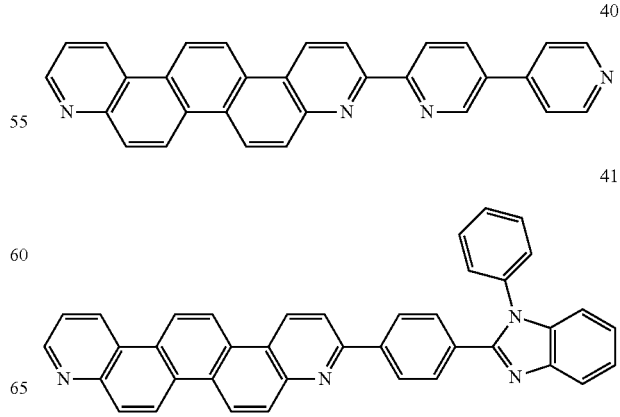
41

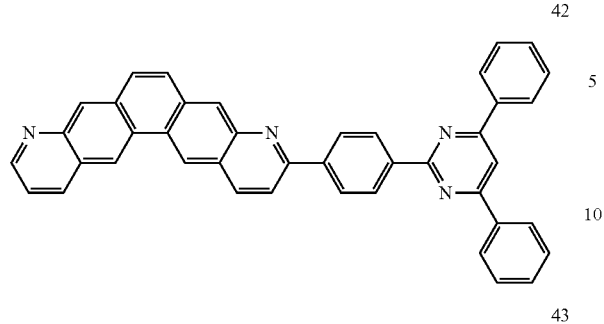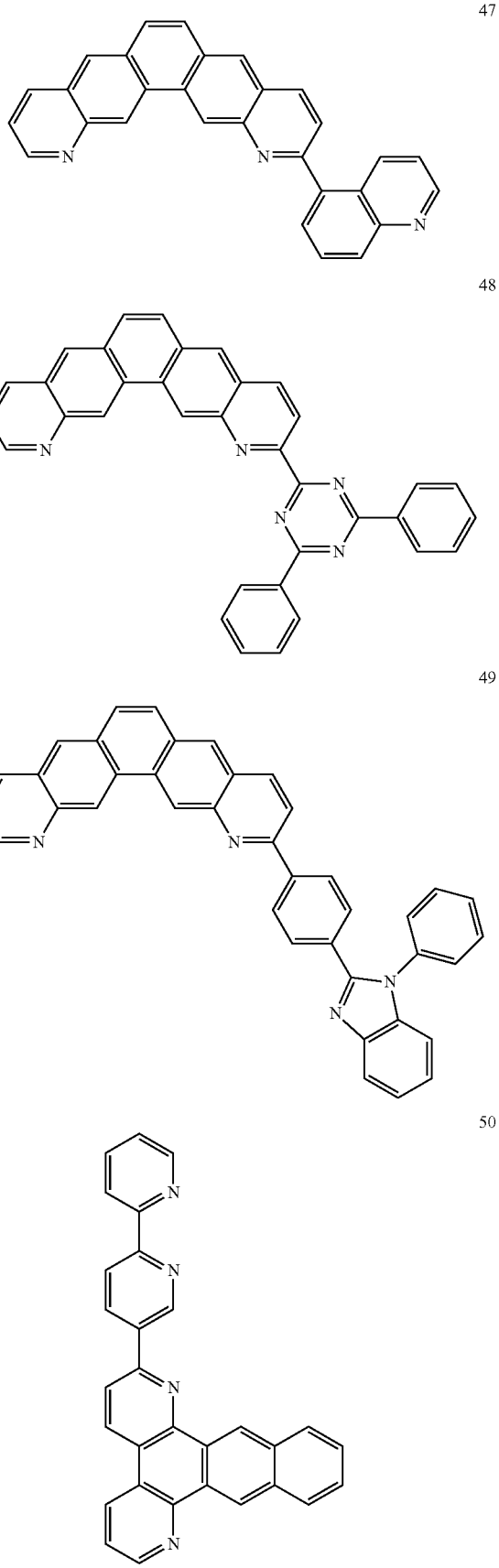

51
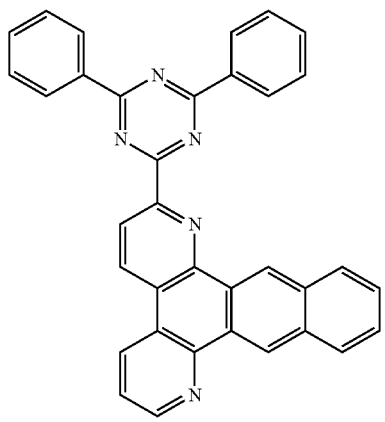
52
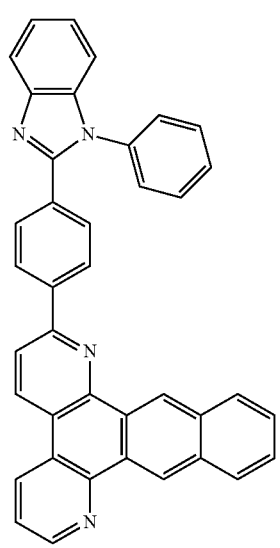
53
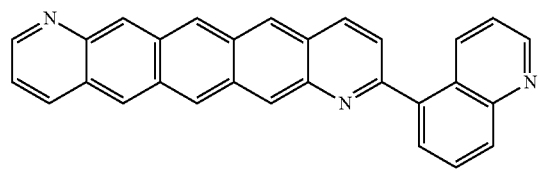
54
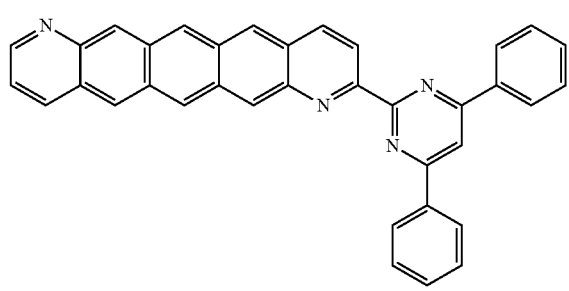
55
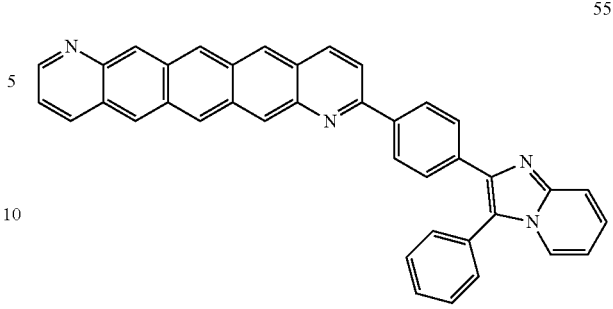
56
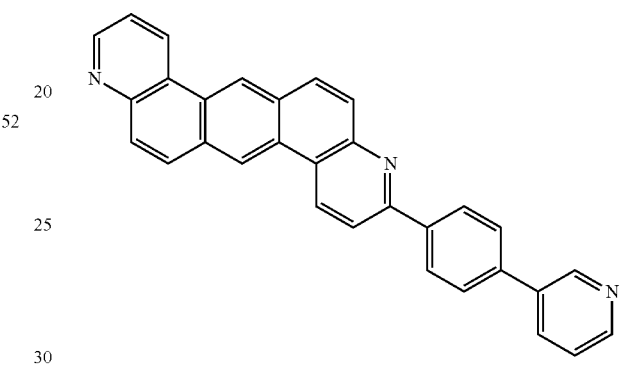
57
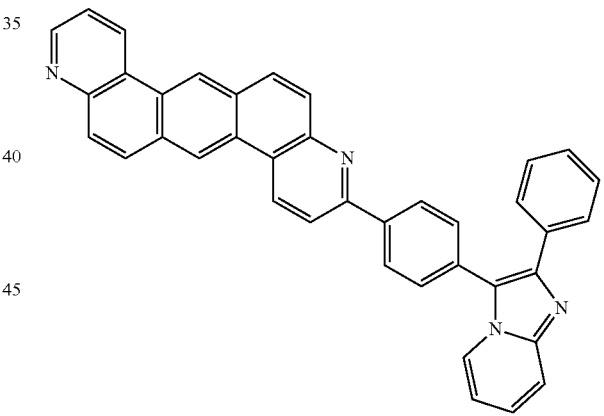
58
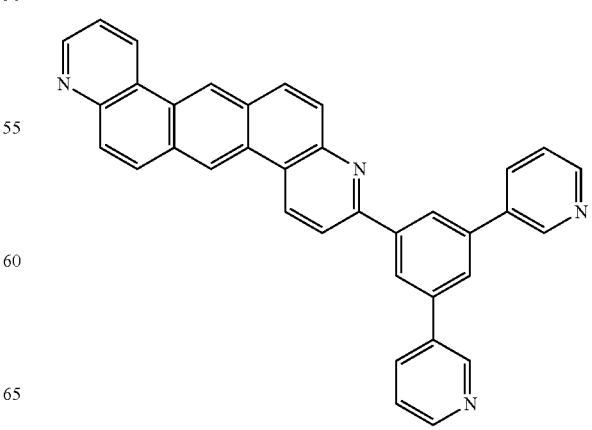

59
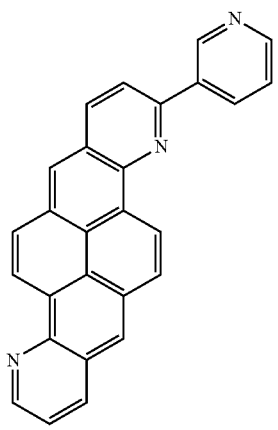
60
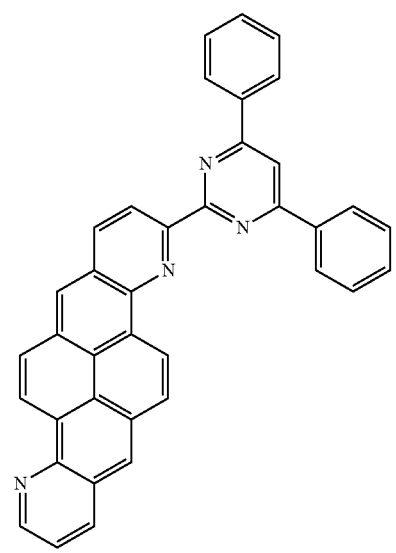
61
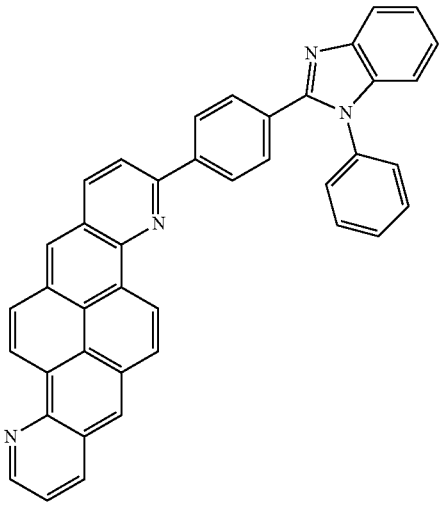
62
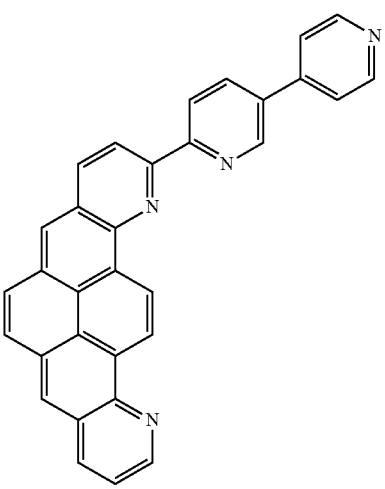
63
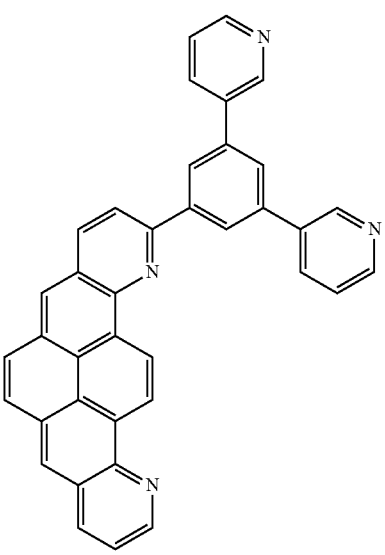
64
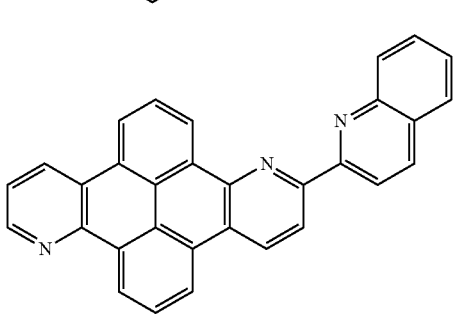
65
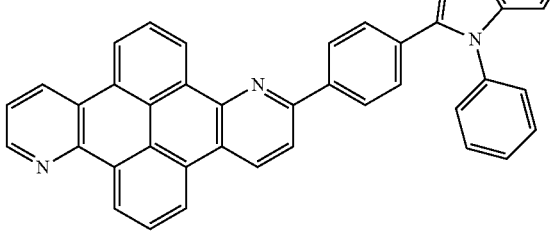

107
-continued
66
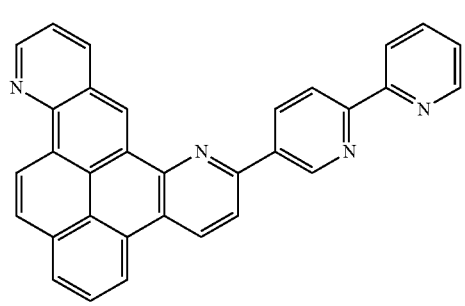
67
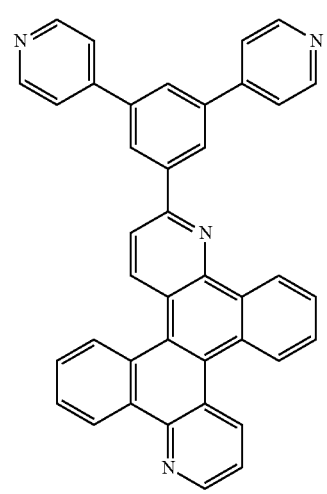
68
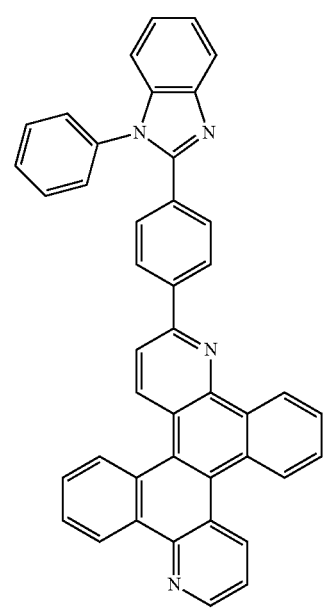
108
-continued
69
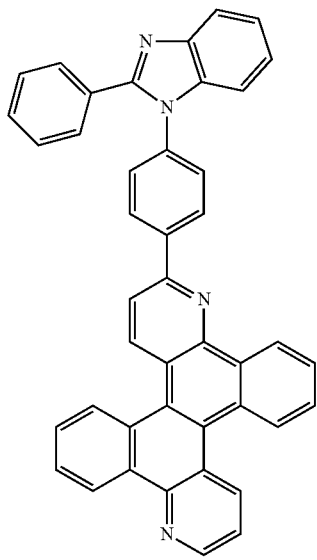
70
71
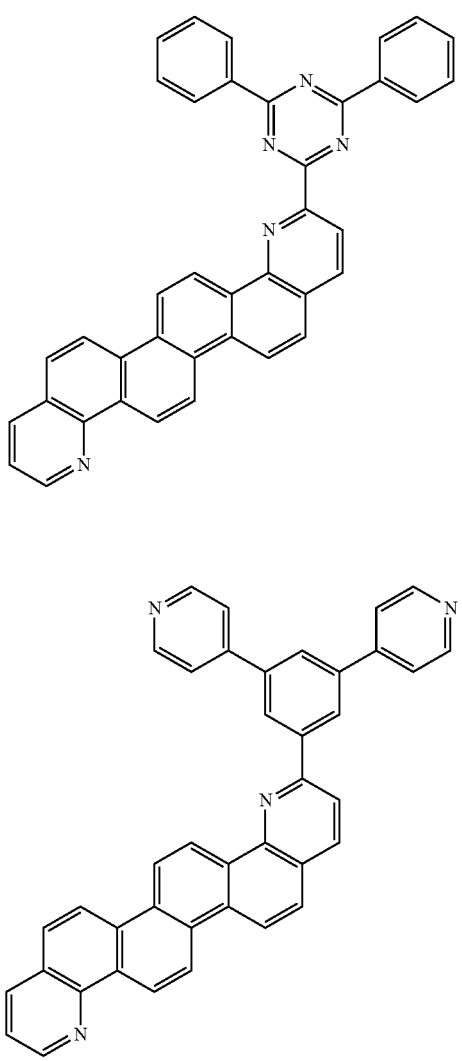

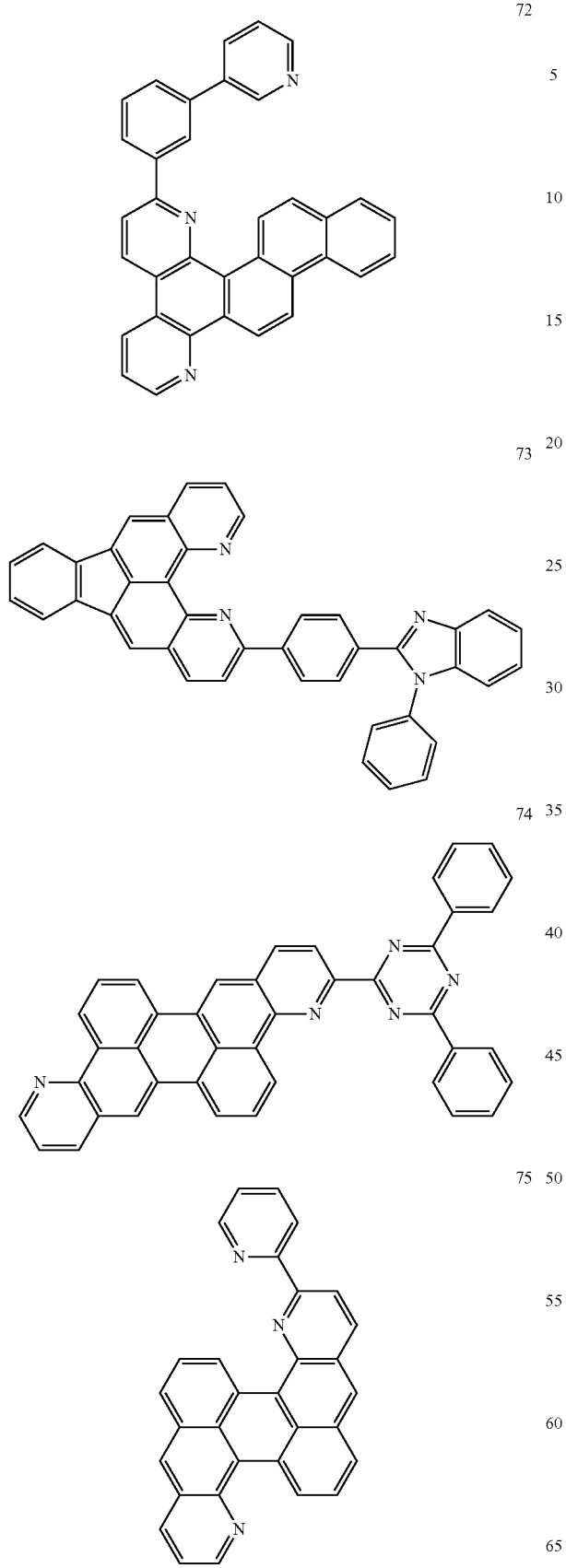
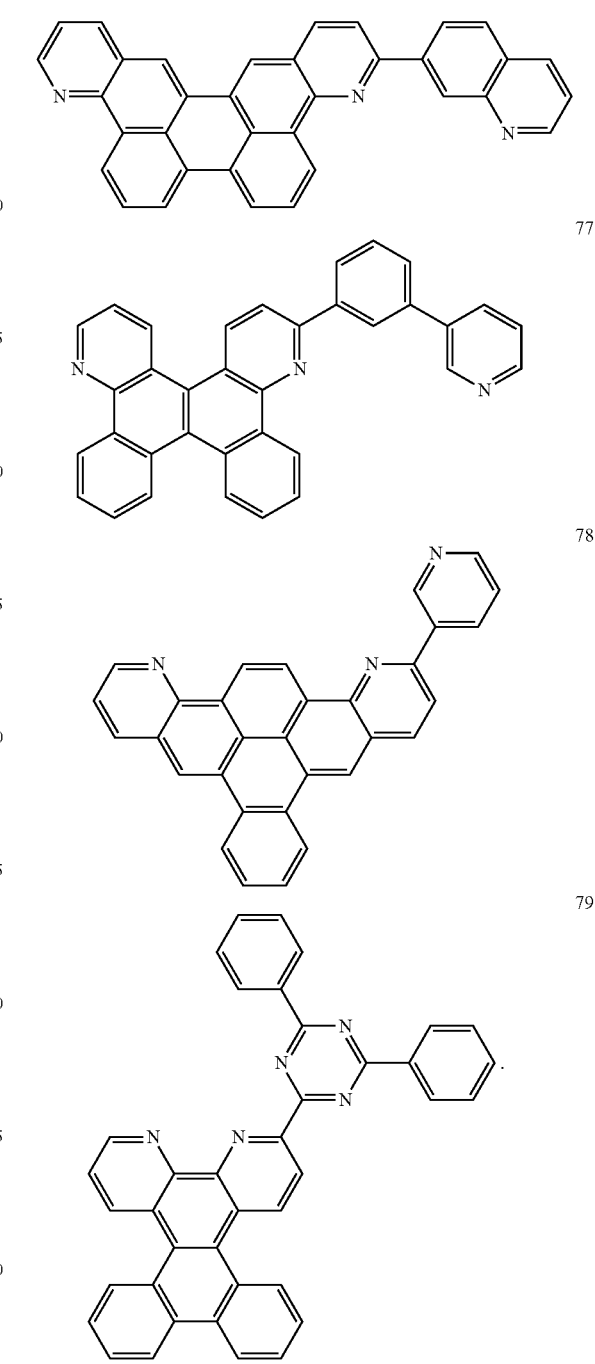

12. An organic light-emitting diode comprising:
   a first electrode;
   a second electrode facing the first electrode; and
   an organic layer interposed between the first electrode and the second electrode, wherein the organic layer comprises the heterocyclic compound of claim 1 alone or in a mixed form with other materials.

13. The organic light-emitting diode of claim 12, wherein the organic layer comprises at least one layer selected from a hole injection layer, a hole transport layer, a functional layer having a hole injection capability and a hole transport capability, an electron blocking layer, an emission layer, a hole blocking layer, an electron transport layer, an electron injection layer, and a functional layer having an electron transport capability and an electron injection capability.

14. The organic light-emitting diode of claim 12, wherein the organic layer comprises an emission layer, wherein the emission layer comprises the heterocyclic compound of claim 1 alone or in a mixed form with other materials.

15. The organic light-emitting diode of claim 12, wherein the organic layer comprises at least one layer selected from an electron transport layer, an electron injection layer, and a functional layer having an electron transport capability and an electron injection capability, wherein the at least one layer comprises the heterocyclic compound.

16. The organic light-emitting diode of claim 12, wherein the organic layer comprises at least one layer selected from an electron transport layer, an electron injection layer, and a functional layer having an electron transport capability and an electron injection capability; and an emission layer comprising at least one layer selected from a red emission layer, a green emission layer, a blue emission layer, and a white emission layer,
   wherein the at least one layer selected from an electron transport layer, an electron injection layer, and a functional layer having an electron transport capability and an electron injection capability comprises the heterocyclic compound and the emission layer comprises a phosphorescent compound.

\* \* \* \* \*